(12) United States Patent
Liu et al.

(10) Patent No.: US 10,787,708 B2
(45) Date of Patent: Sep. 29, 2020

(54) METHOD OF IDENTIFYING A GENE ASSOCIATED WITH A DISEASE OR PATHOLOGICAL CONDITION OF THE DISEASE

(71) Applicant: Macau University of Science and Technology, Taipa (MO)

(72) Inventors: Liang Liu, Taipa (MO); Lai Han Leung, Taipa (MO); Ying Li, Taipa (MO); Xiao Jun Yao, Taipa (MO); Hu Dan Pan, Taipa (MO)

(73) Assignee: Macau University of Science and Technology, Taipa (MO)

( * ) Notice: Subject to any disclaimer, the term of this patent is extended or adjusted under 35 U.S.C. 154(b) by 374 days.

(21) Appl. No.: 15/647,414

(22) Filed: Jul. 12, 2017

(65) Prior Publication Data

US 2019/0017116 A1    Jan. 17, 2019

(51) Int. Cl.
| | |
|---|---|
| *C12Q 1/6883* | (2018.01) |
| *G16B 30/00* | (2019.01) |
| *G16B 50/00* | (2019.01) |
| *G16B 20/20* | (2019.01) |
| *G16B 5/00* | (2019.01) |
| *G16B 15/00* | (2019.01) |
| *G16B 40/20* | (2019.01) |
| *C12Q 1/6869* | (2018.01) |

(52) U.S. Cl.
CPC .......... *C12Q 1/6883* (2013.01); *G16B 20/20* (2019.02); *G16B 30/00* (2019.02); *G16B 50/00* (2019.02); *C12Q 1/6869* (2013.01); *C12Q 2600/156* (2013.01); *G16B 5/00* (2019.02); *G16B 15/00* (2019.02); *G16B 40/20* (2019.02)

(58) Field of Classification Search
CPC .................................................. C12Q 1/6883
USPC ......................................................... 702/19
See application file for complete search history.

(56) References Cited

PUBLICATIONS

Stahl EA, Raychaudhuri S, Remmers EF, et al. Genome-wide association study meta-analysis identifies seven new rheumatoid arthritis risk loci. Nat Genet 2010;42:508-514.
Freudenberg J, Lee HS, Han BG, et al. Genome-wide association study of rheumatoid arthritis in Koreans: population-specific loci as well as overlap with European susceptibility loci. Arthritis Rheum 2011;63:884-893.
Jiang L, Yin J, Ye L, et al. Novel risk loci for rheumatoid arthritis in Han Chinese and congruence with risk variants in Europeans. Arthritis Rheumatol 2014; 66:1121-1132.
Manolio TA, Collins FS, Cox NJ, et al. Finding the missing heritability of complex diseases. Nature 2009;461:747-753.
Ng SB, Buckingham KJ, Lee C, et al. Exome sequencing identifies the cause of a mendelian disorder. Nat Genet 2010;42:30-35.
Welter D, MacArthur J, Morales J, et al. The NHGRI GWAS Catalog, a curated resource of SNP-trait associations. Nucleic acids research 2014;42:D1001-D1006.
Okada Y, Wu D, Trynka G, et al. Genetics of rheumatoid arthritis contributes to biology and drug discovery. Nature 2014;506:376-381.
Diogo D, Kurreeman F, Stahl EA, et al. Rare, low-frequency, and common variants in the protein-coding sequence of biological candidate genes from GWASs contribute to risk of rheumatoid arthritis. The American Journal of Human Genetics 2013;92:15-27.
San Lucas FA, Wang G, Scheet P, Peng B. Integrated annotation and analysis of genetic variants from next-generation sequencing studies with variant tools. Bioinformatics 2012;28:421-422.
Dong C, Wei P, Jian X, Gibbs R, Boerwinkle E, Wang K, Liu X. Comparison and integration of deleteriousness prediction methods for nonsynonymous SNVs in whole exome sequencing studies. Human molecular genetics 2015;24:2125-2137.
Yamaguchi H, Akitaya T, Yu T, Kidachi Y, Kamiie K, Noshita T, Umetsu H, Ryoyama K. Homology modeling and structural analysis of 11β-hydroxysteroid dehydrogenase type 2. European journal of medicinal chemistry 2011; 46:1325-1330.
Levitt M. Accurate modeling of protein conformation by automatic segment matching. Journal of molecular biology 1992; 226:507-533.
Zhou TB, Zhao HL, Fang SL, Drummen GP. Association of transforming growth factor-beta1 T869C, G915C, and C509T gene polymorphisms with rheumatoid arthritis risk. J Recept Signal Transduct Res 2014; 34:469-475.
Paradowska-Gorycka A, Jurkowska M, Felis-Giemza A, Romanowska-Prochnicka K, Manczak M, Maslinski S, Olesinska M. Genetic polymorphisms of Foxp3 in patients with rheumatoid arthritis. J Rheumatol 2015; 42:170-180.

(Continued)

*Primary Examiner* — Jerry Lin
(74) *Attorney, Agent, or Firm* — Renner Kenner Greive Bobak Taylor & Weber

(57) ABSTRACT

A method of identifying a gene associated with a disease or pathological condition of the disease includes: a) obtaining a first group of exome sequences from a first population suffering from the disease or pathological condition and a second group of exome sequences from a second population not having the disease or pathological condition; b) identifying one or more variants in the first group by comparing it with the second group, and optionally with a public database, to generate a first set of variant data; c) applying a variant quality score calibration tool with a truth sensitivity threshold to remove false-positive variants having a sensitivity lower than the threshold and background variants from the first set of variant data so as to obtain a second set of variant data; d) removing synonymous variants from the second set of variant data to obtain a third set of variant data; and e) identifying one or more deleterious variants from the third set of variant data using a gene burden analysis, optionally generating a fourth set of variant data.

12 Claims, 8 Drawing Sheets
(5 of 8 Drawing Sheet(s) Filed in Color)
Specification includes a Sequence Listing.

(56) References Cited

PUBLICATIONS

Lv W, Wang Q, Chen H, et al. Prioritization of rheumatoid arthritis risk subpathways based on global immune subpathway interaction network and random walk strategy. Mol Biosyst 2015; 11:2986-2997.

Connolly M, Mullan RH, McCormick J, et al. Acute-phase serum amyloid A regulates tumor necrosis factor alpha and matrix turnover and predicts disease progression in patients with inflammatory arthritis before and after biologic therapy. Arthritis Rheum 2012;64:1035-1045.

Zhang X, Zhang D, Jia H, et al. The oral and gut microbiomes are perturbed in rheumatoid arthritis and partly normalized after treatment. Nat Med 2015;21:895-905.

Bennett CL, Christie J, Ramsdell F, et al. The immune dysregulation, polyendocrinopathy, enteropathy, X-linked syndrome (IPEX) is caused by mutations of FOXP3. Nature genetics 2001;27:20.

Luksan O, Jirsa M, Eberova J, et al. Disruption of OTC promoter-enhancer interaction in a patient with symptoms of ornithine carbamoyltransferase deficiency. Hum Mutat 2010;31:E1294-1303.

Eon GW, Kwon MJ, Lee SJ, Sin JB, Ki CS. Clinical and genetic analysis of a Korean patient with X-linked chondrodysplasia punctata: identification of a novel splicing mutation in the ARSE gene. Ann Clin Lab Sci 2013; 43:70-75.

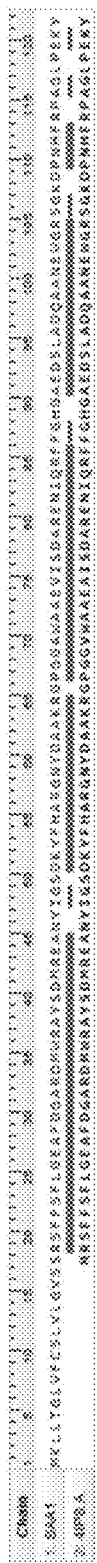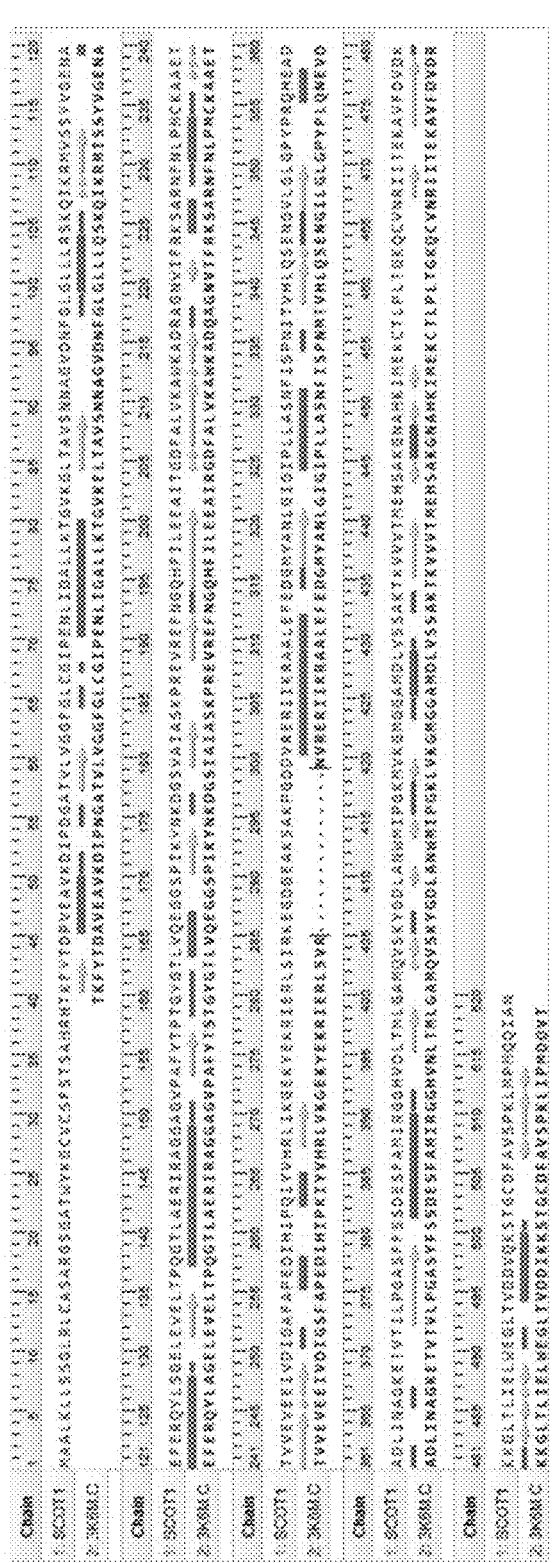
Fig. 4A
Fig. 4B

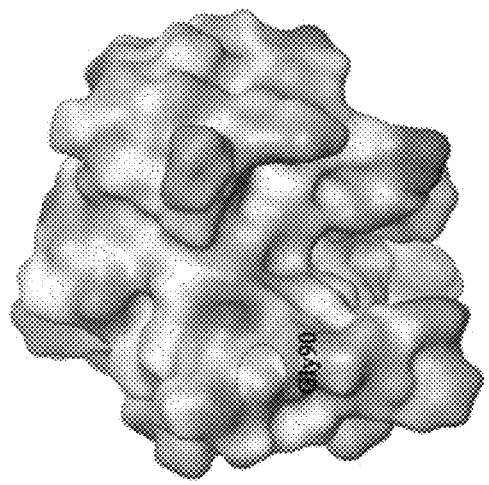
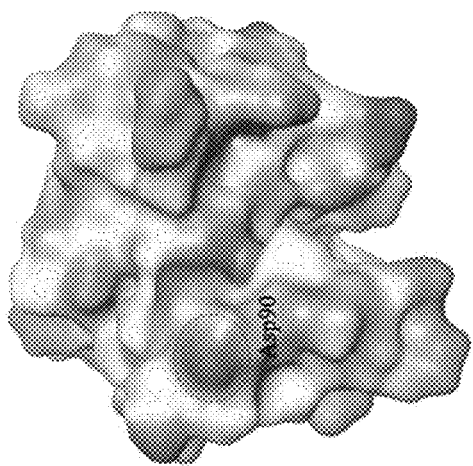
Fig. 6A
Fig. 6B
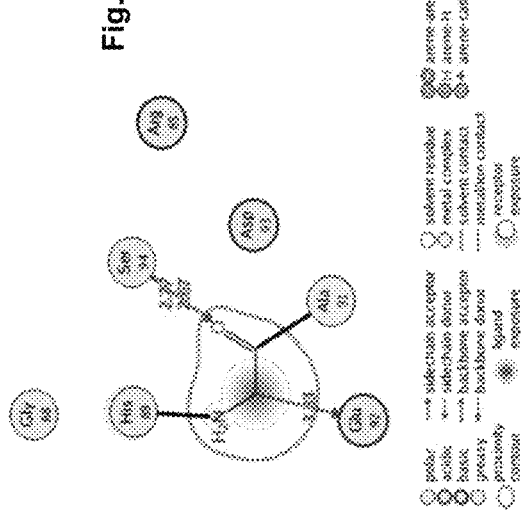
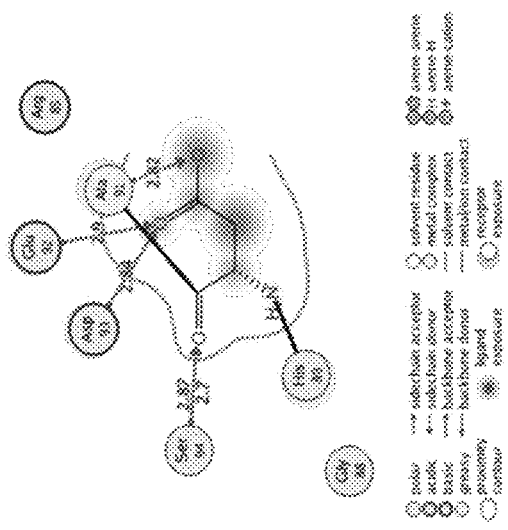
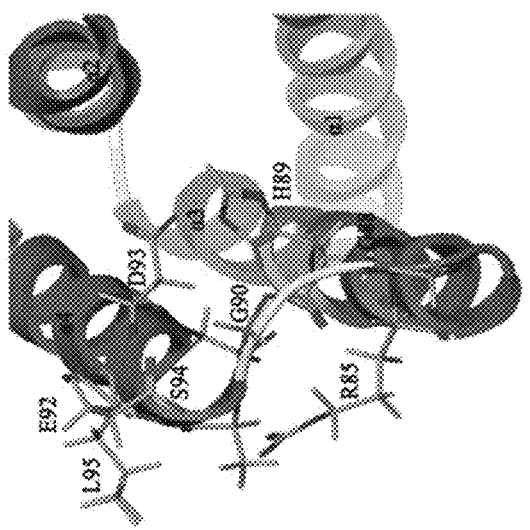
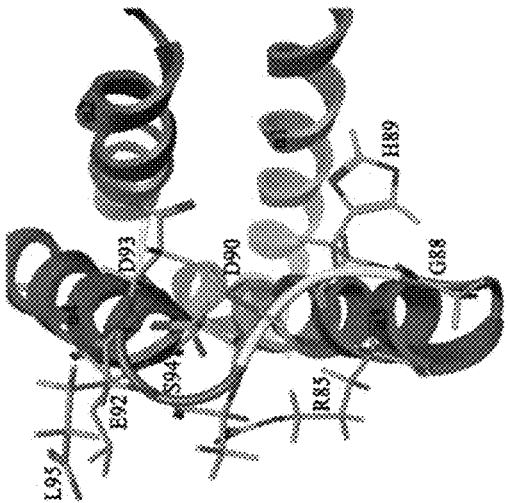

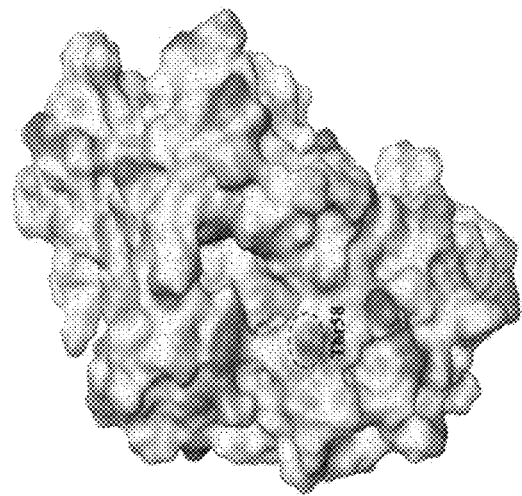
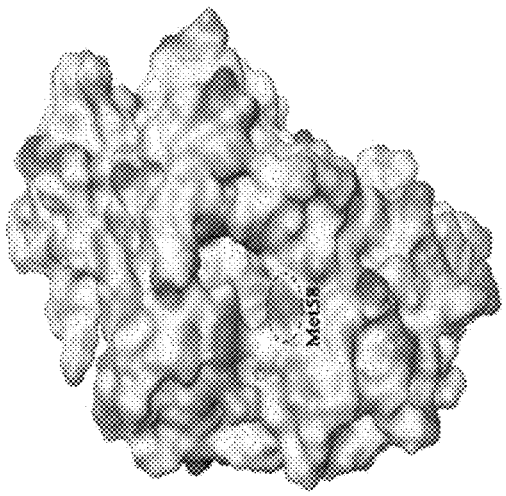
Fig. 6C
Fig. 6D
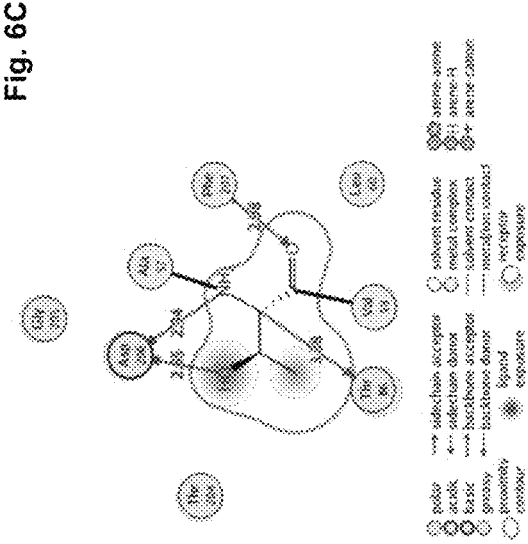
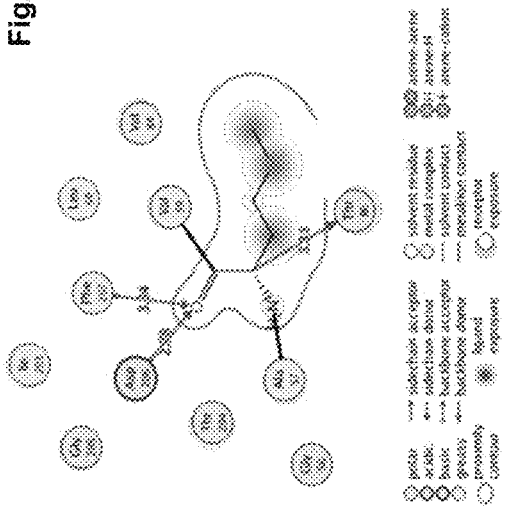
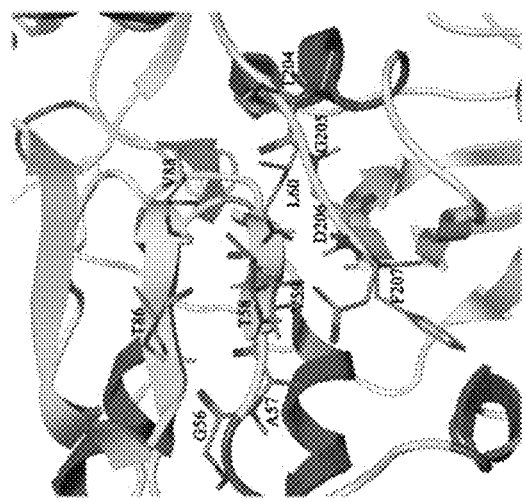
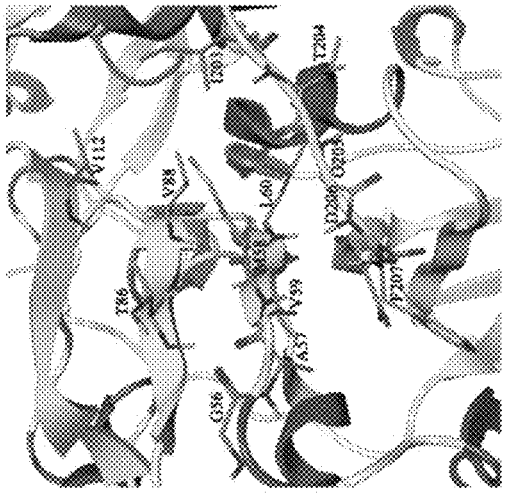

| group | variant | ref | alt | gene | gender | No. of cases with alt alleles |
|---|---|---|---|---|---|---|
| 2 | chrX:38229135 (rs72554348) | G | C | OCT | female | 4 |
|   |   |   |   |   | male | 1 |
| 5 | chrX:96396659 (rs363755) | C | T | DIAPH2 | female | 2 |
|   |   |   |   |   | male | 1 |
| 6 | chrX:2871176 (rs56393981) | G | A | ARSE | female | 4 |
|   |   |   |   |   | male | 1 |
| 6 | chrX:49114808 | C | A | FOXP3 | female | 7 |
|   |   |   |   |   | male | 1 |

METHOD OF IDENTIFYING A GENE ASSOCIATED WITH A DISEASE OR PATHOLOGICAL CONDITION OF THE DISEASE

SEQUENCE LISTING

The Sequence Listing file entitled "sequencelisting" having a size of 2,039 bytes and a creation date of 12 Jul. 2017 that was filed with the patent application is incorporated herein by reference in its entirety.

TECHNICAL FIELD

The present application relates to a method of identifying a gene associated with a disease or its pathological condition. In particular, but not exclusively, the method makes use of exome sequences for the identification.

BACKGROUND OF THE INVENTION

To date, there are various methods of determining the pathogenic gene form the human genome, for example, by whole-genome sequencing. Whole-exome sequencing (WES) has become a popular means for studying the genetic information, in particular for investigating the disease related genes. However, WES studies are generally susceptible to genotyping errors which may significantly affect the results.

Rheumatoid arthritis (RA) is the most common form of systemic autoimmune arthritis with unknown etiology, characterized by systemic inflammation and persistent poly-joint synovitis, principally leading to injury of the flexible joints, often with symptoms of joint pain and swelling, stiffness, bone destruction and fatigue, as well as implications of extra articular organs. The prevalence of RA varies largely in different populations, from 0.25% in Eastern Asians to 0.75% in European ancestry, and to as high as 6% in American Indians. It remains largely unknown whether genetics, cultural, or environmental factors contribute to these differences. During the past years, an increasing list of genetic associations with RA has emerged from genome wide association studies (GWAS), which attributes great relevance to immune system contributed by profound sources of genetic variation with a panel of surface and intracellular signaling molecules as well as cytokines. GWAS has also revealed a complex picture of both shared and population-specific genetic susceptibility loci to this autoimmune disease in comparison of Asian and European populations. Generally, GWASs are designed to capture common genetic variation, and to date, a large portion of the heritability of complex traits has not been explained, which has prompted us to explore other potential sources of genetic susceptibility to RA, such as rare variants.

Accordingly, there remains a strong need for an improved method for identifying deleterious and/or pathogenic gene which may be involved in the progression, severity or reoccurrence of a disease, in particular an autoimmune disease highly related to genetic mutations.

SUMMARY OF THE INVENTION

The present invention provides a method of identifying a gene associated with a disease or pathological condition of the disease, comprising the steps of:

a) obtaining a first group of exome sequences from a first population of individuals and a second group of exome sequences from a second population of individuals, wherein the first population of individuals suffer from the disease or pathological condition of the disease, and the second population of individuals do not have the disease or pathological condition of the disease;

b) identifying one or more variants in the first group of exome sequences by comparing the first group of exome sequences with the second group of exome sequences, and optionally with a public database, to generate a first set of variant data;

c) applying a variant quality score calibration tool with a truth sensitivity threshold to remove false-positive variants having a sensitivity lower than the threshold and background variants from the first set of variant data so as to obtain a second set of variant data;

d) removing synonymous variants from the second set of variant data to obtain a third set of variant data; and e) identifying one or more deleterious variants from the third set of variant data using a gene burden analysis, optionally generating a fourth set of variant data.

The method of the present invention is exceptionally useful for the determination of deleterious and/or pathogenic gene and for further developments in diagnostic method and treatment methods of the diseases and alleviation of the pathological conditions of the disease. In particular, the method at least improves the genotype accuracy of the results, removes substantial errors resulting from the whole-exome sequencing, and differentiates the rare variants from the common variant efficiently.

Those skilled in the art will appreciate that the invention described herein is susceptible to variations and modifications other than those specifically described. The invention includes all such variations and modifications. The invention also includes all steps and features referred to or indicated in the specification, individually or collectively, and any and all combinations of the steps or features.

Other features and aspects of the invention will become apparent by consideration of the following detailed description and accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A shows the results obtained from Admixture analysis. All of the people in RA group and control group were found to be Chinese ancestry, i.e. having at least 80% (indicated by white horizontal line) Chinese ancestry. FIG. 1B shows Dimension 1 and 2 obtained from multidimensional scaling analysis for the RA and control groups.

FIG. 2A shows that the median coverage for all RA samples was 76-fold, with on average 96% of all targets covered at least 20-fold. FIG. 2B shows that the median coverage for all healthy control samples was 68-fold, with on average 94% of all targets covered at least 20-fold.

FIGS. 4A and 4B show the sequence alignment of target proteins. FIG. 4A refers to the SAA1 (Protein RefSeq: NP_000322.2; FIG. 4B refers to SCOT1 (Protein RefSeq: NP_000427.1), each with its template structures used in homolog modeling. Red line represents alpha helix, yellow arrow represents beta sheet, and blue line represents loop region.

FIG. 5A refers to the plot for SAA1, 99.03% of the residues are in the favored region and 0.97% are in the allowed region. FIG. 5B refers to the plot for SCOT1, 95.81% of the residues are in the favored region, 3.77% are in the allowed region and only 0.42% are in the disfavored region. Green represents favored region and light-brown represents allowed region.

FIGS. 6A, 6B, 6C, and 6D show the modeled 3D structure comparison of human wild type SAA1 (FIG. 6A) and its mutant G90D (FIG. 6B), as well as wild type SCOT1 (FIG. 6C) and its mutant T58M (FIG. 6D). Left panel: the ribbon secondary structure diagram with α helices in red and β sheets in yellow; middle panel: the proposed interactions between mutated residue and its surrounding residues, distances are not represented to scale; right panel: the lipophilic surface representation by showing hydrophilic (magenta), neutral (green) and lipophilic (white).

DETAILED DESCRIPTION OF THE EMBODIMENTS

Figure 1A:
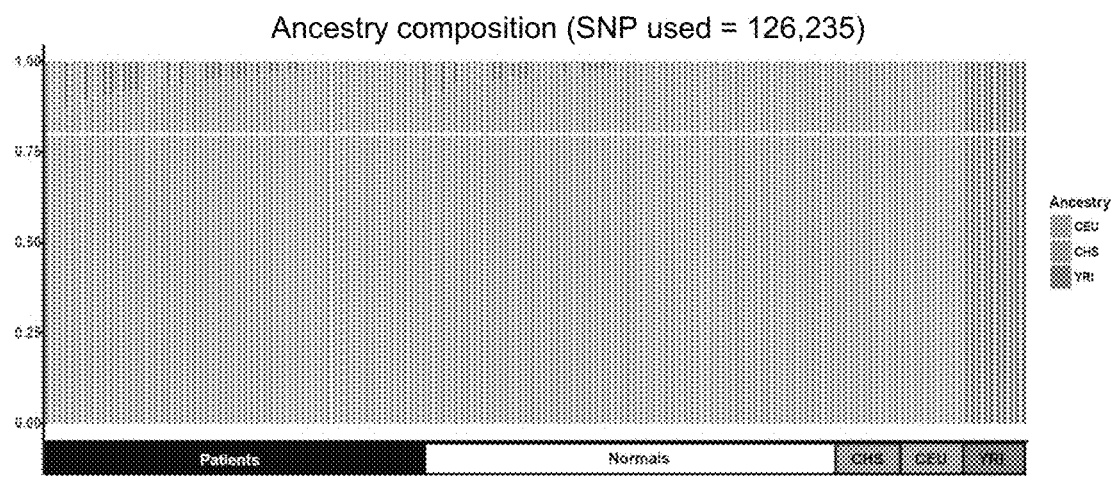
FIGS. 1A and 1B show the ancestral composition of RA group, i.e. patients suffering from RA, and control group, i.e. people who do not have RA, with Hapmap reference populations. Ten HapMap samples were randomly chosen from each of the three reference populations: CEU, Utah Residents with Northern and Western European Ancestry; CHS, Southern Han Chinese; and YRI, Yoruba in Ibadan, Nigeria.

Unless otherwise defined, all technical terms used herein have the same meaning as commonly understood by one skilled in the art to which the invention belongs.

As used herein, "comprising" means including the following elements but not excluding others. "Essentially consisting of" means that the material consists of the respective element along with usually and unavoidable impurities such as side products and components usually resulting from the respective preparation or method for obtaining the material such as traces of further components or solvents. "Consisting of" means that the material solely consists of, i.e. is formed by the respective element. As used herein, the forms "a," "an," and "the," are intended to include the singular and plural forms unless the context clearly indicates otherwise.

The present invention pertains to a method of identifying a gene associated with a disease or pathological condition of the disease. In particular, the disease is an autoimmune disease, a neurodegenerative disease, a cardiovascular disease, a cancer, a gastrointestinal disease, an inflammatory disease, or an endocrine disease. Preferably, the disease is an autoimmune disease. In an embodiment, the disease is rheumatoid arthritis. The expression "pathological condition of the disease" as used herein may refer to any symptoms closely related to the systemic effects of the disease which may be acute or chronic.

According to the present invention, the method comprises the steps of:

a) obtaining a first group of exome sequences from a first population of individuals and a second group of exome sequences from a second population of individuals, wherein the first population of individuals suffer from the disease or pathological condition of the disease, and the second population of individuals do not have the disease or pathological condition of the disease;

b) identifying one or more variants in the first group of exome sequences by comparing the first group of exome sequences with the second group of exome sequences, and optionally with a public database, to generate a first set of variant data;

c) applying a variant quality score calibration tool with a truth sensitivity threshold to remove false-positive variants having a sensitivity lower than the threshold and background variants from the first set of variant data so as to obtain a second set of variant data;

d) removing synonymous variants from the second set of variant data to obtain a third set of variant data; and e) identifying one or more deleterious variants from the third set of variant data using a gene burden analysis, optionally generating a fourth set of variant data.

The term "exome sequence" as used herein refers to a sequence consisting of all expressed genes in a genome, i.e. formed by exons that encode a part of the final mature RNA produced by the gene after introns have been removed by RNA splicing. In the present invention, the exome sequence of the individuals is preferably obtained through whole-exome sequencing.

An individual in the present invention is preferably a human or an animal, preferably the individual is a mammal. In an embodiment, the first population of individuals are preferably humans suffering from an autoimmune disease in particular rheumatoid arthritis and are diagnosed according to standard medical criteria. The second population of individuals are humans who do not have the disease, in particular the autoimmune disease, and do not have the associated pathological conditions of the disease. In an embodiment, each of the first and second population of individual has at least 10, 20, 30, 40, or 50 individuals, preferably at least 50 individuals. The first and second population may or may not have the same number of individuals.

The step a) of the method may comprise steps of collecting plasma samples from the first and second population of individuals, extracting the DNAs from the plasma samples and performing whole-exome sequencing (WES) to obtain the exome sequence of each of the individuals. Preferably, the first and second exome data are obtained by whole-exome sequencing. It is advantageous to use the WES in the present invention so as to focus on the mutation of gene and/or variant which contributes or likely contributes to the pathogenesis and/or progression of the disease. In particular, it saves lots of efforts and costs in preparing a whole genome and conducting the analysis of the lengthy genome. The person having ordinary skills in the art is aware of suitable methods for performing whole-exome sequencing.

In step b) of the method, one or more variants in the first group of exome sequences are identified. The term "variant" as used herein refers to a polynucleotide having a nucleotide sequence different from the reference polynucleotide, i.e. there is a change in the nucleotide sequence compared to the reference one. In this method, the second group of exome sequences act as the reference polynucleotide, optionally normal exome sequences annotated by public accessible database can also provide the reference polynucleotide for the comparison so as to locate and identify the one or more variants present in the first group of exome sequences, i.e. present in the individuals suffering from the disease or the pathological condition of the disease. After the identification, a first set of variant data is obtained and said set of variant data is presented in a computer-readable format. In an embodiment, the first set of variant data is further subject to electronic conversion of format, for instance for subsequent sequence alignment and/or for storage.

After obtaining the first set of variant data which shows the differences between the first group of exome sequences with the second group of exome sequences, a variant quality score calibration tool is applied, i.e. step c) of the method. In an embodiment, the step (c) comprises a step (i) of applying the variant quality score calibration tool with the truth sensitivity threshold of about 90% to remove the false-positive variants, and removing the background variants having a read depth of less than 5 and a genotype quality of less than 10 from the first set of variant data. "Variant quality score recalibration tool" (VQSC tool) is preferably applied to improve concordance of sequenced genotype, i.e. remove errors resultant from the whole-exome sequencing. In general, VQSC tool filters variants by using a recalibrated quality score and a sensitivity threshold. In an embodiment herein, the VQSC tool is applied with a truth sensitivity threshold of about 90%, preferably about 95%, more preferably about 99%, to remove the false-positive variants.

Also, the background variants having a read depth of less than 5, preferably less than 7.5, more preferably less than 10 and a genotype quality of less than 10, less than 15 or less than 20 are also removed from the first set of variant data. In an embodiment, the background variant having a read depth of less than 10 and a genotype quality of less than 20 are moved. These background variants refer to the variants which may significantly affect the detection of deleterious variants in the later steps and are likely generated by errors or not relevant to the disease. The term "depth of data" (DP) refers to the number of reads passing quality control used to calculate the genotype at a specific site in the sample. A higher value of DP generally denotes a more accurate genotype call. The term "genotype quality" (GQ) refers to a Phred-scaled value representing the confidence that the called genotype is the true genotype. A higher GQ generally denotes a more accurate genotype call. Therefore, by using the variant filtering process of step c), a more accurate set of variant data may be obtained.

In an advanced embodiment, the step c) of the method further comprises a step (ii) of screening the resultant variants from step c) (i) based on the dataset provided by UCSC genome browser, in particular based on UCSC genome browser build 37 human reference sequence gene annotation, to keep exonic or slicing variants in the second set of variant data. Alternatively, other accessible dataset showing the already identified variants in human genome may also be applied in combination to better analyze the variants.

Next, the second set of variant data is subject to a further variant filter to remove synonymous variants so as to obtain a third set of variant data. Synonymous variants are commonly regarded as benign in their effects towards diseases, in particular less likely to have any effect, and are generally not overexpressed in an individual suffering from a disease or pathological condition. This removal step may be conducted by computer-implemented program and/or in combination with database having annotation of the synonymous variants.

In the method of the present invention, a gene burden analysis is conducted to identify one or more deleterious variants from the third set of variant data obtained after step d). The term "deleterious variant" used herein refers to a variant which is consistently appear to cause all reasonable individuals to cause premature death or health problem, i.e. disease, that significantly compromise the capacity of the individual to carry out normal activities. In other words, the deleterious variant is highly related to the disease or pathological condition of the disease.

Preferably, the step e) comprises a step (i) of identifying one or more deleterious variants having a gene burden ratio of larger than 1, preferably larger than 1.2 or more preferably larger than 1.5, or being present in the first group of exome sequences in an amount of at least three but absent in the second group of exome sequences. The gene burden ratio is calculated by dividing the allele frequency in the first group of exome sequences by the allele frequency in the reference group, i.e. the second group of exome sequences and optionally an additional control group.

In a further embodiment, the step e) further comprises a step (ii) of grouping the identified one or more deleterious variants having a minor allele frequency less than or equal to about 0.02, preferably less than or equal to 0.015, less than or equal to 0.01, most preferably less than 0.01, into a rare variant group, and grouping the rest of the identified one or more deleterious variants into a common variant group. Minor allele frequency (MAF) generally refers to the frequency at which the second most common allele occurs in a given population. The identification of rare and common variants helps to investigate the genetic susceptibility of the individual to the disease.

The method may further comprises a step f), after step e), of determining a pathogenic gene associated with the disease or pathological condition of the disease from the fourth set of variant data by using a logistic regression model and public accessible database. The term "pathogenic gene" refers to a gene that contributes or likely contributes to the pathogenesis and progression of the disease.

In a further embodiment, the method further comprises a biological pathway analysis to determine the functional role of the identified one or more deleterious variants in the onset, progression, severity or recurrence of the disease. In particular, a structural analysis may be performed by using a homology model for 3D determination of the associated protein.

In order to improve the accuracy of the identification, the method further comprises a step of confirming the ethnicity of the first and second population of individuals via ancestry composition analysis.

Accordingly, the present invention provides an improved approach for the identification of deleterious and/or pathogenic variants involved in the disease onset, progression, severity or recurrence of a disease. The comprehensive method as disclosed herein at least improves the genotype accuracy of the results, removes substantial errors resulting from the whole-exome sequencing, and differentiates the rare variants from the common variant efficiently. The application of whole-exome sequencing also saves lots of efforts in preparing whole-genome which may contain substantial irrelevant genetic information of the disease, and of course less labor intensive.

The method of the present invention is exceptionally useful for the determination of deleterious and/or pathogenic gene for further developments in diagnostic method and treatment methods of the diseases and alleviation of the pathological conditions of the disease.

EXAMPLES

Example 1

Sample Collections

1. Patients 58 patients diagnosed as having RA were unrelated individuals of Han Chinese descent recruited from hospitals in Southern and Eastern China (Guangzhou and Changzhou) using 2010 Rheumatoid Arthritis Classification Criteria established by American College of Rheumatology and European League Against Rheumatism Collaborative Initiative (2010 ACR/EULAR).

In addition, 66 healthy and unrelated blood donors of Han Chinese ancestry from Medical Center for Physical Examination and Health Assessment, were included as controls.

Detailed descriptions of sequenced individuals and clinical characteristics of the enrolled patients are provided in Table 1 and 2. Written informed consent was obtained from all of the participants, and the study was registered in Chinese Clinical Trial Registry (ChiCTR-ROC-17010351) and approved by the local ethics committees of Macau University of Science and Technology (Macau, China).

TABLE 1

Basic information of the 124 sequenced individuals

| Parameter | Cases | Controls |
|---|---|---|
| n | 58 | 66 |
| Sex | 43 female, 15 male | 41 female, 25 male |
| Age | 48.48 ± 14.08 | 35.23 ± 10.73 |

TABLE 2

Demographic and clinical characteristics of the 58 patients with RA

| | |
|---|---|
| Women/men, no. (%) | 43 (74.1%)/15 (25.9%) |
| Age at diagnosis, mean ± SD years | |
| All | 45.17 ± 14.13 |
| Women | 43.67 ± 12.67 |
| Men | 49.47 ± 17.46 |
| Disease duration (years), mean ± SD | 3.31 ± 4.29 |
| ≤1 Year | 26 |
| ≥3 Year | 23 |
| Rheumatoid factor +/−, no. (%) | 49 (87.5%)/7 (12.5%); 2 Not Test |
| No. of tender joints, mean ± SD | 7.00 ± 7.36 |
| No. of swollen joints, mean ± SD | 3.43 ± 4.53 |
| CRP(mg/l) | 19.46 ± 22.62 |
| ESR(mm/h) | 40.38 ± 30.48 |

CRP: C-reactive protein; ESR: Erythrocyte Sedimentation Rate.

2. Confirmation of the Ethnicity of the RA and Control Groups

Figure 1B:
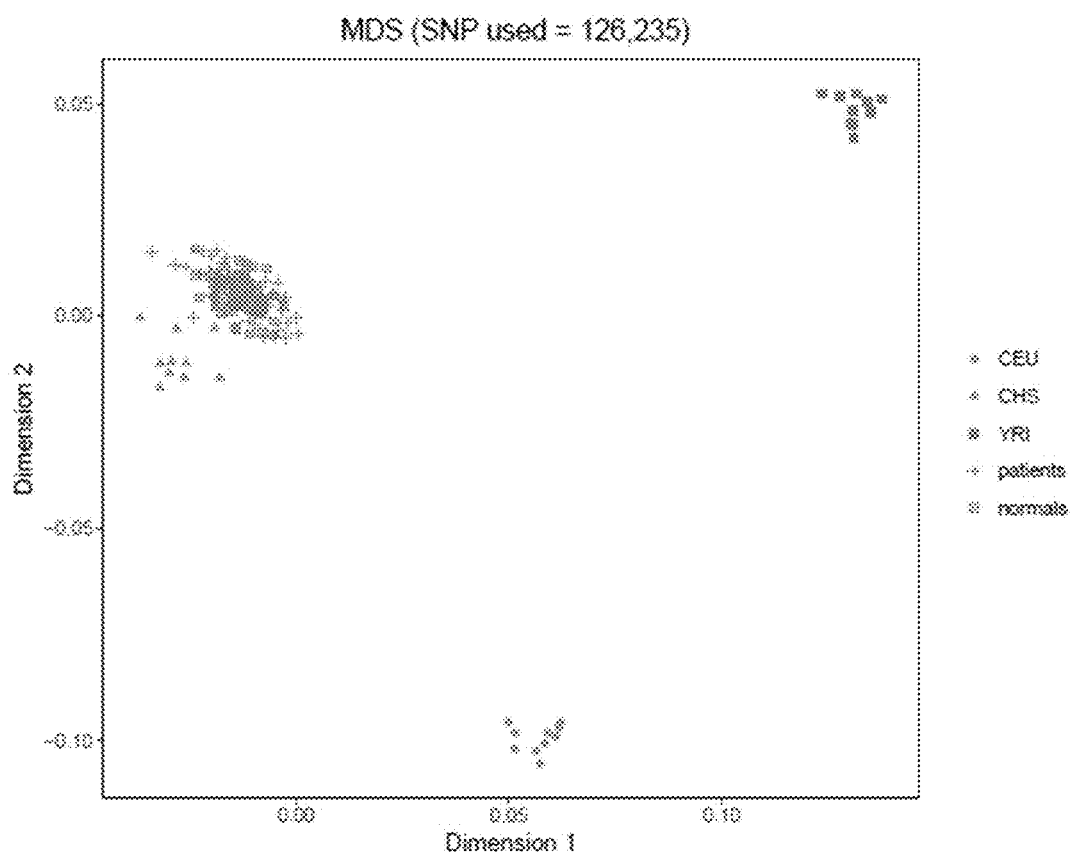

The ethnicity of the patients suffering from RA, i.e. RA group, and the healthy control group was verified by conducting ancestry composition analysis using admixture v1.3.0 (https://www.genetics.ucla.edu/software/admixture) and multidimensional scaling in PLINK v1.07 (http://zzz.bwh.harvard.edu//plink/). The results are shown in FIG. 1. Three ethnic populations were used as reference samples from 1000 Genome Project Phase III data (http://ftp.1000genomes.ebi.ac.uk/vol1/ftp/release/20130502/ALL.chr9.phase3_shapeit2_mvncall_integrated_v5a.20130502.genotypes.vcf.gz), including Utah Residents with Northern and Western European Ancestry (EUR-CEU), Yoruba in Ibadan, Nigeria (AFR-YRI) and Southern Han Chinese (EAS-CHS).

3. Preparation of the Samples for Gene Sequencing

Blood samples were collected from the patients of the RA group and the healthy people from the control group, according to protocols approved by local institutional review boards. Genomic DNA was extracted from peripheral blood mononuclear cells (PBMCs) using PureLink® Genomic DNA Mini Kit (Invitrogen, USA) according to the manufacturer's protocol. 500 ng of double-stranded DNA was determined by Qubit (Invitrogen, USA) and randomly fragmented to 150-200 bp with Covaris cracker (Covaris, USA). Fragments with specific indexes were hybridized with probes. After PCR amplification and quality control, libraries were sequenced by next-generation sequencing. Agilent liquid phase hybridization was applied to efficiently enrich whole exons which would be sequenced on Illumina platform. Agilent SureSelect Human All ExonV5/V6 (Agilent Technologies, USA) with reagents were used for sequencing libraries and capture, which was recommended by the instruction manual and followed by optimized experimental procedures.

Sequencing was performed on an Illumina HiSeq X sequencer with a paired-end read length of 150 bp in the Genomics Core Facility at Novogene (Genome Sequencing Company, Beijing, China). Data generated in this study will be submitted to the National Center for Biotechnology Information (NCBI) BioProject.

Example 2

Preparation of a List of Candidate Genes Associated with Rheumatoid Arthritis A list of 159 candidate RA-associated genetic variants reported by previous genome wide association studies (GWAS) with the P value threshold of $P<1\times10^{-5}$, as shown in Table 3, was prepared based on Rheumatoid Arthritis associated genes in the NHGRI GWAS Catalog (Welter D et al., Nucleic acids research 2014; 42:D1001-D1006) and literatures (Freudenberg J et al., Arthritis Rheumatol 2014; 66:1121-1132; Manolio T A et al., Nature 2009; 461:747-753; Okada Y et al., Nature 2014; 506:376-381; and Diogo D et al., The American Journal of Human Genetics 2013; 92:15-27).

TABLE 3

A list of candidate genes having high priority in RA

| Gene | SNP | p-Value | Odd ratio | References |
|---|---|---|---|---|
| ABHD6 | rs73081554 | 5.00E−08 | 1.18 | Okada Y, PMID: 24390342 |
| ACOXL | rs6732565 | 3.00E−08 | 1.07 | Okada Y, PMID: 24390342 |
| AFF3 | rs9653442\| | 1.00E−14\| | 1.12\|1.12\| | Okada Y, PMID: 24390342\|Stahl |
|  | rs11676922\| | 1.00E−14\| | 1.12 | E A, PMID: 20453842\|Jiang |
|  | rs10865035 | 2.00E−08\| |  | L, PMID: 24782177\|Stahl |
|  |  | 2.00E−06 |  | E A, PMID: 20453842 |

TABLE 3-continued

A list of candidate genes having high priority in RA

| Gene | SNP | p-Value | Odd ratio | References |
|---|---|---|---|---|
| AHNAK2 | rs2582532 | 3.00E-07 | 1.17 | Okada Y, PMID: 24390342 |
| AIRE | rs2075876\| rs760426 | 4.00E-09\| 4.40E-08 | 1.18\|1.16 | Terao C, PMID: 21505073\|Terao C, PMID: 21505073 |
| ANAPC4 | rs3816587 | 9.00E-06 | 1.09 | WTCCC, PMID: 17554300 |
| ANKRD55 | rs77331626\| rs7731626\| rs6859219 | 7.00E-24\| 8.00E-23\| 1.00E-11 | 1.21\|1.21\| 1.28 | Okada Y, PMID: 24390342\|Okada Y, PMID: 24390342\|Stahl E A, PMID: 20453842 |
| ANXA3 | rs2867461 | 1.00E-12 | 1.13 | Okada Y, PMID: 22446963 |
| APOM | rs805297 | 3.00E-10 | 1.56 | Hu H J, PMID: 21844665 |
| ARAP1 | rs3781913 | 6.00E-10 | 1.12 | Okada Y, PMID: 22446963 |
| ARHGEF3 | rs2062583 | 2.16E-06 | 0.63 | Freudenberg J, PMID: 21452313 |
| ARID5B | rs71508903\| rs71508903\| rs10821944 | 1.00E-08\| 1.00E-08\| 6.00E-18 | 1.18\|1.18\| 1.16 | Okada Y, PMID: 24390342\|Okada Y, PMID: 22446963 |
| ARL15 | rs255758 | 7.00E-06 | 1.42 | Negi S, PMID: 23918589 |
| ATG5 | rs9372120 | 4.00E-08 | 1.10 | Okada Y, PMID: 24390342 |
| ATM | chr11: 107967350 | 1.00E-08 | 1.21 | Okada Y, PMID: 24390342 |
| B3GNT2 | rs13385025\| rs11900673 | 9.00E-07\| 1.00E-08 | 1.11\|1.11 | Okada Y, PMID: 24390342\|Okada Y, PMID: 22446963 |
| BATF | rs7155603 | 1.00E-07 | 1.16 | Stahl E A, PMID: 20453842 |
| BLK | rs2736337\| rs1600249\| rs2736340 | 2.00E-07\| 5.00E-06\| 1.22E-05\| 6.00E-09 | 1.15\|0.77\| 1.29\|1.19 | Okada Y, PMID: 24390342\|Freudenberg J, PMID: 21452313\|Freudenberg J, PMID: 21452313\|Gregersen P K, PMID: 19503088 |
| BTNL2 | rs3763309 | 2.00E-124 | 2.30 | Orozco G, PMID: 24449572 |
| C1QBP | rs72634030 | 2.00E-09 | 1.12 | Okada Y, PMID: 24390342 |
| C4orf52 | rs11933540 | 1.00E-16 | 1.15 | Okada Y, PMID: 24390342 |
| C5 | rs10985070\| rs3761847\| rs881375 | 4.00E-09\| 2.00E-07\| 4.00E-08 | 1.09\|1.13\| NR | Okada Y, PMID: 24390342\|Stahl E A, PMID: 20453842\|Gregersen P K, PMID: 19503088 |
| C5orf30 | rs2561477\| rs26232 | 1.00E-10\| 4.00E-08 | 1.09\|1.14 | Okada Y, PMID: 24390342\|Stahl E A, PMID: 20453842 |
| C6orf10 | rs9275406 | 3.00E-12 | 2.10 | Negi S, PMID: 23918589 |
| CASP8 | rs6715284 | 2.00E-09 | 1.15 | Okada Y, PMID: 24390342 |
| CCL19 | rs11574914 | 2.00E-15 | 1.13 | Okada Y, PMID: 24390342 |
| CCL21 | rs951005\| rs2812378\| rs11574914 | 4.00E-10\| 3.00E-08\| 2.00E-15 | 1.19\|1.12\| 1.13 | Stahl E A, PMID: 20453842\|Raychaudhuri S, PMID: 18794853\|Okada Y, PMID: 24390342 |
| CCR6 | rs1571878\| rs3093023\| rs1854853\| rs3093024 | 1.00E-22\| 2.00E-11\| 4.00E-09\| 2.00E-10\| 8.00E-19 | 1.28\|1.13\| NR\|NR | Okada Y, PMID: 24390342\|Stahl E A, PMID: 20453842\|Jiang L, PMID: 24782177\|Jiang L, PMID: 24782177\|Kochi Y, PMID: 20453841 |
| CD2 | rs624988 | 8.00E-10 | 1.09 | Okada Y, PMID: 24390342 |
| CD226 | rs2469434 | 1.00E-08 | NR | Okada Y, PMID: 24390342 |
| CD244 | rs11265493\| rs3753389\| rs3766379\| rs1319651\| rs6682654 | 4.10E-07\| 8.00E-08\| 3.00E-08\| 6.40E-07\| 7.00E-08 | 1.28\|1.3\| 1.31\|1.28\| 1.31 | Suzuki A, PMID: 18794858\|Suzuki A, PMID: 18794858\|Suzuki A, PMID: 18794858\|Suzuki A, PMID: 18794858\|Suzuki A, PMID: 18794858 |
| CD247 | rs840016 | 2.00E-06 | 1.11 | Stahl E A, PMID: 20453842 |
| CD28 | rs1980422 | 2.00E-13 | 1.13 | Okada Y, PMID: 24390342 |
| CD40 | rs4239702\| rs4810485 | 1.00E-16\| 3.00E-09\| 8.00E-09 | 1.14\|0.85\| 1.15 | Okada Y, PMID: 24390342\|Stahl E A, PMID: 20453842\|Raychaudhuri S, PMID: 18794853 |
| CD5 | rs508970 | 3.00E-06 | 1.07 | Okada Y, PMID: 24390342 |
| CD83 | chr6: 14103212\| rs12529514 | 3.00E-06\| 2.00E-08 | 1.16\|1.14 | Okada Y, PMID: 24390342\|Okada Y, PMID: 22446963 |
| CDK2 | rs773125 | 1.00E-10 | 1.09 | Okada Y, PMID: 24390342 |
| CDK4 | rs1633360 | 1.00E-07 | 1.07 | Okada Y, PMID: 24390342 |
| CDK5RAP2 | rs12379034 | 1.00E-12 | 1.34 | Jiang L, PMID: 24782177 |
| CDK6 | rs4272\|rs42041 | 1.00E-08\| 4.00E-06 | 1.10\|1.11 | Okada Y, PMID: 24390342\|Raychaudhuri S, PMID: 18794853 |
| CEP57 | rs4409785 | 1.00E-11 | 1.12 | Okada Y, PMID: 24390342 |
| CFLAR | rs6715284 | 2.00E-09 | 1.15 | Okada Y, PMID: 24390342 |
| CLNK | rs13142500 | 2.00E-06 | 1.10 | Okada Y, PMID: 24390342 |
| CLYBL | rs9557321 | 6.00E-08 | 1.73 | Bossini-Castillo L, PMID: 24532677 |
| COG6 | rs9603616 | 2.00E-12 | 1.10 | Okada Y, PMID: 24390342 |

TABLE 3-continued

A list of candidate genes having high priority in RA

| Gene | SNP | p-Value | Odd ratio | References |
|---|---|---|---|---|
| CSF2 | rs657075\| | 6.00E−06\| | 1.12\|1.12 | Okada Y, PMID: |
|  | rs657075 | 3.00E−10 |  | 24390342\|Okada Y, PMID: 22446963 |
| CSF3 | chr17: 38031857 | 2.00E−12 | 1.09 | Okada Y, PMID: 24390342 |
| CTLA4 | rs3087243\| | 3.00E−25\| | 1.14\|1.15\| | Okada Y, PMID: 24390342\|Stahl |
|  | rs3087243\| | 1.00E−08\| | 1.09\|NR | E A, PMID: 20453842\|Doroth??e |
|  | rs231775\| | 6.30E−07\| |  | Diogo, PMID: 23261300\|Gregersen |
|  | rs231735 | 6.00E−09 |  | P K, PMID: 19503088 |
| CXCR5 | rs10790268 | 1.00E−15 | 1.14 | Okada Y, PMID: 24390342 |
| DNASE1L3 | rs73081554 | 5.00E−08 | 1.18 | Okada Y, PMID: 24390342 |
| DPP4 | rs12617656 | 1.00E−08 | 1.24 | Jiang L, PMID: 24782177 |
| EOMES | rs3806624 | 3.00E−08 | 1.08 | Okada Y, PMID: 24390342 |
| ETS1 | rs73013527\| | 1.00E−06\| | 1.08\|1.09 | Okada Y, PMID: |
|  | rs4937362 | 8.00E−07 |  | 24390342\|Okada Y, PMID: 22446963 |
| ETV7 | rs2234067 | 1.60E−09 | 1.15 | Okada Y, PMID: 24390342 |
| FADS1 | rs968567 | 2.00E−08 | 1.12 | Okada Y, PMID: 24390342 |
| FADS2 | rs968567 | 2.00E−08 | 1.12 | Okada Y, PMID: 24390342 |
| FADS3 | rs968567 | 2.00E−08 | 1.12 | Okada Y, PMID: 24390342 |
| FAM124A | rs3790022 | 1.00E−06 | 1.49 | Bossini-Castillo L, PMID: 24532677 |
| FCGR2A | rs72717009\| | 1.00E−07\| | 1.13\|1.10\| | Okada Y, PMID: |
|  | rs1801274\| | 2.40E−07\| | 1.14 | 24390342\|Doroth??e |
|  | rs11810143 | 1.80E−07 |  | Diogo, PMID: 23261300\|Doroth??e Diogo, PMID: 23261300 |
| FCRL3 | rs2317230 | 2.00E−07 | 1.07 | Okada Y, PMID: 24390342 |
| FLI1 | rs4937362 | 8.00E−07 | 1.09 | Okada Y, PMID: 22446963 |
| GATA3 | rs3824660 | 2.00E−08 | 1.08 | Okada Y, PMID: 24390342 |
| GATSL3 | rs1043099 | 7.00E−09 | 1.19 | Orozco G, PMID: 24449572 |
| GCH1 | rs3783637 | 2.00E−06 | 1.10 | Okada Y, PMID: 22446963 |
| GMCL1L | rs2961663 | 4.00E−06 | NR | Padyukov L, PMID: 21156761 |
| GPR125 | rs6448119 | 7.00E−06 | NR | Padyukov L, PMID: 21156761 |
| GRHL2 | rs678347 | 2.00E−08 | 1.08 | Okada Y, PMID: 24390342 |
| GRM5 | rs518167 | 2.00E−06 | 2.24 | Bossini-Castillo L, PMID: 24532677 |
| HLA | rs12194148\| | 5.00E−58\| | NR\|NR | Padyukov L, PMID: |
|  | rs2157337 | 9.00E−52 |  | 21156761\|Padyukov L, PMID: 21156761 |
| HLA-B | rs2596565 | 9.00E−09 | 1.40 | Bossini-Castillo L, PMID: 24532677 |
| HLA-DQA1 | rs9271348\| | 5.00E−07\| | 1.28\|NR\| | Bossini-Castillo L, PMID: |
|  | rs6457617\| | 1.00E−09\| | 2.10 | 24532677\|Julia A, PMID: |
|  | rs9275406 | 3.00E−12 |  | 18668548\|Negi S, PMID: 23918589 |
| HLA-DQA2 | rs12525220\| | 2.00E−13\| | 2.87\|NR\| | Jiang L, PMID: 24782177\|Julia |
|  | rs6457617\| | 1.00E−09\| | 2.10 | A, PMID: 18668548\|Negi |
|  | rs9275406 | 3.00E−12 |  | S, PMID: 23918589 |
| HLA-DQB1 | rs12525220\| | 2.00E−13\| | 2.87\|2.10 | Jiang L, PMID: 24782177\|Negi |
|  | rs9275406 | 3.00E−12 |  | S, PMID: 23918589 |
| HLA-DRB1 | rs9268839\| | 1.00E−250\| | 2.47\|2.47\| | Okada Y, PMID: |
|  | rs9268839\| | 1.00E−250\| | 2.88\|2.51\| | 24390342\|Okada Y, PMID: |
|  | rs6910071\| | 1.00E−299\| | NR\|3.62\| | 24390342\|Stahl E A, PMID: |
|  | rs7765379\| | 5.00E−23\| | 2.55\|NR\| | 20453842\|Freudenberg J, PMID: |
|  | rs13192471\| | 2.00E−58\| | 1.28 | 21452313\|Kochi Y, PMID: |
|  | rs660895\| | 1.00E−108\| |  | 20453841\|Plenge R M, PMID: |
|  | rs6457620\| | 4.00E−186\| |  | 17804836\|Raychaudhuri |
|  | rs615672\| | 8.00E−27\| |  | S, PMID: 18794853\|WTCCC, |
|  | rs9271348 | 5.00E−07 |  | PMID: 17554300\|Bossini-Castillo L, PMID: 24532677 |
| IFNGR2 | rs73194058 | 1.00E−06 | 1.08 | Okada Y, PMID: 24390342 |
| IGFBP1 | rs6956740 | 5.00E−07 | NR | Padyukov L, PMID: 21156761 |
| IKZF3 | chr17: 38031857\| | 2.00E−12\| | 1.09\|1.10 | Okada Y, PMID: 24390342\|Stahl |
|  | rs2872507 | 9.00E−07 |  | E A, PMID: 20453842 |
| IL2 | rs45475795\| | 4.00E−06\| | 1.14\|1.12 | Okada Y, PMID: 24390342\|Stahl |
|  | rs13119723 | 7.00E−07 |  | E A, PMID: 20453842 |
| IL20RB | rs9826828 | 9.00E−10 | 1.44 | Okada Y, PMID: 24390342 |
| IL21 | rs45475795\| | 4.00E−06\| | 1.14\|1.12 | Okada Y, PMID: 24390342\|Stahl |
|  | rs13119723 | 7.00E−07 |  | E A, PMID: 20453842 |
| IL2RA | rs706778\| | 5.00E−14\| | 1.10\|1.14\| | Okada Y, PMID: 24390342\|Stahl |
|  | rs706778\| | 1.00E−11\| | 1.25\|1.19 | E A, PMID: 20453842\|Doroth??e |
|  | rs2228150\| | 6.60E−07\| |  | Diogo, PMID: 23261300\|Orozco |
|  | rs2104286 | 1.00E−06 |  | G, PMID: 24449572 |
| IL2RB | rs3218251 | 6.00E−06 | 1.08 | Okada Y, PMID: 24390342 |
| IL3 | rs657075 | 6.00E−06 | 1.12 | Okada Y, PMID: 24390342 |
| IL6R | rs2228145 | 4.00E−09 | 1.08 | Okada Y, PMID: 24390342 |
| IL6ST | rs6859219 | 1.00E−11 | 1.28 | Stahl E A, PMID: 20453842 |

TABLE 3-continued

A list of candidate genes having high priority in RA

| Gene | SNP | p-Value | Odd ratio | References |
|---|---|---|---|---|
| INPP5B | rs28411352 | 3.00E−12 | 1.11 | Okada Y, PMID: 24390342 |
| intergenic | rs12413578 | 5.00E−08 | NR | Okada Y, PMID: 24390342 |
| IRAK1 | rs5987194 | 3.00E−12 | 1.16 | Okada Y, PMID: 24390342 |
| IRF4 | rs9378815 | 1.00E−07 | 1.09 | Okada Y, PMID: 24390342 |
| IRF5 | chr7: 128580042\|<br>rs10488631\|<br>rs3807306 | 1.00E−14\|<br>4.00E−11\|<br>3.00E−07 | 1.12\|1.19\|<br>1.44 | Okada Y, PMID: 24390342\|Stahl E A, PMID: 20453842\|Padyukov L, PMID: 21156761 |
| IRF8 | rs13330176\|<br>rs2280381 | 1.00E−12\|<br>2.00E−06 | 1.12\|1.12 | Okada Y, PMID: 24390342\|Okada Y, PMID: 22446963 |
| JAZF1 | rs67250450 | 3.00E−09 | 1.11 | Okada Y, PMID: 24390342 |
| KCNIP4 | rs6448119 | 7.00E−06 | NR | Padyukov L, PMID: 21156761 |
| KIF3 | rs17374222 | 2.00E−06 | 1.13 | Stahl E A, PMID: 20453842 |
| KIF5A | rs1678542\|<br>rs1678542 | 1.00E−07\|<br>9.00E−08 | 1.20\|1.12 | Orozco G, PMID: 24449572\|Raychaudhuri S, PMID: 18794853 |
| LBH | rs10175798 | 1.00E−09 | 1.08 | Okada Y, PMID: 24390342 |
| LOC100506023 | rs2105325 | 3.00E−11 | 1.12 | Okada Y, PMID: 24390342 |
| LOC100506403 | rs8133843 | 2.00E−08 | 1.09 | Okada Y, PMID: 24390342 |
| LOC145837 | rs8026898 | 4.00E−19 | 1.15 | Okada Y, PMID: 24390342 |
| LOC339442 | rs12140275 | 2.00E−09 | 1.11 | Okada Y, PMID: 24390342 |
| MED1 | rs1877030 | 2.00E−08 | 1.09 | Okada Y, PMID: 24390342 |
| MHC | rs7748270\|<br>rs6457617\|<br>rs12525220 | 1.00E−16\|<br>5.00E−75\|<br>2.00E−13 | 2.01\|2.36\|<br>2.87 | Jiang L, PMID: 24782177\|WTCCC, PMID: 17554300\|Jiang L, PMID: 24782177 |
| MICA | rs2596565 | 9.00E−09 | 1.40 | Bossini-Castillo L, PMID: 24532677 |
| MMEL1 | chr1: 2523811\|<br>rs3890745 | 5.00E−09\|<br>1.00E−07 | 1.10\|1.12 | Okada Y, PMID: 24390342\|Raychaudhuri S, PMID: 18794853 |
| MTF1 | rs28411352 | 3.00E−12 | 1.11 | Okada Y, PMID: 24390342 |
| NFKBIE | rs2233424\|<br>rs2233434 | 1.00E−19\|<br>6.00E−19\|<br>1.00E−15 | 1.26\|1.19 | Okada Y, PMID: 24390342\|Okada Y, PMID: 22446963\|Myouzen K, PMID: 23028356 |
| OLIG3 | rs2230926\|<br>rs6920220\|<br>rs10499194 | 2.00E−06\|<br>1.00E−07\|<br>1.00E−09 | 1.31\|1.22\|<br>1.33 | Kochi Y, PMID: 20453841EA\|Plenge R M, PMID: 17982456\|Plenge R M, PMID: 17982456 |
| P2RY10 | chrX: 78464616 | 4.00E−08 | 1.11 | Okada Y, PMID: 24390342 |
| PADI4 | rs2301888\|<br>rs2240335 | 1.00E−18\|<br>2.00E−08 | 1.13\|1.50 | Okada Y, PMID: 24390342\|Freudenberg J, PMID: 21452313 |
| PDE2A | rs3781913 | 6.00E−10 | 1.12 | Okada Y, PMID: 22446963 |
| PIP4K2C | rs1678542 | 9.00E−08 | 1.12 | Raychaudhuri S, PMID: 18794853 |
| PLCL2 | rs4452313 | 2.00E−10 | NR | Okada Y, PMID: 24390342 |
| PLD4 | rs2582532\|<br>rs2841277 | 3.00E−07\|<br>2.00E−14 | 1.17\|1.15 | Okada Y, PMID: 24390342\|Okada Y, PMID: 22446963 |
| POU3F1 | rs12131057 | 4.00E−07 | 1.16 | Stahl E A, PMID: 20453842 |
| PPIL4 | rs9373594 | 3.00E−09 | 1.09 | Okada Y, PMID: 24390342 |
| PRKCB1 | rs7404928 | 4.00E−06 | 1.08 | Okada Y, PMID: 22446963 |
| PRKCH | rs3783782\|<br>rs1957895 | 2.00E−09\|<br>4.00E−07 | 1.14\|1.09 | Okada Y, PMID: 24390342\|Okada Y, PMID: 22446963 |
| PRKCQ | rs947474\|<br>rs4750316 | 3.00E−10\|<br>2.00E−06\|<br>4.00E−06 | 1.12\|1.15\|<br>1.14 | Okada Y, PMID: 24390342\|Stahl E A, PMID: 20453842\|Raychaudhuri S, PMID: 18794853 |
| PTPN11 | rs10774624 | 7.00E−09 | 1.09 | Okada Y, PMID: 24390342 |
| PTPN2 | rs8083786\|<br>rs2847297 | 2.00E−11\|<br>2.00E−08 | 1.18\|1.10 | Okada Y, PMID: 24390342\|Okada Y, PMID: 22446963 |
| PTPN22 | rs2476601\|<br>rs2476601\|<br>rs6679677 | 9.00E−170\|<br>9.00E−74\|0\|<br>1.00E−08\|<br>6.00E−42\|<br>6.00E−25 | 1.80\|1.94\|<br>1.82\|1.79\|<br>1.98 | Okada Y, PMID: 24390342\|Stahl E A, PMID: 20453842\|Doroth??e Diogo, PMID: 23261300\|Padyukov L, PMID: 21156761\|Raychaudhuri S, PMID: 18794853\|WTCCC, PMID: 17554300 |
| PVT1 | rs1516971 | 1.00E−10 | 1.15 | Okada Y, PMID: 24390342 |
| PXK | rs73081554\|<br>rs13315591 | 5.00E−08\|<br>5.00E−08 | 1.18\|1.29 | Okada Y, PMID: 24390342\|Stahl E A, PMID: 20453842 |
| RAD51B | rs1950897 | 5.00E−08 | 1.09 | Okada Y, PMID: 24390342 |
| RAG1 | rs331463 | 1.00E−07 | 1.12 | Okada Y, PMID: 24390342 |
| RAG2 | rs331463 | 1.00E−07 | 1.12 | Okada Y, PMID: 24390342 |

TABLE 3-continued

A list of candidate genes having high priority in RA

| Gene | SNP | p-Value | Odd ratio | References |
|---|---|---|---|---|
| RASGRP1 | rs8032939 | 2.00E−18 | 1.13 | Okada Y, PMID: 24390342 |
| RBPJ | rs874040| | 1.00E−16| | 1.14|1.19 | Stahl E A, PMID: |
|  | rs6448432 | 4.00E−07 |  | 20453842|Orozco G, PMID: |
|  |  |  |  | 24449572 |
| RCAN1 | chr21: 35928240 | 3.00E−07 | 1.11 | Okada Y, PMID: 24390342 |
| REL | rs34695944| | 2.00E−15| | 1.12|1.13| | Okada Y, PMID: 24390342|Stahl |
|  | rs13031237| | 8.00E−07| | NR | E A, PMID: 20453842|Gregersen |
|  | rs13017599 | 2.00E−12 |  | P K, PMID: 19503088 |
| RNASEH2B | rs3790022 | 1.00E−06 | 1.4925 | Bossini-Castillo L, PMID: |
|  |  |  |  | 24532677 |
| RPS12P4 | rs4305317 | 2.00E−06 | 1.45 | Padyukov L, PMID: 21156761 |
| RTKN2 | rs6479800| | 4.00E−06| | 1.19|NR | Okada Y, PMID: |
|  | rs3125734 | 5.00E−09 |  | 24390342|Myouzen K, |
|  |  |  |  | PMID: |
|  |  |  |  | 23028356 |
| RUNX1 | rs8133843 | 2.00E−08 | 1.09 | Okada Y, PMID: 24390342 |
| SALL3 | rs2002842 | 6.00E−06 | 1.61 | Julia A, PMID: 18668548 |
| SFTPD | rs726288 | 9.00E−09 | 1.22 | Okada Y, PMID: 24390342 |
| SH2B3 | rs10774624| | 7.00E−09| | 1.09|1.08 | Okada Y, PMID: 24390342|Stahl |
|  | rs3184504 | 6.00E−06 |  | E A, PMID: 20453842 |
| SMIM21 | rs1943199 | 2.00E−08 | 1.94 | Bossini-Castillo L, PMID: |
|  |  |  |  | 24532677 |
| SPRED2 | rs1858037| | 1.00E−08| | 1.19|1.13 | Okada Y, PMID: 24390342|Stahl |
|  | rs934734 | 5.00E−10| |  | E A, PMID: 20453842|Jiang |
|  |  | 2.00E−08 |  | L, PMID: 24782177 |
| STAT4 | rs11889341| | 1.00E−12| | 1.12|1.16 | Okada Y, PMID: 24390342|Stahl |
|  | rs7574865 | 3.00E−07| |  | E A, PMID: 20453842|Kochi |
|  |  | 2.00E−06 |  | Y, PMID: 20453841 |
| SYNGR1 | rs909685 | 1.00E−16 | 1.13 | Okada Y, PMID: 24390342 |
| TAGAP | rs2451258 | 2.00E−10 | 1.10 | Okada Y, PMID: 24390342 |
| TEC | rs2664035 | 1.00E−07 | 1.07 | Okada Y, PMID: 24390342 |
| TNFAIP3 | rs7752903| | 2.00E−20| | 1.41|1.22| | Okada Y, PMID: 24390342|Stahl |
|  | rs6920220| | 9.00E−13| | 1.38|1.33 | E A, PMID: 20453842|Plenge |
|  | rs2230926| | 1.00E−07| |  | R M, PMID: 17982456|Doroth??e |
|  | rs10499194 | 6.80E−14| |  | Diogo, PMID: 23261300|Kochi |
|  |  | 2.00E−06| |  | Y, PMID: 20453841|Plenge |
|  |  | 1.00E−09 |  | R M, PMID: 17982456 |
| TNFRSF14 | chr1: 2523811| | 5.00E−09| | 1.10|1.12| | Okada Y, PMID: 24390342|Stahl |
|  | rs3890745 | 4.00E−06| | NR|1.12 | E A, PMID: 20453842|Orozco |
|  |  | 1.00E−06| |  | G, PMID: |
|  |  | 1.00E−07 |  | 24449572|Raychaudhuri |
|  |  |  |  | S, PMID: 18794853 |
| TNFRSF9 | rs227163 | 3.00E−09 | 1.11 | Okada Y, PMID: 24390342 |
| TPD52 | rs998731 | 2.00E−08 | 1.08 | Okada Y, PMID: 24390342 |
| TRAF1 | rs10985070| | 4.00E−09| | 1.09|1.13| | Okada Y, PMID: 24390342|Stahl |
|  | rs3761847| | 2.00E−07| | 1.10|NR|NR | E A, PMID: 20453842|Doroth??e |
|  | rs2239657| | 5.40E−08| |  | Diogo, PMID:23261300|Gregersen |
|  | rs881375| | 4.00E−08| |  | P K, PMID: 19503088|Jiang |
|  | rs2072438 | 3.00E−09 |  | L, PMID: 24782177 |
| TRAF1-C5 | rs3761847 | 4.00E−14 | 1.32 | Plenge R M, PMID: 17804836 |
| TRAF6 | rs331463 | 1.00E−07 | 1.12 | Okada Y, PMID: 24390342 |
| TRHDE | rs12831974 | 6.00E−06 | 1.27 | Freudenberg J, PMID: 21452313 |
| TXNDC11 | rs4780401 | 4.00E−08 | 1.07 | Okada Y, PMID: 24390342 |
| TYK2 | rs34536443 | 5.00E−16 | 1.46 | Okada Y, PMID: 24390342 |
| UBASH3A | rs1893592| | 7.00E−12| | 1.11|1.11 | Okada Y, PMID: 24390342|Stahl |
|  | rs11203203 | 4.00E−06 |  | E A, PMID: 20453842 |
| UBE2L3 | rs11089637 | 2.00E−07 | 1.10 | Okada Y, PMID: 24390342 |
| WDFY4 | rs2671692 | 3.00E−09 | 1.07 | Okada Y, PMID: 24390342 |
| YDJC | rs11089637 | 2.00E−07 | 1.10 | Okada Y, PMID: 24390342 |
| ZNF438 | rs793108 | 1.00E−09 | 1.08 | Okada Y, PMID: 24390342 |
| ZNF774 | rs6496667 | 1.00E−06 | 1.09 | Okada Y, PMID: 22446963 |

Example 3

Analysis of the Whole-Exome Sequencing (WES)

To analyze the entire cohort of samples for genotype calls, variant analysis and joint genotyping were performed according to the pipeline recommended by the Genome Analysis Toolkit software and the GATK Best Practices procedures on RA patients and healthy controls (San Lucas F A et al., Bioinformatics 2012; 28:421-422; and Dong C et al., Human molecular genetics 2015; 24:2125-2137). Briefly, Burrows-Wheeler Aligner (BWA) software was utilized to align the raw sequencing reads in FASTQ formats to the 1000 Genomes (GRCh37+decoy) human genome reference. The BWA alignment files were converted to BAM files with SAMtools v1.1, which was used for sorting the BAM files. Duplicate reads were marked for BAM files with Picard MarkDuplicates (https://sourceforge.net/projects/picard/). The coverage and depth were computed based on the final BAM file. Local realignment, base quality recalibration, variant calling, joint genotyping, and variant quality score recalibration and filtration were applied using with GATK v3.7 (https://software.broadinstitute.org/gatk/). Default settings were used for BWA, SAMtools, Picard and GATK tools.

Further filtration for the joint genotyped variants was performed using Variant Tools (San Lucas F A et al., Bioinformatics 2012; 28:421-422). The inventors applied the following filters to generate a list of preliminary variants by removing false-positive variants through Variant Quality Score Recalibration with tranche truth sensitivity threshold <99.00, as well as variants with low read depth (DP)<10 and poor genotyping quality (GQ)<20, keeping exonic or splicing variants based on University of California, Santa Cruz (UCSC) genome browser build 37 human Reference Sequence Gene annotation, and removing synonymous variants.

From the preliminary variant list, variants annotated as "pathogenic" in ClinVar and deleterious variants were identified, respectively, including those candidate genes that overlapped with previous studies or passed the case-control gene burden test threshold. Deleterious variants were predicted to be damaging (disease-related, D) or benign/neutral (tolerated, T) based on LR score determined by logistic regression (LR) model (Dong C et al., Human molecular genetics 2015; 24:2125-2137). The novel deleterious variants were divided into the rare and common variant groups, which were distinguished by minor allele frequency (MAF) in Chinese Southern population from the 1000 Genomes Project phase III study.

Example 4

Analysis of Burden Association Signal

Case-control gene burden analysis was assessed on both rare and common deleterious variants to investigate causal genes using RA patients with >80% Chinese ancestry as cases and two types of controls: 105 southern Chinese samples from the 1000 Genomes Project phase III study and 66 healthy controls with >80% Chinese ancestry. Regardless of DP or GQ, all available genotype calls contributed to the number of allele count across the retained deleterious variants in each individual gene. The gene burden ratio was calculated by dividing the allele frequency in cases by the allele frequency in controls. We identified an enrichment of deleterious variants in a gene according to the gene burden ratio >1.5-fold with both types of controls, or the deleterious alleles in the gene with at least 3 RA cases if zero allele frequency in the controls. The inventors further identified genes with rare variants that were homozygous in RA cases but not present in controls, which were considered greater contribution to functional impact.

Example 5

Pathway Analysis

To discover enriched functional-related gene groups, pathway analysis was performed using DAVID Bioinformatics Resource 6.8 program (DAVID 6.8) (https://david.ncifcrf.gov/summary.jsp) with a Modified Fisher Exact P value less than 0.05 as the significance threshold and strong enrichment in the annotation categories.

Homology modeling is one of the best and reliable ways to construct the three dimensional (3D) structure of protein (Yamaguchi H et al., European journal of medicinal chemistry 2011; 46:1325-1330). Firstly, protein sequence was imported into the Molecular Operating Environment (MOE) 2015.09 software (Chemical Computing Group Inc., Montreal, Canada) to search an optimal template. The top ranked structure based on the Z score towards the target sequence was selected as the template. Target protein sequence and its corresponding crystal structure coordinates of template were separately loaded and aligned. A series of protein models were independently constructed by using a Boltzmann-weighted randomized procedure (Levitt M., Journal of molecular biology 1992; 226:507-533). Amber force field was applied in the process of construction and energy minimization (Case D et al., Amber 12 reference manual). Finally, the model with the best packing quality function was selected for further full energy minimization, and the stereochemical qualities of protein model was assessed by means of Ramachandran plots.

To analyze the effect on the point mutation in the 3D structure of the protein, the mutant protein were carried out in Residue Scan module of MOE 2015.09 software based on the 3D structure of homology modeling. In addition, we further analyze the hydrogen bonds, solvent interactions, metal ligation and non-bonded interaction between the target mutant residue and its surrounding key amino acid residues.

Example 6

Results

1. Deleterious Variants in Novel RA Candidate Genes

Figure 2A:
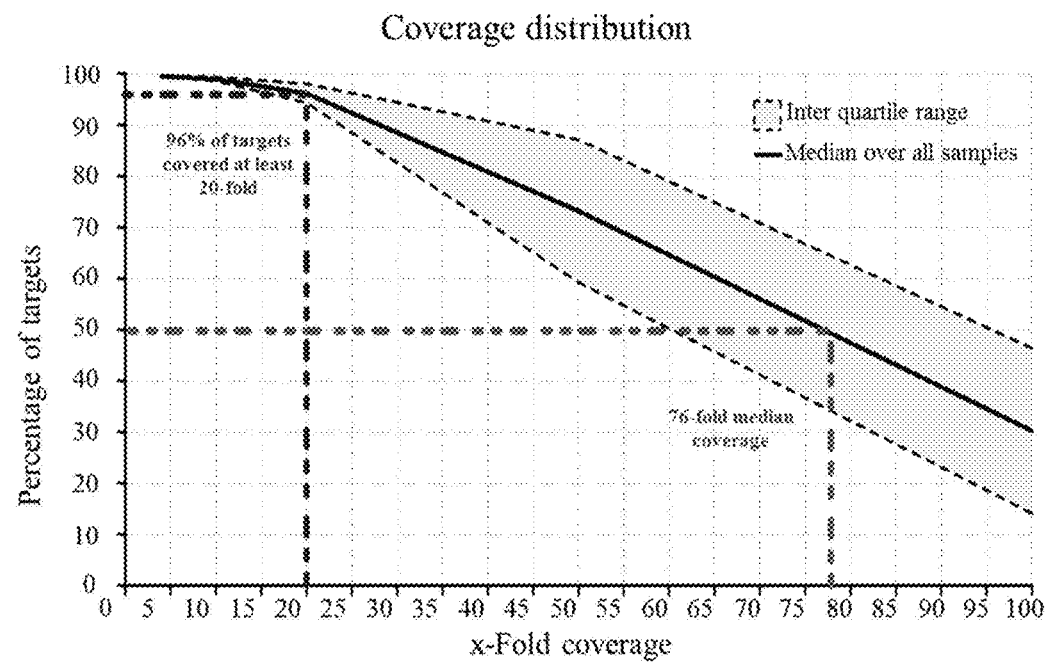
FIGS. 2A and 2B show the coverage distribution for all exons targeted by enrichment evaluated by inter-quartile range calculation using SPSS 22.0 software.
Figure 2B:
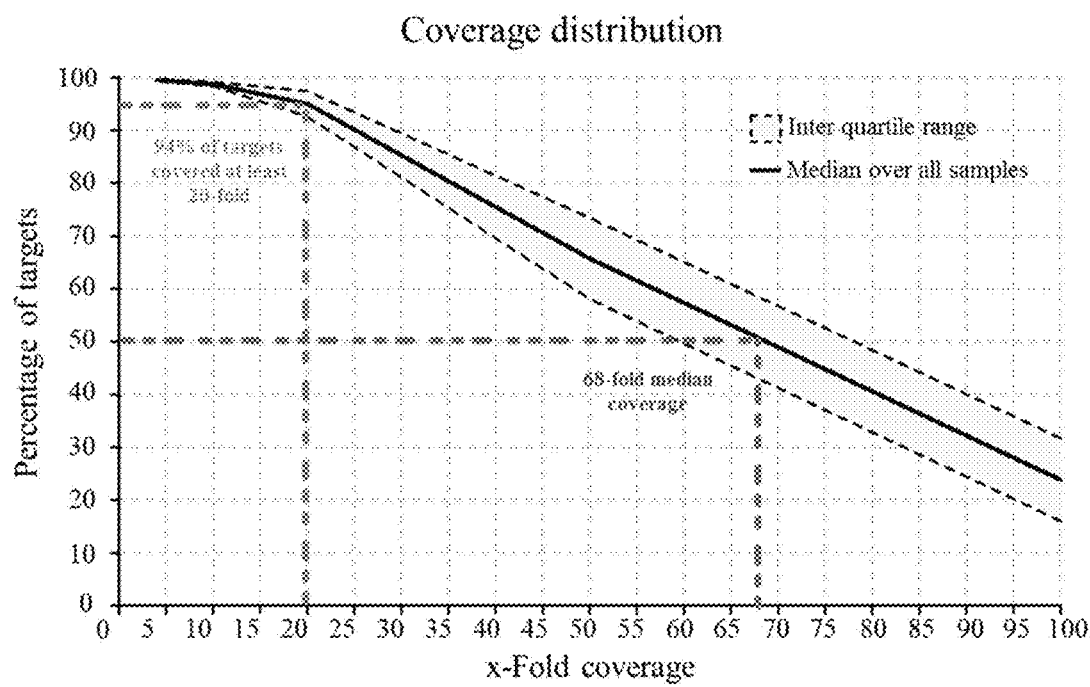

WES data were generated from 58 RA patients with a median coverage of 76-fold on targeted exome regions (FIG. 2A). An average of 96% of all targeted regions was covered by at least 20-fold. The healthy control group had a median coverage of 68-fold on targeted exome regions, and an average of 94% of those regions was covered by at least 20-fold (FIG. 2B).

Figure 3:
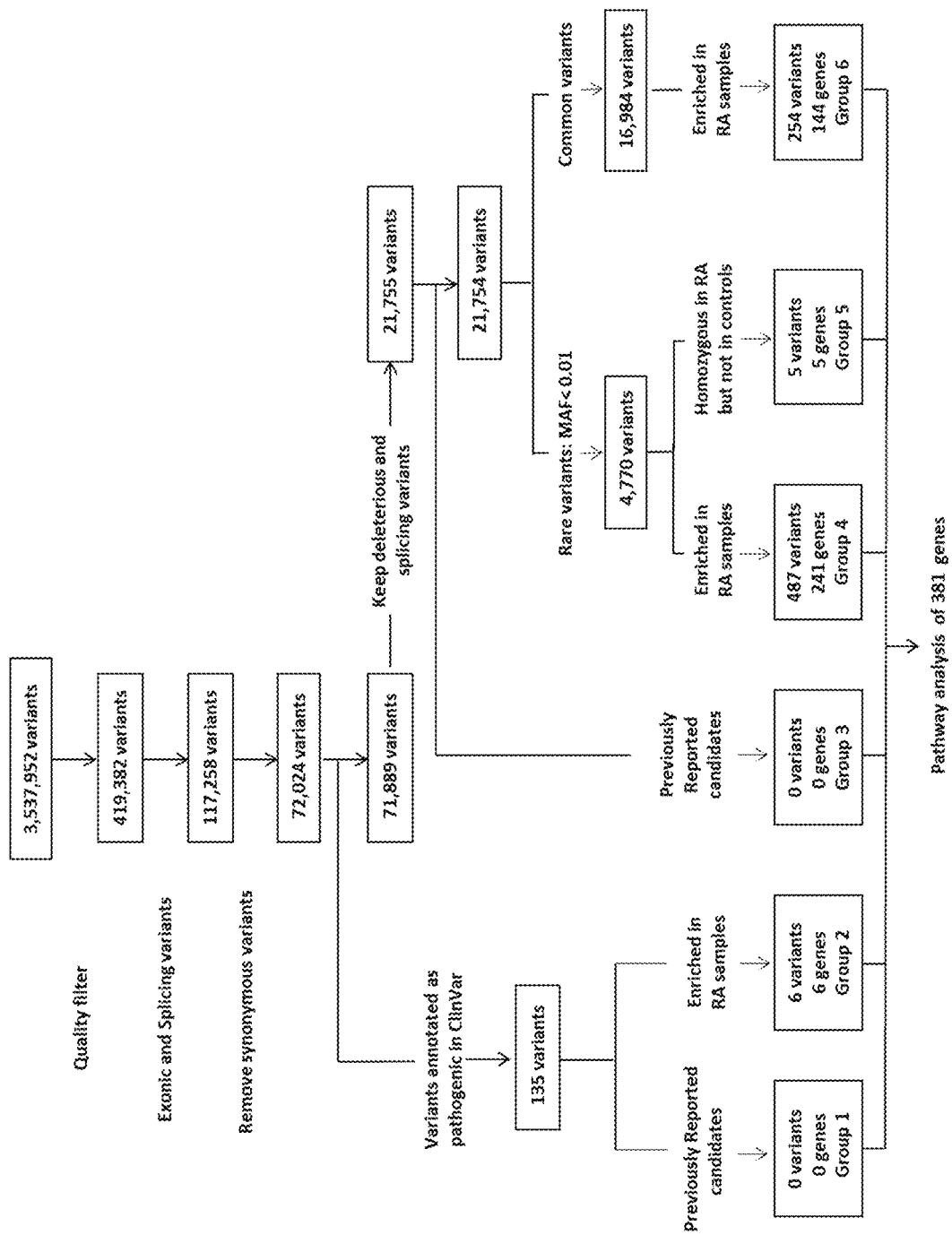
FIG. 3 is a flow chart of whole-exome sequencing for detecting and prioritizing variants conferring susceptibility to rheumatoid arthritis (RA) using variant filtration and gene burden analysis. The variant list for all groups can be found in Table 5. MAF=minor allele frequency in the 1000 Genomes Southern Han Chinese (phase III) population. Pathway analysis in candidate genes identified from 58 RA patients was performed using DAVID 6.8 (https://david.ncifcrf.gov/summary.jsp).

As shown in the flow chart of FIG. 3, a total of 3,537,952 variants were identified from 58 RA samples. After applying the quality filters and removing synonymous variants, we found 72,024 exonic and splicing variants, including nonsynonymous substitutions and a small number of stop-gain, stop-loss, frameshift and non-frameshift indels (Table 4). Of these, 135 variants were identified as deleterious based on the "pathogenic" annotation in ClinVar, and an additional 21,755 variants predicted to be deleterious were identified using an ensemble logistic regression score.

TABLE 4

Types of exonic, splicing and nonsynonymous variants (total = 72,024).

| Mutation type | | No. of variants |
|---|---|---|
| Nonsynonymous SNV | | 56,466 |
| Stop-gain | | 828 |
| Stop-loss | | 49 |
| Frameshift | Deletion | 408 |
| | Insertion | 215 |
| Nonframeshift | Deletion | 705 |
| | Insertion | 466 |
| Splicing | | 11,377 |
| Unknown | | 1510 |

It was surprising that the identified genes were not found in previously reported candidate risk variants GWAS data (group 1 and group 3 in FIG. 3; Table 5 and 6), such as HLA-associated genes. After reviewing the location of the reported RA-associated variants, the inventors found that only 9 of over 200 variants are located in the exome area, including CTLA4 (rs231775), FCGR2A (rs1801274), IL6R (rs2228145), OLIG3 (rs2230926), PTPN22 (rs2476601), RTKN2 (rs3125734), SH2B3 (rs3184504), TNFAIP3 (rs223092) and TYK2 (rs34536443). Since the inventors applied WES technique to focus on exome regions, the results are different from the previously reported studies. It is advantageous that the presently disclosed method of identification of RA associated genes is capable of providing more comprehensive information of RA associated genes. According to the results, a number of new RA associated genes have now been identified and may be useful in developing advanced methods for diagnosis and treatment of RA.

Interestingly, two novel risk variant loci were identified associated with TGFβ1 (transforming growth factor β1) and FOXP3 (forkhead box P3) genes (group 4 and group 6 in FIG. 3; Table 5) whereas other known variations of these two genes were previously found to be involved in the risk to RA (Zhou T B et al., J Recept Signal Transduct Res 2014; 34:469-475; and Paradowska-Gorycka A et al., J Rheumatol 2015; 42:170-180).

In order to identify novel genes and pathways that could enhance understanding of RA pathogenesis, the inventors performed a gene burden analysis to identify genes for which deleterious variants were enriched in the Han Chinese RA samples compared to healthy control and public control samples. Six such genes were identified (group 2 in FIG. 3; Table 5 and 7). Of these, a missense variant of SAA1 (Serum Amyloid A1) was found in 3 RA patients but not present in healthy controls. SAA1 is highly expressed in response to inflammation and tissue injury, and strongly associated with activity of the disease and risk of cardiovascular and renal involvement in RA patients, suggesting that this novel deleterious variant may potentially contribute to RA disease risk through its interference with pro-inflammatory effectors. Additional pathogenic variant of OXCT1 (3-Oxoacid CoA-Transferase 1) was predicted to be damaging (disease-related, D) in the RA patients, encoding Succinyl-CoA:3-ketoacid coenzyme A transferase 1 (SCOT1), which is a key enzyme for synthesis and degradation of ketone bodies involved in cardiovascular disease.

Rare variants are more likely to predict a significant impact on protein function and result in clinically relevant consequences than common ones. Thus, the inventors grouped variants that were indicated to be deleterious into rare (minor allele frequency <1%) and common variants, which did not overlap with previously reported candidates (Table 5). Performing a gene burden analysis for variants within each of these groups, we identified 241 genes (group 4 in FIG. 3; Table 5) with rare, deleterious variants specifically enriched in our Chinese RA samples compared to healthy control and public control samples. Notably, since the functional impact of rare and deleterious variants is likely to be greater when present as homozygote, 5 rare and deleterious homozygous variants (NCR3LG1, RAP1GAP, CHCHD5, HIPK2 and DIAPH2) were identified in the Chinese RA samples and absent in the controls (group 5 in FIG. 3; Table 3). Finally, we also identified 144 genes with common and deleterious variants in RA patients (group 6 in FIG. 3; Table 5).

2. Pathway Analysis

Using the method as disclosed herein, the inventors identified a total of 381 genes as candidates for increased risk of RA (Table 5). In order to further identify the associated biologic pathways, the inventors performed the functional enrichment analysis using DAVID 6.8 and identified the pathways of the extracellular matrix (ECM)-receptor interaction, protein digestion and absorption, focal adhesion and glycerophospholipid metabolism as significantly overrepresented (Table 8), which were reported to be relevant in pathogenesis of arthritis (Lv W et al., Mol Biosyst 2015; 11:2986-2997; and Choe J Y et al., Rheumatology (Oxford) 2016; 55:928-938).

In order to identify variants that might predispose RA patients to disease duration, the inventors repeated the variant filtration and gene burden analysis on Chinese RA samples with the disease duration 3-year compared to the disease duration ≤1-year. A total of 277 genes were identified (Table 9) compared to the 381 genes identified in the case-control comparison (Table 5). Of these, 87 genes were unique to disease duration with exonic variants (Table 10). Pathway analysis performed on the 87 genes identified olfactory transduction pathway as significantly overrepresented (Table 8), including OR14C36, OR4A15, OR52N4, OR6C74, OR6C75, OR7G3 and OR9K2.

3. Structural Analysis and Function Change Prediction of Potential Biomarkers

Figure 5B:
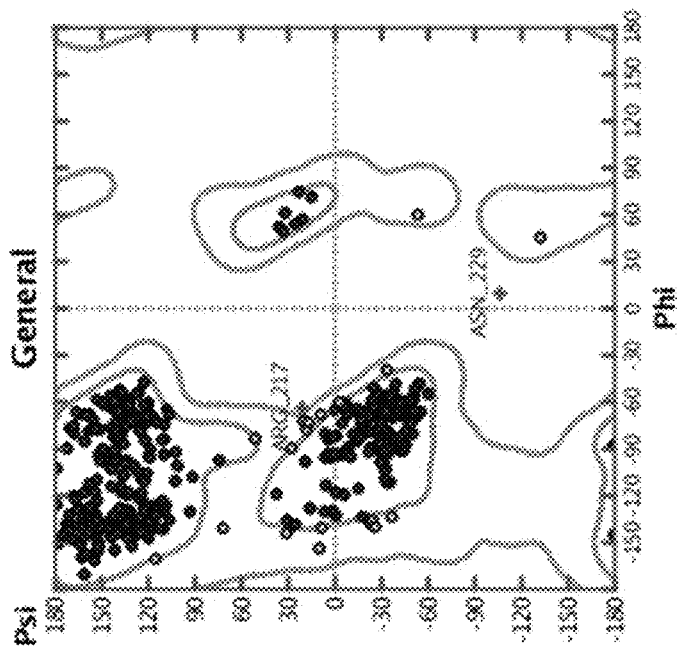
FIGS. 5A and 5B show Ramachandran plots for evaluation of protein model.
Figure 5A:
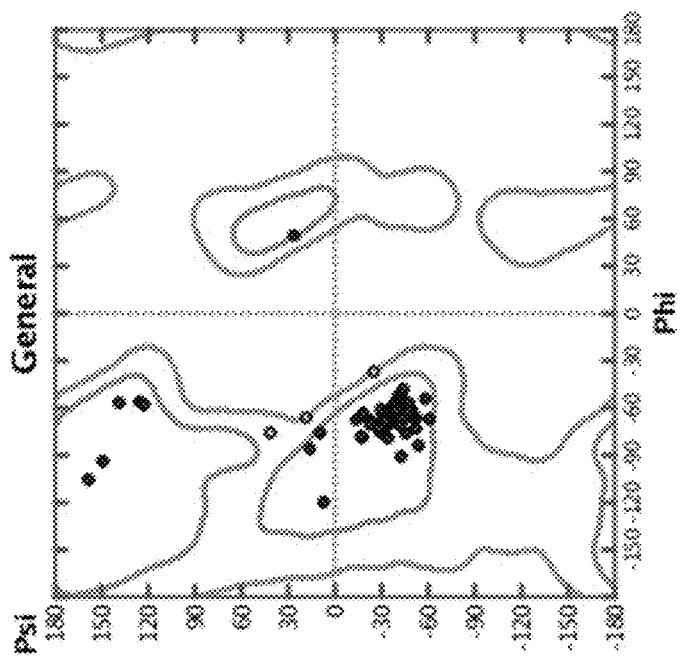

In order to gain structure insights of the potential biomarkers with pathogenic variants into the clinical conditions of RA patients, the inventors derived a three-dimensionally structure model of SAA1 Gly90Asp (rs79681911) and SCOT1 Thr58Met (rs75134564) by combining homology modeling with point mutation in MOE 2015.09 package. The crystal structures of human SAA1 protein (PDB code: 4IP8.A) and SCOT1 protein (PDB code: 3K6M.C) were selected to be used as templates due to their optimal identity with the target sequences of SAA1 (Protein RefSeq: NP_000322.2) and SCOT1 (Protein RefSeq: NP_000427.1), 83.6% and 83.5%, respectively (FIG. 4). The SAA1 and SCOT1 models with the best packing quality function and full energy minimization were assessed by Ramachandran plots, indicating that the phi and psi backbone dihedral angles in the models were reasonable (FIG. 5).

Structural analysis of SAA1 Gly90Asp (FIGS. 6A and 6B) revealed that the substitution of glycine with aspartic acid induced the formation of two pairs of hydrogen bonds with two threonine residues (Ala91 and Asp93), exhibiting more stable structure of loop region and promoting the polar interaction. Moreover, this mutation shortened the length of a helix 4, which may affect the stability of SAA1. Structural changes in SAA1 protein caused the surface of Asp90 to be exposed in solvent environment, leading to the increased hydrophilic region. In addition, the construction of 3D models in SCOT1 and its mutant Thr58Met revealed that this substitution resulted in the disappearance of the hydrogen bond between Thr58 and Asp206, the reduction of intramolecular polar interactions and the expansion of hydrophobic region (FIGS. 6C and 6D), suggesting its potential function alteration in RA pathogenesis.

4. Discussion

The inventors performed perspective WES aiming to identify potentially causal biomarkers in a cohort of Chinese RA patients. The inventors used the method as disclosed herein to focus on investigating the occurrence frequency of variants in genes previously associated with RA as well as novel genes. Despite known variants of TGFβ1 and FOXP3 genes associated with increased RA risk, two novel risk variant loci in these two genes were for the first time identified to be implicated in the RA risk (group 4 and group 6 in Table 5). A novel splicing variant (rs199982059) of TGFβ1 was found to be significantly enriched in 4 RA patients, but absent in healthy controls. TGFβ1 is a pivotal protein in the pathogenesis of a number of autoimmune disorders and its dysregulation is also increasingly implicated in the risk of developing RA. RNA splicing is a focal point on connection between genetic variations and complex disorders, and this novel splicing variant of TGFβ1 might provide new insights into the genetic determinants of RA disease. In addition, a novel missense variant (chrX: 49114808) of FOXP3 was observed in 8 RA patients. FOXP3 is a unique regulatory T cell ($T_{reg}$)-specific marker and important in the development of RA-derived $T_{reg}$ cells as a transcriptional factor. In spite of the other known variants in TGFβ1 and FOXP3 genes associated with RA, these two newly-identified variants in our Chinese RA patients may offer the novel genetic contributions to the RA risk.

The inventors have also identified six novel and deleterious genes that are classified as pathogenic in ClinVar database (Table 7). Of these, a missense variant (rs79681911) of SAA1, initially characterized by serum amyloid a variant (OMIM 104750) and required for the amyloidosis disease process, was identified in the RA patients. SAA1 has been reported to play a pathogenic role in the pro-inflammatory cascades in RA, therefore, this novel deleterious variant may be implicated in RA risk as a sensitive indicator of inflammatory activity. Additional pathogenic variant (rs75134564) of OXCT1 was predicted to be disease-related in 4 RA patients based on LR score, which previously implicated in succinyl-CoA acetoacetate transferase deficiency (OMIM 601424) in clinic. OXCT1 encoding enzyme SCOT1 is essential for ketone body metabolism and involved in cardiovascular disease, which are shown to be strongly associated with the course of RA, suggesting this enzyme may potentially contribute to RA prognosis. Importantly, the 3D structural analysis of these two potential biomarkers revealed that the substitution of mutation points may be involved in the functional alteration of the proteins and further impact on RA disease progression (FIG. 6).

The inventors sought to identify novel genes or biological candidate pathways fundamental to the risk of RA disease, including both rare and common variants. To elucidate additive effects of polygenic variants that affect the same gene or pathway, the inventors performed gene burden test and pathway analysis. Notably, the biological impact of rare and deleterious variants is likely to be greater when present as two copies. In the study, 5 homozygous variants (group 5 in FIG. 3; Table 5) were detected in the RA patients but not in healthy controls. Intriguingly, a non-frameshift indel variant (rs61406813) of NCR3LG1 (natural cytotoxicity triggering receptor 3 ligand 1) was identified in the RA patients as homozygote. NCR3LG1 could be detected on monocytes and neutrophils after application of inflammatory stimuli, and it was initially described as a tumor cell-expressed ligand of NKp30, which is found to be implicated in RA-associated inflammation. Additionally, a missense variant (rs61014678) of RAP1GAP (RAP1 GTPase Activating Protein) was identified as damaging (disease-related, D) by determinant of LR model in the RA patients. RAP1GAP regulates the activity of the ras-related RAP1 protein, which involves in induction of apoptotic pathway in synovial fibroblasts and plays a critical role in oxidative stress and T cell behavior in RA synovial tissues. Thus, these two homozygous variants may perform stronger functions in RA pathogenic mechanisms.

The WES analysis totally identified 381 genes that may partially contribute to RA pathogenesis and disease progression, including 3 genes (TGFβ1, FOXP3 and SAA1) previously implicated in RA and 378 novel candidate genes. Biologic pathway analysis might help us to deeply understand RA pathogenesis, and previously biological pathways have been identified from genes in large-scale association analysis of GWAS data (Table 6), such as autoimmune thyroid disease, natural killer cell mediated cytotoxicity and T cell receptor signaling pathways. The inventors deciphered enrichment of the identified deleterious genes within additional pathways of ECM-receptor interaction, protein digestion and absorption, focal adhesion and glycerophospholipid metabolism based on our WES data (Table 8), which have been implicated in the autoimmune conditions or pathogenesis of RA. The inventors also sought to identify potential deleterious variants associated with disease duration among RA patients. The pathway analysis focusing on variants enriched among RA patients with disease duration ≥3-year highlighted seven novel genes in olfactory transduction pathway (Table 8), which has been previously reported to be implicated in regulating inflammatory responses.

Pathogenesis of RA is complicated and includes both environmental and genetic factors. Recently, gut microbiota has been evident of being implicated in RA pathogenesis and treatment responses as a critical environmental factor that influences metabolic and immune homeostasis, involvement of protein digestion and absorption, glycerophospholipid metabolism and olfactory transduction pathway, which were also enriched by novel candidate genes identified in the Chinese RA patients (Table 5). In addition, the homozygous variant NCR3LG1 (group 5 in Table 5) may mediate autoimmune and microbial infection-induced inflammation by associating with the ligand of NKp30. Therefore, these involved novel deleterious genes might be convincingly considered genetic contributions to microbial alteration in relation to the pathogenesis and development of RA.

Figure 7:
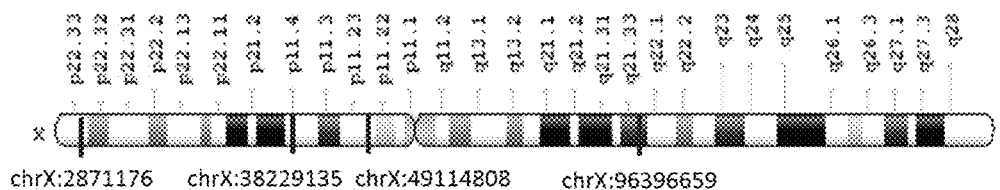
FIG. 7 shows the comparison of X chromosome associated variants distribution between female and male in RA patients.

Genetic factors on the X chromosome always contribute to the increased risk of developing autoimmune disorders in females compared with males, such as RA. According to the method as described herein, four novel and deleterious variants were investigated to be associated with sex bias in the Chinese RA patients, including OTC (Ornithine Transcarbamylase) (rs72554348), DIAPH2 (Diaphanous Related Formin 2) (rs363755), ARSE (Arylsulfatase E) (rs56393981) and FOXP3 (chrX:49114808) (FIG. 7). Notably, OTC, ARSE and FOXP3 were previously reported to be implicated in x-linked diseases (Bennett C L et al., Nature genetics 2001; 27:20; Luksan 0 et al., Hum Mutat 2010; 31:E1294-1303; and Jeon G W et al., Ann Clin Lab 2013; 43:70-75), in which these three novel variants identified in the present study are also associated with female, supporting that the association of variants on X chromosome and RA may further provide molecular evidence as a risk factor contributing to increased susceptibility in Chinese female RA patients.

In summary, the inventors have performed WES to present support and improve our understanding of associations with genetic biomarkers that may be involved in the development of RA in the Chinese population. The biomarkers highlighted include previously implicated genes as well as novel genes and pathways, involved in regulation of adaptive immune response, transmission of nerve impulse and chromosome organization. This study significantly extends the work of GWAS and provides new insight into fundamental etiologic mechanisms in this common autoimmune disease. Taken together, these novel biomarkers can be served as novel biomarkers for valid diagnosis tools for identification of RA patients from normal people specifically for Chinese Han population.

TABLE 5

Candidate variant list from RA versus control comparison.

| group | chr | pos | id | ref | alt | gene | LR | Gene burden ratio KG East Asia | Gene burden ratio healthy Ctrl | Total No. of alleles in gene healthy Ctrl | Total No. of alleles in gene RA | No. alt alleles in genes healthy Ctrl | No. alt alleles in genes RA | No. of cases with alt alleles | Variant allele frequency KG East Asia |
|---|---|---|---|---|---|---|---|---|---|---|---|---|---|---|---|
| 2 | 10 | 101829514 | rs61751507 | C | T | CPN1 | T | 1.81 | 1.52 | 132 | 116 | 3 | 4 | 4 | 0.0248 |
| 2 | 11 | 18291302 | rs79681911 | G | A | SAA1 | T | 1.81 | . | 132 | 116 | 0 | 3 | 3 | 0.0198 |
| 2 | 3 | 133476698 | rs41295774 | A | G | TF | T | 1.81 | 3.41 | 132 | 116 | 2 | 6 | 6 | 0.0238 |
| 2 | 5 | 41862758 | rs75134564 | G | A | OXCT1 | D | 3.62 | 4.55 | 132 | 116 | 1 | 4 | 4 | 0.0069 |
| 2 | 7 | 44104839 | rs77938727 | C | T | PGAM2 | D | 1.81 | 2.28 | 132 | 116 | 1 | 2 | 2 | 0.0129 |
| 2 | X | 38229135 | rs72554348 | G | C | OTC | . | 2.79 | 2.32 | 132 | 114 | 3 | 6 | 5 | 0.0144 |
| 4 | 10 | 102027318 | rs200164003 | G | C | CWF19L1 | . | 7.24 | . | 132 | 116 | 0 | 4 | 4 | 0.001 |
| 4 | 10 | 114917776 | rs191206106 | C | G | TCF7L2 | . | 12.67 | 7.97 | 264 | 232 | 1 | 7 | 7 | 0.001 |
| 4 | 10 | 114925441 | rs138649767 | G | A | TCF7L2 | D | 12.67 | 7.97 | 264 | 232 | 1 | 7 | 7 | 0.0089 |
| 4 | 10 | 135086331 | rs536126291 | C | T | ADAM8 | . | 5.43 | 3.41 | 264 | 232 | 1 | 3 | 3 | 0.002 |
| 4 | 10 | 135087305 | rs3810960 | G | A | ADAM8 | . | 5.43 | 3.41 | 264 | 232 | 1 | 3 | 3 | 0.003 |
| 4 | 10 | 25144247 | rs199794379 | A | G | PRTFDC1 | D | 5.43 | . | 264 | 232 | 0 | 3 | 3 | 0.004 |
| 4 | 10 | 25147326 | rs199983667 | C | A | PRTFDC1 | D | 5.43 | . | 264 | 232 | 0 | 3 | 3 | 0.001 |
| 4 | 10 | 35894560 | rs142589386 | G | A | GJD4 | . | 5.43 | 3.41 | 396 | 348 | 1 | 3 | 3 | 0.003 |
| 4 | 10 | 35897091 | rs547212582 | T | C | GJD4 | D | 5.43 | 3.41 | 396 | 348 | 1 | 3 | 3 | 0.002 |
| 4 | 10 | 35897205 | rs192362407 | G | A | GJD4 | D | 5.43 | 3.41 | 396 | 348 | 1 | 3 | 3 | 0.004 |
| 4 | 10 | 50854641 | rs539884711 | C | A | CHAT | D | 1.81 | 2.28 | 396 | 348 | 1 | 2 | 2 | 0.001 |
| 4 | 10 | 50857631 | rs201293521 | G | T | CHAT | D | 1.81 | 2.28 | 396 | 348 | 1 | 2 | 2 | 0.001 |
| 4 | 10 | 50870806 | rs116628504 | G | A | CHAT | D | 1.81 | 2.28 | 396 | 348 | 1 | 3 | 3 | 0.006 |
| 4 | 1 | 100174455 | rs192583899 | T | C | FRRS1 | . | 1.81 | . | 264 | 232 | 0 | 3 | 3 | 0.003 |
| 4 | 1 | 100177969 | rs187278122 | A | G | FRRS1 | . | 1.81 | . | 264 | 232 | 0 | 3 | 3 | 0.006 |

TABLE 5-continued

Candidate variant list from RA versus control comparison.

| group | chr | pos | id | ref | alt | gene | LR | Gene burden ratio | | Total No. of alleles in gene | | No. alt alleles in genes | | No. of cases with alt alleles | Variant allele frequency |
| --- | --- | --- | --- | --- | --- | --- | --- | --- | --- | --- | --- | --- | --- | --- | --- |
| | | | | | | | | KG East Asia | healthy Ctrl | healthy Ctrl | RA | healthy Ctrl | RA | | KG East Asia |
| 4 | 1 | 103444283 | rs192842970 | G | A | COL11A1 | D | 10.86 | 3.4 | 394 | 348 | 2 | 6 | 6 | 0.004 |
| 4 | 1 | 103468295 | rs2622875 | C | T | COL11A1 | . | 10.86 | 3.4 | 394 | 348 | 2 | 6 | 6 | 0.001 |
| 4 | 1 | 103544434 | rs12136865 | A | G | COL11A1 | . | 10.86 | 3.4 | 394 | 348 | 2 | 6 | 6 | 0.001 |
| 4 | 11 | 111857624 | . | T | C | DIXDC1 | . | 5.43 | 1.71 | 264 | 232 | 2 | 3 | 3 | 0.002 |
| 4 | 11 | 111889694 | . | T | C | DIXDC1 | . | 5.43 | 1.71 | 264 | 232 | 2 | 3 | 3 | 0.001 |
| 4 | 11 | 121426036 | rs140499624 | A | G | SORL1 | . | 7.24 | 2.28 | 132 | 116 | 1 | 2 | 2 | 0.004 |
| 4 | 11 | 124006828 | rs2276055 | C | T | VWA5A | . | 7.24 | . | 132 | 116 | 0 | 4 | 4 | 0.0079 |
| 4 | 11 | 124742777 | rs117828759 | C | T | ROBO3 | . | 4.95 | 2.01 | 128 | 106 | 3 | 5 | 5 | 0.0079 |
| 4 | 11 | 2432720 | rs548094761 | C | T | TRPM5 | D | 3.62 | 6.83 | 396 | 348 | 1 | 6 | 6 | 0.003 |
| 4 | 11 | 2434772 | rs74570003 | G | T | TRPM5 | D | 3.62 | 6.83 | 396 | 348 | 1 | 6 | 6 | 0.003 |
| 4 | 11 | 2441443 | rs201184691 | G | A | TRPM5 | . | 3.62 | 6.83 | 396 | 348 | 1 | 6 | 6 | 0.004 |
| 4 | 1 | 1267086 | rs201655269 | C | T | TAS1R3 | D | 7.24 | 4.55 | 396 | 348 | 1 | 4 | 4 | 0.001 |
| 4 | 1 | 1268119 | rs548456115 | C | T | TAS1R3 | D | 7.24 | 4.55 | 396 | 348 | 1 | 4 | 4 | 0.001 |
| 4 | 1 | 1269146 | rs576045705 | G | A | TAS1R3 | D | 7.24 | 4.55 | 396 | 348 | 1 | 4 | 4 | 0.001 |
| 4 | 11 | 2909699 | rs80153297 | C | T | SLC22A18AS | . | 2.41 | . | 264 | 232 | 0 | 4 | 4 | 0.005 |
| 4 | 11 | 2920835 | rs189560463 | G | C | SLC22A18AS | . | 2.41 | . | 264 | 232 | 0 | 4 | 4 | 0.002 |
| 4 | 1 | 146759364 | . | C | T | CHD1L | . | 5.62 | 3.54 | 132 | 112 | 1 | 3 | 3 | 0.001 |
| 4 | 11 | 479160 | rs2301168 | G | T | PTDSS2 | . | 3.62 | 4.55 | 264 | 232 | 1 | 4 | 4 | 0.003 |
| 4 | 11 | 490416 | rs200446000 | C | T | PTDSS2 | . | 3.62 | 4.55 | 264 | 232 | 1 | 4 | 4 | 0.004 |
| 4 | 11 | 151958735 | rs190916122 | A | G | S100A10 | . | 5.43 | 1.68 | 130 | 116 | 2 | 3 | 3 | 0.005 |
| 4 | 11 | 56756398 | rs13343184 | G | T | OR5AK2 | . | 2.72 | 3.41 | 264 | 232 | 1 | 3 | 3 | 0.002 |
| 4 | 11 | 56756578 | rs189588796 | C | T | OR5AK2 | . | 2.72 | 3.41 | 264 | 232 | 1 | 3 | 3 | 0.002 |

TABLE 5-continued

Candidate variant list from RA versus control comparison.

| group | chr | pos | id | ref | alt | gene | LR | Gene burden ratio KG East Asia | Gene burden ratio healthy Ctrl | Total No. of alleles in gene healthy Ctrl | Total No. of alleles in gene RA | No. alt alleles in genes healthy Ctrl | No. alt alleles in genes RA | No. of cases with alt alleles | Variant allele frequency KG East Asia |
|---|---|---|---|---|---|---|---|---|---|---|---|---|---|---|---|
| 4 | 1 | 160121885 | rs146860131 | C | T | ATP1A4 | . | 10.86 | 3.41 | 528 | 464 | 2 | 6 | 6 | 0.003 |
| 4 | 1 | 160143514 | rs45441496 | T | G | ATP1A4 | . | 10.86 | 3.41 | 528 | 464 | 2 | 6 | 6 | 0.0089 |
| 4 | 1 | 160143945 | rs199962758 | T | C | ATP1A4 | D | 10.86 | 3.41 | 528 | 464 | 2 | 6 | 6 | 0.003 |
| 4 | 1 | 160144538 | rs185461260 | G | T | ATP1A4 | . | 10.86 | 3.41 | 528 | 464 | 2 | 6 | 6 | 0.004 |
| 4 | 1 | 161090011 | rs201971149 | G | C | NIT1 | D | 3.62 | 2.28 | 132 | 116 | 1 | 2 | 2 | 0.001 |
| 4 | 1 | 63400493 | rs17656941 | C | T | ATL3 | . | 3.62 | 2.28 | 264 | 232 | 1 | 2 | 2 | 0.003 |
| 4 | 1 | 63403670 | rs3781606 | C | T | ATL3 | . | 3.62 | 2.28 | 264 | 232 | 1 | 2 | 2 | 0.0079 |
| 4 | 11 | 6585361 | rs113574909 | A | G | DNHD1 | . | 3.62 | 2.28 | 132 | 116 | 1 | 2 | 2 | 0.0099 |
| 4 | 11 | 67786664 | rs535638253 | G | A | ALDH3B1 | . | 1.81 | 2.84 | 528 | 464 | 2 | 5 | 5 | 0.001 |
| 4 | 11 | 67789111 | rs371833737 | C | T | ALDH3B1 | . | 1.81 | 2.84 | 528 | 464 | 2 | 5 | 5 | 0.003 |
| 4 | 11 | 67789277 | rs370461081 | G | A | ALDH3B1 | . | 1.81 | 2.84 | 528 | 464 | 2 | 5 | 5 | 0.002 |
| 4 | 11 | 67795344 | rs374814356 | G | A | ALDH3B1 | . | 1.81 | 2.84 | 528 | 464 | 2 | 5 | 5 | 0.005 |
| 4 | 11 | 74716666 | rs202090872 | G | C | NEU3 | D | 5.43 | 3.41 | 396 | 348 | 1 | 3 | 3 | 0.003 |
| 4 | 11 | 74716935 | rs200629627 | G | A | NEU3 | D | 5.43 | 3.41 | 396 | 348 | 1 | 3 | 3 | 0.003 |
| 4 | 11 | 74717001 | rs539514716 | C | T | NEU3 | D | 5.43 | 3.41 | 396 | 348 | 1 | 3 | 3 | 0.002 |
| 4 | 1 | 176853472 | rs79630456 | C | T | ASTN1 | . | 2.72 | 1.71 | 132 | 116 | 2 | 3 | 3 | 0.0089 |
| 4 | 11 | 76873966 | . | C | T | MYO7A | D | 3.62 | 2.28 | 264 | 232 | 1 | 2 | 2 | 0.001 |
| 4 | 11 | 76900487 | . | G | C | MYO7A | D | 3.62 | 2.28 | 264 | 232 | 1 | 2 | 2 | 0.004 |
| 4 | 1 | 179949680 | rs75914589 | C | T | ARHGEF10L | . | 3.62 | 2.28 | 132 | 116 | 1 | 2 | 2 | 0.0089 |
| 4 | 11 | 82536079 | rs202237309 | C | T | PRCP | D | 3.62 | 2.28 | 264 | 232 | 1 | 2 | 2 | 0.004 |
| 4 | 11 | 82549453 | rs536616254 | C | T | PRCP | D | 3.62 | 2.28 | 264 | 232 | 1 | 2 | 2 | 0.001 |
| 4 | 11 | 82644887 | rs553247583 | G | GC | DDIAS | . | 1.81 | 2.28 | 132 | 116 | 1 | 2 | 2 | 0.006 |

TABLE 5-continued

Candidate variant list from RA versus control comparison.

| group | chr | pos | id | ref | alt | gene | LR | Gene burden ratio KG East Asia | Gene burden ratio healthy Ctrl | Total No. of alleles in gene healthy Ctrl | Total No. of alleles in gene RA | No. alt alleles in genes healthy Ctrl | No. alt alleles in genes RA | No. of cases with alt alleles | Variant allele frequency KG East Asia |
|---|---|---|---|---|---|---|---|---|---|---|---|---|---|---|---|
| 4 | 1 | 183084778 | rs200671087 | A | G | LAMC1 | . | 3.62 | 2.28 | 264 | 232 | 1 | 2 | 2 | 0.002 |
| 4 | 1 | 183086586 | rs544527088 | G | A | LAMC1 | . | 3.62 | 2.28 | 264 | 232 | 1 | 2 | 2 | 0.001 |
| 4 | 11 | 8959479 | rs147479456 | G | A | ASCL3 | D | 3.62 | . | 264 | 232 | 0 | 4 | 4 | 0.001 |
| 4 | 11 | 8959607 | rs201803232 | C | T | ASCL3 | D | 3.62 | . | 264 | 232 | 0 | 4 | 4 | 0.003 |
| 4 | 11 | 93754643 | rs192979315 | T | A | HEPHL1 | D | 5.43 | 6.83 | 528 | 464 | 1 | 6 | 6 | 0.002 |
| 4 | 11 | 93754667 | rs564600266 | A | G | HEPHL1 | D | 5.43 | 6.83 | 528 | 464 | 1 | 6 | 6 | 0.005 |
| 4 | 11 | 93779075 | rs151306000 | A | T | HEPHL1 | D | 5.43 | 6.83 | 528 | 464 | 1 | 6 | 6 | 0.0069 |
| 4 | 11 | 93797581 | rs146491431 | G | C | HEPHL1 | D | 5.43 | 6.83 | 528 | 464 | 1 | 6 | 6 | 0.002 |
| 4 | 1 | 19566783 | rs201918168 | C | T | EMC1 | . | 1.81 | 3.41 | 132 | 116 | 1 | 3 | 3 | 0.0079 |
| 4 | 1 | 197070906 | rs118010078 | C | T | ASPM | D | 3.62 | 2.28 | 264 | 232 | 2 | 4 | 4 | 0.0069 |
| 4 | 1 | 197072871 | rs144969324 | C | T | ASPM | D | 3.62 | 2.28 | 264 | 232 | 2 | 4 | 4 | 0.005 |
| 4 | 1 | 203195004 | rs190551025 | C | T | CHIT1 | . | 3.62 | 4.55 | 264 | 232 | 1 | 4 | 4 | 0.006 |
| 4 | 1 | 203198732 | rs16851144 | C | T | CHIT1 | D | 3.62 | 4.55 | 264 | 232 | 1 | 4 | 4 | 0.001 |
| 4 | 12 | 122247945 | rs375525174 | G | T | SETD1B | D | 7.24 | 1.52 | 264 | 232 | 3 | 4 | 4 | 0.002 |
| 4 | 12 | 122261544 | rs553963413 | G | A | SETD1B | D | 7.24 | 1.52 | 264 | 232 | 3 | 4 | 4 | 0.002 |
| 4 | 12 | 12672941 | rs187382315 | T | G | DUSP16 | . | 7.24 | 2.24 | 130 | 116 | 2 | 4 | 4 | 0.005 |
| 4 | 1 | 21926031 | rs138045307 | C | T | RAP1GAP | D | 7.24 | 4.55 | 264 | 232 | 2 | 8 | 7 | 0.001 |
| 4 | 1 | 22149838 | rs554059442 | C | T | HSPG2 | D | 2.72 | . | 396 | 348 | 0 | 3 | 3 | 0.002 |
| 4 | 1 | 22157470 | rs77527456 | C | T | HSPG2 | . | 2.72 | . | 396 | 348 | 0 | 3 | 3 | 0.0079 |
| 4 | 1 | 22157544 | rs368497178 | C | T | HSPG2 | D | 2.72 | 4.55 | 396 | 348 | 0 | 3 | 3 | 0.001 |
| 4 | 1 | 225599137 | rs192884088 | C | T | LBR | . | 3.64 | 4.55 | 526 | 462 | 1 | 4 | 4 | 0.001 |
| 4 | 1 | 225600276 | rs145104817 | C | T | LBR | D | 3.64 | 4.55 | 526 | 462 | 1 | 4 | 4 | 0.002 |

TABLE 5-continued

Candidate variant list from RA versus control comparison.

| group | chr | pos | id | ref | alt | gene | LR | Gene burden ratio KG East Asia | Gene burden ratio healthy Ctrl | Total No. of alleles in gene healthy Ctrl | Total No. of alleles in gene RA | No. alt alleles in genes healthy Ctrl | No. alt alleles in genes RA | No. of cases with alt alleles | Variant allele frequency KG East Asia |
|---|---|---|---|---|---|---|---|---|---|---|---|---|---|---|---|
| 4 | 1 | 225607507 | rs144956313 | T | A | LBR | . | 3.64 | 4.55 | 526 | 462 | 1 | 4 | 4 | 0.001 |
| 4 | 1 | 225611800 | rs375540112 | T | C | LBR | . | 3.64 | 4.55 | 526 | 462 | 1 | 4 | 4 | 0.002 |
| 4 | 1 | 228109706 | rs146233417 | C | A | WNT9A | . | 5.43 | 3.41 | 132 | 116 | 1 | 3 | 3 | 0.005 |
| 4 | 1 | 23281822 | rs543523784 | C | T | LACTBL1 | . | 3.62 | 2.28 | 528 | 464 | 2 | 4 | 4 | 0.001 |
| 4 | 1 | 23285238 | rs374793392 | C | T | LACTBL1 | . | 3.62 | 2.28 | 528 | 464 | 2 | 4 | 4 | 0.004 |
| 4 | 1 | 23285418 | rs186492394 | A | G | LACTBL1 | . | 3.62 | 2.28 | 528 | 464 | 2 | 4 | 4 | 0.003 |
| 4 | 1 | 23289623 | rs557724162 | C | T | LACTBL1 | . | 3.62 | 2.28 | 528 | 464 | 2 | 4 | 4 | 0.001 |
| 4 | 1 | 241850753 | rs146579868 | T | C | WDR64 | . | 7.24 | 2.28 | 264 | 232 | 2 | 4 | 4 | 0.002 |
| 4 | 1 | 241929510 | rs576824811 | C | T | WDR64 | . | 7.24 | 2.28 | 264 | 232 | 2 | 4 | 4 | 0.001 |
| 4 | 12 | 52822463 | rs192170292 | A | T | KRT75 | D | 1.81 | 2.28 | 264 | 232 | 1 | 2 | 2 | 0.002 |
| 4 | 12 | 52825806 | rs548132126 | A | G | KRT75 | D | 1.81 | 2.28 | 264 | 232 | 1 | 2 | 2 | 0.001 |
| 4 | 12 | 52908938 | rs375140289 | C | T | KRT5 | D | 5.43 | 1.71 | 264 | 232 | 2 | 3 | 3 | 0.002 |
| 4 | 12 | 52913517 | rs638907 | G | A | KRT5 | . | 5.43 | 1.71 | 264 | 232 | 2 | 3 | 3 | 0.0079 |
| 4 | 1 | 27875517 | rs111827498 | AAGG | A | AHDC1 | . | 7.24 | . | 132 | 116 | 0 | 4 | 4 | 0.004 |
| 4 | 12 | 94613786 | rs117324576 | G | A | PLXNC1 | . | 9.05 | 1.9 | 132 | 116 | 3 | 5 | 5 | 0.0099 |
| 4 | 12 | 99478699 | rs370166322 | T | C | ANKS1B | . | 3.85 | 2.22 | 242 | 218 | 1 | 2 | 2 | 0.004 |
| 4 | 12 | 99640652 | rs747712860 | G | A | ANKS1B | . | 3.85 | 2.22 | 242 | 218 | 1 | 2 | 2 | 0.0079 |
| 4 | 13 | 103392313 | rs372526941 | C | G | CCDC168 | . | 2.72 | 1.71 | 396 | 348 | 2 | 3 | 3 | 0.003 |
| 4 | 13 | 103396838 | rs183822515 | A | G | CCDC168 | . | 2.72 | 1.71 | 396 | 348 | 2 | 3 | 3 | 0.006 |
| 4 | 13 | 103397088 | rs192109030 | C | T | CCDC168 | . | 2.72 | 1.71 | 396 | 348 | 2 | 3 | 3 | 0.001 |
| 4 | 13 | 106142185 | rs113341591 | C | T | DAOA | . | 6.34 | 2.66 | 264 | 232 | 3 | 7 | 7 | 0.0069 |
| 4 | 13 | 106142236 | rs111916808 | G | A | DAOA | . | 6.34 | 2.66 | 264 | 232 | 3 | 7 | 7 | 0.0099 |

TABLE 5-continued

Candidate variant list from RA versus control comparison.

| group | chr | pos | id | ref | alt | gene | LR | Gene burden ratio KG East Asia | Gene burden ratio healthy Ctrl | Total No. of alleles in gene healthy Ctrl | Total No. of alleles in gene RA | No. alt alleles in genes healthy Ctrl | No. alt alleles in genes RA | No. of cases with alt alleles | Variant allele frequency KG East Asia |
|---|---|---|---|---|---|---|---|---|---|---|---|---|---|---|---|
| 4 | 1 | 35226964 | rs146378222 | G | A | GJB4 | D | 3.02 | 1.9 | 528 | 464 | 3 | 5 | 5 | 0.006 |
| 4 | 1 | 35227225 | rs373126632 | C | T | GJB4 | D | 3.02 | 1.9 | 528 | 464 | 3 | 5 | 5 | 0.001 |
| 4 | 1 | 35227231 | rs146979528 | G | A | GJB4 | D | 3.02 | 1.9 | 528 | 464 | 3 | 5 | 5 | 0.002 |
| 4 | 1 | 35227585 | rs201000959 | C | T | GJB4 | D | 3.02 | 1.9 | 528 | 464 | 3 | 5 | 5 | 0.003 |
| 4 | 1 | 35350573 | rs34565935 | CT | C | DLGAP3 | . | 1.81 | 2.28 | 132 | 116 | 1 | 2 | 2 | 0.006 |
| 4 | 1 | 36056256 | rs114404250 | G | A | TFAP2E | D | 2.72 | 3.41 | 132 | 116 | 1 | 3 | 3 | 0.0069 |
| 4 | 13 | 76378421 | rs190172966 | A | T | LMO7 | . | 3.62 | . | 396 | 348 | 0 | 4 | 4 | 0.003 |
| 4 | 13 | 76395306 | rs181473989 | C | T | LMO7 | . | 3.62 | . | 396 | 348 | 0 | 4 | 4 | 0.005 |
| 4 | 13 | 76419523 | rs566129586 | C | T | LMO7 | . | 3.62 | . | 396 | 348 | 0 | 4 | 4 | 0.001 |
| 4 | 1 | 38025103 | rs41267309 | T | C | DNALI1 | . | 3.62 | 2.28 | 132 | 116 | 1 | 2 | 2 | 0.0089 |
| 4 | 13 | 95117993 | rs144365832 | C | T | DCT | D | 1.81 | 2.28 | 264 | 232 | 1 | 2 | 2 | 0.004 |
| 4 | 13 | 95121301 | rs202004134 | T | C | DCT | . | 1.81 | 2.28 | 264 | 232 | 1 | 2 | 2 | 0.001 |
| 4 | 14 | 21793077 | rs543867152 | C | T | RPGRIP1 | D | 7.24 | . | 264 | 232 | 0 | 4 | 4 | 0.001 |
| 4 | 14 | 21793236 | rs7157052 | G | A | RPGRIP1 | . | 7.24 | . | 264 | 232 | 0 | 4 | 4 | 0.002 |
| 4 | 14 | 43664319 | rs107711519 | TA | T | CFAP57 | . | 7.54 | 2.3 | 384 | 334 | 2 | 4 | 4 | 0.003 |
| 4 | 1 | 43688508 | rs549638533 | T | TCAC | CFAP57 | . | 7.54 | 2.3 | 384 | 334 | 2 | 4 | 4 | 0.005 |
| 4 | 1 | 43689879 | rs138114943 | C | A | CFAP57 | . | 7.54 | 2.3 | 384 | 334 | 2 | 4 | 4 | 0.003 |
| 4 | 14 | 59954385 | rs76472382 | A | G | JKAMP | . | 2.72 | . | 130 | 116 | 0 | 3 | 3 | 0.0069 |
| 4 | 14 | 77735581 | rs117207261 | C | G | NGB | D | 2.72 | . | 264 | 232 | 0 | 3 | 3 | 0.004 |
| 4 | 14 | 77735593 | rs77722833 | G | C | NGB | D | 2.72 | . | 264 | 232 | 0 | 3 | 3 | 0.001 |
| 4 | 14 | 88406259 | rs138577661 | A | G | GALC | D | 7.24 | 2.28 | 396 | 348 | 2 | 4 | 4 | 0.0079 |
| 4 | 14 | 88411994 | rs146286491 | C | T | GALC | D | 7.24 | 2.28 | 396 | 348 | 2 | 4 | 4 | 0.006 |

TABLE 5-continued

Candidate variant list from RA versus control comparison.

| group | chr | pos | id | ref | alt | gene | LR | Gene burden ratio KG East Asia | Gene burden ratio healthy Ctrl | Total No. of alleles in gene healthy Ctrl | Total No. of alleles in gene RA | No. alt alleles in genes healthy Ctrl | No. alt alleles in genes RA | No. of cases with alt alleles | Variant allele frequency KG East Asia |
|---|---|---|---|---|---|---|---|---|---|---|---|---|---|---|---|
| 4 | 14 | 88450836 | rs534598133 | C | T | GALC | D | 7.24 | 2.28 | 396 | 348 | 2 | 4 | 4 | 0.002 |
| 4 | 15 | 39876498 | rs200938835 | T | C | THBS1 | . | 3.62 | 4.55 | 396 | 348 | 1 | 4 | 4 | 0.002 |
| 4 | 15 | 39881204 | rs200366954 | A | G | THBS1 | D | 3.62 | 4.55 | 396 | 348 | 1 | 4 | 4 | 0.001 |
| 4 | 15 | 39886402 | rs185847032 | G | A | THBS1 | . | 3.62 | 4.55 | 396 | 348 | 1 | 4 | 4 | 0.002 |
| 4 | 15 | 45388079 | rs147945181 | G | A | DUOX2 | D | 4.07 | 1.71 | 660 | 580 | 6 | 9 | 9 | 0.005 |
| 4 | 15 | 45388106 | rs200541410 | G | A | DUOX2 | D | 4.07 | 1.71 | 660 | 580 | 6 | 9 | 9 | 0.004 |
| 4 | 15 | 45391946 | rs368488511 | C | T | DUOX2 | D | 4.07 | 1.71 | 660 | 580 | 6 | 9 | 9 | 0.002 |
| 4 | 15 | 45399533 | rs76411432 | C | T | DUOX2 | . | 4.07 | 1.71 | 660 | 580 | 6 | 9 | 9 | 0.005 |
| 4 | 15 | 45399648 | rs180671269 | T | A | DUOX2 | . | 4.07 | 1.71 | 660 | 580 | 6 | 9 | 9 | 0.003 |
| 4 | 1 | 54694412 | rs75191666 | G | A | SSBP3 | . | 2.84 | 3.35 | 248 | 222 | 1 | 3 | 3 | 0.0099 |
| 4 | 1 | 54707891 | rs199692606 | A | G | SSBP3 | . | 2.84 | 3.35 | 248 | 222 | 1 | 3 | 3 | 0.001 |
| 4 | 15 | 48512855 | rs116848967 | G | A | SLC12A1 | D | 10.86 | 4.55 | 264 | 232 | 1 | 4 | 4 | 0.003 |
| 4 | 15 | 48566800 | rs201516084 | T | C | SLC12A1 | . | 10.86 | 4.55 | 264 | 232 | 1 | 4 | 4 | 0.005 |
| 4 | 15 | 65766537 | rs192889990 | A | G | DPP8 | . | 5.43 | . | 264 | 232 | 0 | 3 | 3 | 0.002 |
| 4 | 15 | 65790192 | rs564795298 | T | C | DPP8 | . | 5.43 | . | 264 | 232 | 0 | 3 | 3 | 0.001 |
| 4 | 15 | 79298783 | rs182075492 | G | C | RASGRF1 | . | 1.81 | . | 132 | 116 | 0 | 3 | 3 | 0.005 |
| 4 | 15 | 89869833 | rs55962804 | C | T | POLG | . | 2.72 | 1.71 | 132 | 116 | 2 | 3 | 3 | 0.0089 |
| 4 | 15 | 99670848 | . | G | A | SYNM | . | 3.62 | 2.28 | 264 | 232 | 1 | 2 | 2 | 0.001 |
| 4 | 15 | 99673059 | . | C | T | SYNM | . | 3.62 | 2.28 | 264 | 232 | 1 | 2 | 2 | 0.002 |
| 4 | 1 | 6184131 | rs200938629 | T | A | CHD5 | D | 1.81 | 2.28 | 396 | 348 | 1 | 2 | 2 | 0.004 |
| 4 | 1 | 6188678 | rs193121978 | C | G | CHD5 | . | 1.81 | 2.28 | 396 | 348 | 1 | 2 | 2 | 0.001 |
| 4 | 1 | 6228290 | rs571052710 | C | G | CHD5 | D | 1.81 | 2.28 | 396 | 348 | 1 | 2 | 2 | 0.002 |

TABLE 5-continued

Candidate variant list from RA versus control comparison.

| group | chr | pos | id | ref | alt | gene | LR | Gene burden ratio KG East Asia | Gene burden ratio healthy Ctrl | Total No. of alleles in gene healthy Ctrl | Total No. of alleles in gene RA | No. alt alleles in genes healthy Ctrl | No. alt alleles in genes RA | No. of cases with alt alleles | Variant allele frequency KG East Asia |
|---|---|---|---|---|---|---|---|---|---|---|---|---|---|---|---|
| 4 | 16 | 19883621 | rs200345676 | G | T | GPRC5B | D | 1.81 | 2.28 | 132 | 116 | 1 | 2 | 2 | 0.0079 |
| 4 | 16 | 27492392 | rs200088316 | C | T | GTF3C1 | . | 5.43 | 1.71 | 264 | 232 | 2 | 3 | 3 | 0.001 |
| 4 | 16 | 27494449 | rs536534746 | G | A | GTF3C1 | . | 5.43 | 1.71 | 264 | 232 | 2 | 3 | 3 | 0.003 |
| 4 | 16 | 424403 | rs11641325 | C | T | TMEM8A | . | 5.48 | 3.42 | 262 | 230 | 1 | 3 | 3 | 0.004 |
| 4 | 16 | 426536 | rs143874266 | C | T | TMEM8A | . | 5.48 | 3.42 | 262 | 230 | 1 | 3 | 3 | 0.004 |
| 4 | 16 | 4624799 | rs574569398 | C | G | C16orf96 | . | 3.62 | 2.28 | 264 | 232 | 1 | 2 | 2 | 0.001 |
| 4 | 16 | 4644389 | rs139232890 | CAGG | C | C16orf96 | . | 3.62 | 2.28 | 264 | 232 | 1 | 2 | 2 | 0.003 |
| 4 | 16 | 57935248 | rs374813501 | C | G | CNGB1 | D | 3.62 | 4.55 | 528 | 464 | 1 | 4 | 4 | 0.0069 |
| 4 | 16 | 57984441 | rs146170855 | C | T | CNGB1 | . | 3.62 | 4.55 | 528 | 464 | 1 | 4 | 4 | 0.002 |
| 4 | 16 | 57993840 | rs201703193 | C | T | CNGB1 | D | 3.62 | 4.55 | 528 | 464 | 1 | 4 | 4 | 0.001 |
| 4 | 16 | 57996967 | rs570828500 | G | A | CNGB1 | D | 3.62 | 4.55 | 528 | 464 | 1 | 4 | 4 | 0.003 |
| 4 | 1 | 6638781 | rs201116489 | C | T | TAS1R1 | D | 2.72 | 1.71 | 264 | 232 | 2 | 3 | 3 | 0.003 |
| 4 | 1 | 6638995 | rs150612979 | C | T | TAS1R1 | D | 2.72 | 1.71 | 264 | 232 | 2 | 3 | 3 | 0.006 |
| 4 | 16 | 75642789 | rs191524413 | G | C | ADAT1 | D | 2.72 | . | 264 | 232 | 0 | 3 | 3 | 0.003 |
| 4 | 16 | 75646659 | rs536106427 | A | T | ADAT1 | D | 2.72 | . | 264 | 232 | 0 | 3 | 3 | 0.001 |
| 4 | 16 | 84476135 | rs189678245 | A | G | ATP2C2 | D | 3.62 | 2.28 | 396 | 348 | 1 | 2 | 2 | 0.001 |
| 4 | 16 | 84482136 | rs138818397 | A | G | ATP2C2 | . | 3.62 | 2.28 | 396 | 348 | 1 | 2 | 2 | 0.0089 |
| 4 | 16 | 84485620 | rs544756548 | C | T | ATP2C2 | D | 3.62 | 2.28 | 396 | 348 | 1 | 2 | 2 | 0.001 |
| 4 | 17 | 10429123 | rs187438258 | G | A | MYH2 | D | 3.62 | 4.55 | 264 | 232 | 1 | 4 | 4 | 0.002 |
| 4 | 17 | 10432499 | rs150830535 | T | C | MYH2 | D | 3.62 | 4.55 | 264 | 232 | 1 | 4 | 4 | 0.002 |
| 4 | 17 | 10541353 | rs201166774 | G | A | MYH3 | . | 1.81 | . | 264 | 232 | 0 | 4 | 4 | 0.006 |
| 4 | 17 | 10558169 | rs374786690 | G | C | MYH3 | . | 1.81 | . | 264 | 232 | 0 | 4 | 4 | 0.002 |

TABLE 5-continued

Candidate variant list from RA versus control comparison.

| group | chr | pos | id | ref | alt | gene | LR | Gene burden ratio KG East Asia | Gene burden ratio healthy Ctrl | Total No. of alleles in gene healthy Ctrl | Total No. of alleles in gene RA | No. alt alleles in genes healthy Ctrl | No. alt alleles in genes RA | No. of cases with alt alleles | Variant allele frequency KG East Asia |
|---|---|---|---|---|---|---|---|---|---|---|---|---|---|---|---|
| 4 | 17 | 15554781 | rs140413277 | G | T | TRIM16 | . | 1.81 | 2.28 | 132 | 116 | 1 | 2 | 2 | 0.0089 |
| 4 | 17 | 19246867 | rs7221577 | T | C | B9D1 | . | 6.34 | 1.99 | 396 | 348 | 4 | 7 | 7 | 0.0079 |
| 4 | 17 | 19246919 | rs556859873 | G | T | B9D1 | . | 6.34 | 1.99 | 396 | 348 | 4 | 7 | 7 | 0.005 |
| 4 | 17 | 19247075 | rs4924987 | G | A | B9D1 | . | 6.34 | 1.99 | 396 | 348 | 4 | 7 | 7 | 0.004 |
| 4 | 17 | 26856125 | rs188424977 | G | A | FOXN1 | D | 1.81 | 3.41 | 396 | 348 | 1 | 3 | 3 | 0.002 |
| 4 | 17 | 26861343 | rs200401045 | C | T | FOXN1 | . | 1.81 | 3.41 | 396 | 348 | 1 | 3 | 3 | 0.001 |
| 4 | 17 | 26864171 | rs187814037 | C | T | FOXN1 | D | 1.81 | 3.41 | 396 | 348 | 1 | 3 | 3 | 0.005 |
| 4 | 17 | 27233472 | rs200441251 | T | C | PHF12 | D | 1.81 | 2.28 | 396 | 348 | 1 | 2 | 2 | 0.001 |
| 4 | 17 | 27234599 | rs368783828 | G | A | PHF12 | . | 1.81 | 2.28 | 396 | 348 | 1 | 2 | 2 | 0.001 |
| 4 | 17 | 27240924 | rs189300962 | G | C | PHF12 | D | 1.81 | 2.28 | 396 | 348 | 1 | 2 | 2 | 0.002 |
| 4 | 17 | 29226507 | rs201170896 | C | T | TEFM | D | 7.24 | 1.52 | 132 | 116 | 3 | 4 | 4 | 0.004 |
| 4 | 17 | 3417212 | rs547743528 | T | C | TRPV3 | . | 2.72 | 3.41 | 264 | 232 | 1 | 3 | 3 | 0.001 |
| 4 | 17 | 3417877 | rs112791047 | G | A | TRPV3 | . | 2.72 | 3.41 | 264 | 232 | 1 | 3 | 3 | 0.004 |
| 4 | 17 | 38792637 | rs199790447 | C | G | SMARCE1 | . | 1.81 | . | 132 | 116 | 0 | 3 | 3 | 0.004 |
| 4 | 17 | 38975376 | rs565976410 | C | G | KRT10 | D | 1.81 | 2.28 | 264 | 232 | 1 | 2 | 2 | 0.002 |
| 4 | 17 | 38977344 | rs200239146 | G | A | KRT10 | D | 1.81 | 2.28 | 264 | 232 | 1 | 2 | 2 | 0.001 |
| 4 | 17 | 39884092 | . | G | A | HAP1 | . | 5.43 | 1.71 | 264 | 232 | 2 | 3 | 3 | 0.003 |
| 4 | 17 | 39890576 | . | C | T | HAP1 | . | 5.43 | 1.71 | 264 | 232 | 2 | 3 | 3 | 0.006 |
| 4 | 17 | 46878711 | rs184362955 | G | A | TTLL6 | D | 5.43 | 1.71 | 132 | 116 | 2 | 3 | 3 | 0.001 |
| 4 | 17 | 5347841 | rs192062270 | G | A | DHX33 | . | 1.81 | 3.98 | 396 | 348 | 2 | 7 | 7 | 0.004 |
| 4 | 17 | 5364438 | rs192014491 | G | A | DHX33 | . | 1.81 | 3.98 | 396 | 348 | 2 | 7 | 7 | 0.003 |
| 4 | 17 | 5371883 | rs16954727 | C | G | DHX33 | . | 1.81 | 3.98 | 396 | 348 | 2 | 7 | 7 | 0.0099 |

TABLE 5-continued

Candidate variant list from RA versus control comparison.

| group | chr | pos | id | ref | alt | gene | LR | Gene burden ratio | | Total No. of alleles in gene | | No. alt alleles in genes | | No. of cases with alt alleles | Variant allele frequency |
| --- | --- | --- | --- | --- | --- | --- | --- | --- | --- | --- | --- | --- | --- | --- | --- |
| | | | | | | | | KG East Asia | healthy Ctrl | healthy Ctrl | RA | healthy Ctrl | RA | | KG East Asia |
| 4 | 17 | 64216866 | rs181936071 | A | C | APOH | . | 3.62 | 2.28 | 264 | 232 | 1 | 2 | 2 | 0.0069 |
| 4 | 17 | 64219860 | rs373658444 | CA | C | APOH | . | 3.62 | 2.28 | 264 | 232 | 1 | 2 | 2 | 0.0069 |
| 4 | 17 | 6542267 | rs145492116 | A | G | TXNDC17 | . | 5.43 | 1.71 | 132 | 116 | 2 | 3 | 3 | 0.0069 |
| 4 | 17 | 67079395 | rs117323775 | G | T | ABCA6 | D | 1.63 | 1.64 | 254 | 232 | 2 | 3 | 3 | 0.001 |
| 4 | 17 | 67121109 | rs200376492 | A | G | ABCA6 | D | 1.63 | 1.64 | 254 | 232 | 2 | 3 | 3 | 0.0079 |
| 4 | 17 | 67246623 | rs559974558 | G | A | ABCA5 | D | 2.9 | 1.5 | 652 | 580 | 6 | 8 | 8 | 0.001 |
| 4 | 17 | 67247973 | rs201343208 | G | A | ABCA5 | D | 2.9 | 1.5 | 652 | 580 | 6 | 8 | 8 | 0.001 |
| 4 | 17 | 67250466 | rs199641093 | C | T | ABCA5 | D | 2.9 | 1.5 | 652 | 580 | 6 | 8 | 8 | 0.004 |
| 4 | 17 | 67299017 | rs201944918 | A | G | ABCA5 | D | 2.9 | 1.5 | 652 | 580 | 6 | 8 | 8 | 0.0079 |
| 4 | 17 | 67305519 | rs199888749 | G | A | ABCA5 | D | 2.9 | 1.5 | 652 | 580 | 6 | 8 | 8 | 0.0079 |
| 4 | 17 | 73827216 | rs140184929 | C | T | UNC13D | D | 5.43 | . | 264 | 232 | 0 | 3 | 3 | 0.006 |
| 4 | 17 | 73839609 | rs527842266 | C | G | UNC13D | . | 5.43 | . | 264 | 232 | 0 | 3 | 3 | 0.002 |
| 4 | 17 | 7701543 | rs141742705 | G | A | DNAH2 | D | 1.81 | 2.28 | 396 | 348 | 1 | 2 | 2 | 0.001 |
| 4 | 17 | 7705344 | rs8073196 | G | C | DNAH2 | . | 1.81 | 2.28 | 396 | 348 | 1 | 2 | 2 | 0.001 |
| 4 | 17 | 7736250 | rs201527036 | G | A | DNAH2 | . | 1.81 | 2.28 | 396 | 348 | 3 | 4 | 2 | 0.001 |
| 4 | 17 | 79684531 | rs201577202 | C | T | SLC25A10 | D | 3.62 | 1.52 | 264 | 232 | 3 | 4 | 4 | 0.001 |
| 4 | 17 | 79684871 | rs77609145 | A | T | SLC25A10 | . | 3.62 | 1.52 | 264 | 232 | 3 | 4 | 4 | 0.006 |
| 4 | 18 | 2707800 | rs184984483 | C | T | SMCHD1 | D | 5.48 | 3.37 | 258 | 230 | 1 | 3 | 3 | 0.001 |
| 4 | 18 | 2777922 | rs527648000 | C | T | SMCHD1 | . | 5.48 | 3.37 | 258 | 230 | 1 | 3 | 3 | 0.005 |
| 4 | 18 | 28911778 | rs147775289 | T | C | DSG1 | D | 5.43 | 1.71 | 528 | 464 | 2 | 3 | 3 | 0.003 |
| 4 | 18 | 28934293 | rs149191001 | C | T | DSG1 | . | 5.43 | 1.71 | 528 | 464 | 2 | 3 | 3 | 0.001 |
| 4 | 18 | 28934674 | rs181411154 | G | A | DSG1 | D | 5.43 | 1.71 | 528 | 464 | 2 | 3 | 3 | 0.001 |

TABLE 5-continued

Candidate variant list from RA versus control comparison.

| group | chr | pos | id | ref | alt | gene | LR | Gene burden ratio KG East Asia | Gene burden ratio healthy Ctrl | Total No. of alleles in gene healthy Ctrl | Total No. of alleles in gene RA | No. alt alleles in genes healthy Ctrl | No. alt alleles in genes RA | No. of cases with alt alleles | Variant allele frequency KG East Asia |
|---|---|---|---|---|---|---|---|---|---|---|---|---|---|---|---|
| 4 | 18 | 28934927 | rs148488583 | C | G | DSG1 | D | 5.43 | 1.71 | 528 | 464 | 2 | 3 | 3 | 0.004 |
| 4 | 18 | 580853 | rs114933134 | G | A | CETN1 | D | 3.62 | . | 132 | 116 | 0 | 4 | 4 | 0.005 |
| 4 | 18 | 61160178 | rs370525785 | T | C | SERPINB5 | . | 3.62 | 2.28 | 264 | 232 | 1 | 2 | 2 | 0.001 |
| 4 | 18 | 61170818 | rs185364126 | G | A | SERPINB5 | D | 3.62 | 2.28 | 264 | 232 | 1 | 2 | 2 | 0.002 |
| 4 | 18 | 61305002 | rs201297323 | T | C | SERPINB4 | . | 1.81 | 3.41 | 264 | 232 | 1 | 3 | 3 | 0.0069 |
| 4 | 18 | 61305289 | rs188021365 | A | T | SERPINB4 | . | 1.81 | 3.41 | 264 | 232 | 1 | 3 | 3 | 0.005 |
| 4 | 1 | 87380851 | rs546745 | A | G | HS2ST1 | . | 3.62 | 2.28 | 264 | 232 | 1 | 2 | 2 | 0.006 |
| 4 | 1 | 87563514 | rs143260332 | G | A | HS2ST1 | . | 3.62 | 2.28 | 264 | 232 | 1 | 2 | 2 | 0.004 |
| 4 | 18 | 76886315 | rs200431802 | C | T | ATP9B | D | 3.62 | 2.28 | 264 | 232 | 1 | 2 | 2 | 0.004 |
| 4 | 18 | 77096664 | rs201172611 | G | A | ATP9B | . | 3.62 | 2.28 | 264 | 232 | 1 | 2 | 2 | 0.001 |
| 4 | 18 | 9549345 | rs199964908 | G | A | PPP4R1 | D | 2.72 | 1.71 | 132 | 116 | 2 | 3 | 3 | 0.0079 |
| 4 | 19 | 14071095 | rs140301367 | G | A | DCAF15 | . | 5.43 | 3.41 | 132 | 116 | 1 | 3 | 3 | 0.0079 |
| 4 | 19 | 15285063 | rs141320511 | G | T | NOTCH3 | D | 4.53 | 5.69 | 396 | 348 | 1 | 5 | 5 | 0.0099 |
| 4 | 19 | 15298126 | rs201118034 | G | A | NOTCH3 | . | 4.53 | 5.69 | 396 | 348 | 1 | 5 | 5 | 0.001 |
| 4 | 19 | 15302951 | rs202157633 | G | A | NOTCH3 | . | 4.53 | 5.69 | 396 | 348 | 1 | 5 | 5 | 0.005 |
| 4 | 19 | 39367429 | rs58188607 | G | A | RINL | . | 3.62 | 2.28 | 132 | 116 | 1 | 2 | 2 | 0.006 |
| 4 | 19 | 44662139 | rs201230189 | G | A | ZNF234 | D | 1.81 | 2.28 | 132 | 116 | 1 | 2 | 2 | 0.004 |
| 4 | 19 | 41837123 | rs199982059 | C | T | TGFβ1 | . | 1.81 | . | 132 | 116 | 0 | 4 | 4 | 0.006 |
| 4 | 19 | 46184983 | rs186639840 | A | T | GIPR | . | 1.81 | 2.28 | 132 | 116 | 1 | 2 | 2 | 0.0069 |
| 4 | 19 | 46242968 | rs183304235 | G | C | BHMG1 | D | 2.72 | . | 132 | 116 | 0 | 3 | 3 | 0.0069 |
| 4 | 19 | 51470542 | rs201586262 | G | T | KLK6 | D | 5.43 | . | 132 | 116 | 0 | 3 | 3 | 0.001 |
| 4 | 1 | 95303290 | rs140889980 | G | A | SLC44A3 | . | 1.81 | . | 264 | 232 | 0 | 3 | 3 | 0.004 |

TABLE 5-continued

Candidate variant list from RA versus control comparison.

| group | chr | pos | id | ref | alt | gene | LR | Gene burden ratio KG East Asia | Gene burden ratio healthy Ctrl | Total No. of alleles in gene healthy Ctrl | Total No. of alleles in gene RA | No. alt alleles in genes healthy Ctrl | No. alt alleles in genes RA | No. of cases with alt alleles | Variant allele frequency KG East Asia |
|---|---|---|---|---|---|---|---|---|---|---|---|---|---|---|---|
| 4 | 1 | 95322899 | rs184943086 | C | T | SLC44A3 | . | 1.81 | . | 264 | 232 | 0 | 3 | 3 | 0.002 |
| 4 | 19 | 8140232 | rs145316149 | G | A | FBN3 | D | 1.81 | 3.41 | 528 | 464 | 1 | 3 | 3 | 0.004 |
| 4 | 19 | 8150331 | rs142940013 | G | A | FBN3 | D | 1.81 | 3.41 | 528 | 464 | 1 | 3 | 3 | 0.004 |
| 4 | 19 | 8155130 | rs183278638 | G | A | FBN3 | D | 1.81 | 3.41 | 528 | 464 | 1 | 3 | 3 | 0.002 |
| 4 | 19 | 8188820 | rs145435433 | C | T | FBN3 | D | 1.81 | 3.41 | 528 | 464 | 1 | 3 | 3 | 0.006 |
| 4 | 19 | 8979212 | rs149481309 | C | T | MUC16 | . | 3.62 | 1.82 | 528 | 464 | 5 | 8 | 8 | 0.0089 |
| 4 | 19 | 9002496 | rs553074376 | C | T | MUC16 | . | 3.62 | 1.82 | 528 | 464 | 5 | 8 | 8 | 0.006 |
| 4 | 19 | 9043416 | rs17417801 | G | A | MUC16 | . | 3.62 | 1.82 | 528 | 464 | 5 | 8 | 8 | 0.0079 |
| 4 | 19 | 9056878 | rs200934751 | GAGA | G | MUC16 | . | 3.62 | 1.82 | 528 | 464 | 5 | 8 | 8 | 0.0069 |
| 4 | 19 | 23433244 | rs146114915 | G | A | CST11 | . | 5.43 | 3.41 | 132 | 116 | 1 | 3 | 3 | 0.0079 |
| 4 | 20 | 34117097 | rs141795719 | G | A | C20orf173 | . | 3.62 | 2.28 | 132 | 116 | 1 | 2 | 2 | 0.006 |
| 4 | 20 | 37394884 | rs141204447 | G | A | ACTR5 | D | 6.34 | 7.97 | 264 | 232 | 1 | 7 | 7 | 0.0069 |
| 4 | 20 | 37400374 | rs3752289 | C | T | ACTR5 | D | 6.34 | 7.97 | 264 | 232 | 1 | 7 | 7 | 0.0089 |
| 4 | 20 | 39788407 | rs201733074 | T | C | PLCG1 | . | 1.81 | 6.83 | 396 | 348 | 1 | 6 | 6 | 0.0079 |
| 4 | 20 | 39797820 | rs547025579 | GACCAGAACC (SEQ ID NO: 1) | G | PLCG1 | . | 1.81 | 6.83 | 396 | 348 | 1 | 6 | 6 | 0.0069 |
| 4 | 20 | 39799092 | rs183538599 | C | T | PLCG1 | . | 1.81 | 6.83 | 396 | 348 | 1 | 6 | 6 | 0.0079 |
| 4 | 20 | 39974514 | rs201526389 | C | T | LPIN3 | D | 3.62 | 2.28 | 396 | 348 | 1 | 2 | 2 | 0.0079 |
| 4 | 20 | 39981270 | rs200870645 | C | G | LPIN3 | D | 3.62 | 2.28 | 396 | 348 | 1 | 2 | 2 | 0.002 |
| 4 | 20 | 39987396 | rs202035187 | T | C | LPIN3 | D | 3.62 | 2.28 | 396 | 348 | 1 | 2 | 2 | 0.003 |
| 4 | 20 | 40052247 | rs569454917 | C | G | CHD6 | . | 3.62 | 2.28 | 264 | 232 | 1 | 2 | 2 | 0.001 |
| 4 | 20 | 40161851 | rs75576471 | C | G | CHD6 | . | 3.62 | 2.28 | 264 | 232 | 1 | 2 | 2 | 0.0069 |

TABLE 5-continued

Candidate variant list from RA versus control comparison.

| group | chr | pos | id | ref | alt | gene | LR | Gene burden ratio KG East Asia | Gene burden ratio healthy Ctrl | Total No. of alleles in gene healthy Ctrl | Total No. of alleles in gene RA | No. alt alleles in genes healthy Ctrl | No. alt alleles in genes RA | No. of cases with alt alleles | Variant allele frequency KG East Asia |
|---|---|---|---|---|---|---|---|---|---|---|---|---|---|---|---|
| 4 | 20 | 45839448 | rs144592314 | G | A | ZMYND8 | D | 3.62 | 2.28 | 132 | 116 | 1 | 2 | 2 | 0.003 |
| 4 | 2 | 101093702 | rs149056157 | C | T | NMS | . | 1.81 | . | 132 | 116 | 0 | 5 | 5 | 0.0079 |
| 4 | 2 | 11295694 | rs372049512 | C | A | PQLC3 | D | 1.81 | 2.28 | 132 | 116 | 1 | 2 | 2 | 0.004 |
| 4 | 2 | 118577378 | rs145263993 | A | C | DDX18 | . | 5.43 | 1.71 | 132 | 116 | 2 | 3 | 3 | 0.004 |
| 4 | 21 | 34018908 | rs115353088 | A | T | SYNJ1 | D | 2.41 | 2.26 | 394 | 348 | 2 | 4 | 4 | 0.001 |
| 4 | 21 | 34045841 | rs115989459 | G | A | SYNJ1 | . | 2.41 | 2.26 | 394 | 348 | 2 | 4 | 4 | 0.003 |
| 4 | 21 | 34048669 | rs533995497 | T | C | SYNJ1 | . | 2.41 | 2.26 | 394 | 348 | 2 | 4 | 4 | 0.001 |
| 4 | 21 | 38072227 | rs200569203 | G | A | SIM2 | D | 1.81 | 2.28 | 264 | 232 | 1 | 2 | 2 | 0.001 |
| 4 | 21 | 38098456 | rs201356831 | T | C | SIM2 | . | 1.81 | 2.28 | 264 | 232 | 1 | 2 | 2 | 0.001 |
| 4 | 2 | 141115543 | rs77178150 | C | T | LRP1B | D | 2.72 | 3.41 | 396 | 348 | 1 | 3 | 3 | 0.0089 |
| 4 | 2 | 141253160 | rs572325724 | T | A | LRP1B | . | 2.72 | 3.41 | 396 | 348 | 1 | 3 | 3 | 0.002 |
| 4 | 2 | 141458125 | rs369842040 | G | A | LRP1B | D | 2.72 | 3.41 | 396 | 348 | 1 | 3 | 3 | 0.001 |
| 4 | 21 | 47571485 | rs199508525 | C | T | FTCD | D | 1.81 | 3.41 | 132 | 116 | 1 | 3 | 3 | 0.0069 |
| 4 | 2 | 178534249 | rs142433460 | T | A | PDE11A | D | 7.24 | 4.55 | 264 | 232 | 1 | 4 | 4 | 0.004 |
| 4 | 2 | 178562138 | rs201572288 | A | T | PDE11A | D | 7.24 | 4.55 | 264 | 232 | 1 | 4 | 4 | 0.002 |
| 4 | 2 | 179404792 | rs556524594 | C | T | TTN | . | 3.02 | 1.9 | 1056 | 928 | 3 | 5 | 5 | 0.001 |
| 4 | 2 | 179425208 | rs142478636 | G | T | TTN | D | 3.02 | 1.9 | 1056 | 928 | 3 | 5 | 5 | 0.004 |
| 4 | 2 | 179430305 | rs185887755 | G | A | TTN | D | 3.02 | 1.9 | 1056 | 928 | 3 | 5 | 5 | 0.003 |
| 4 | 2 | 179437342 | rs567446185 | C | T | TTN | D | 3.02 | 1.9 | 1056 | 928 | 3 | 5 | 5 | 0.001 |
| 4 | 2 | 179481839 | rs144688960 | C | A | TTN | . | 3.02 | 1.9 | 1056 | 928 | 3 | 5 | 5 | 0.001 |
| 4 | 2 | 179504772 | rs551963261 | C | T | TTN | D | 3.02 | 1.9 | 1056 | 928 | 3 | 5 | 5 | 0.001 |
| 4 | 2 | 179577222 | rs186857044 | C | A | TTN | D | 3.02 | 1.9 | 1056 | 928 | 3 | 5 | 5 | 0.001 |

TABLE 5-continued

Candidate variant list from RA versus control comparison.

| group | chr | pos | id | ref | alt | gene | LR | Gene burden ratio KG East Asia | Gene burden ratio healthy Ctrl | Total No. of alleles in gene healthy Ctrl | Total No. of alleles in gene RA | No. alt alleles in genes healthy Ctrl | No. alt alleles in genes RA | No. of cases with alt alleles | Variant allele frequency KG East Asia |
|---|---|---|---|---|---|---|---|---|---|---|---|---|---|---|---|
| 4 | 2 | 179585717 | rs367826445 | C | T | TTN | D | 3.02 | 1.9 | 1056 | 928 | 3 | 5 | 5 | 0.002 |
| 4 | 2 | 196718225 | rs139835496 | G | A | DNAH7 | . | 2.72 | . | 132 | 116 | 0 | 3 | 3 | 0.005 |
| 4 | 2 | 202356803 | rs557048083 | G | A | ALS2CR11 | . | 2.72 | . | 264 | 232 | 0 | 3 | 3 | 0.001 |
| 4 | 2 | 202467972 | rs148342903 | C | G | ALS2CR11 | D | 2.72 | . | 264 | 232 | 0 | 3 | 3 | 0.0069 |
| 4 | 2 | 203058233 | rs13024221 | T | C | KIAA2012 | . | 7.3 | 4.59 | 264 | 230 | 1 | 4 | 4 | 0.003 |
| 4 | 2 | 203059076 | rs141298049 | G | A | KIAA2012 | . | 7.3 | 4.59 | 264 | 230 | 1 | 4 | 4 | 0.006 |
| 4 | 2 | 208477907 | rs192886645 | G | A | METTL21A | . | 3.62 | 2.28 | 132 | 116 | 1 | 2 | 2 | 0.002 |
| 4 | 2 | 213921827 | rs150075012 | T | C | IKZF2 | . | 2.72 | 1.71 | 132 | 116 | 1 | 3 | 3 | 0.0089 |
| 4 | 2 | 219029361 | rs201920477 | C | T | CXCR1 | D | 3.62 | 2.28 | 132 | 116 | 2 | 2 | 2 | 0.004 |
| 4 | 2 | 219864729 | rs146133764 | G | A | TXNRD2 | . | 2.72 | 3.41 | 396 | 348 | 1 | 3 | 3 | 0.004 |
| 4 | 2 | 219868190 | rs184640901 | C | G | TXNRD2 | . | 2.72 | 3.41 | 396 | 348 | 1 | 3 | 3 | 0.002 |
| 4 | 2 | 219870857 | rs147383232 | G | A | TXNRD2 | . | 2.72 | 3.41 | 396 | 348 | 1 | 3 | 3 | 0.0089 |
| 4 | 2 | 26159232 | rs79294358 | C | T | MYO18B | D | 2.41 | 4.55 | 396 | 348 | 1 | 4 | 4 | 0.0079 |
| 4 | 22 | 26166958 | rs117430010 | C | T | MYO18B | . | 2.41 | 4.55 | 396 | 348 | 1 | 4 | 4 | 0.006 |
| 4 | 22 | 26264278 | rs137859315 | T | C | MYO18B | . | 2.41 | 4.55 | 396 | 348 | 1 | 4 | 4 | 0.0079 |
| 4 | 22 | 227872169 | rs192411379 | T | C | COL4A4 | D | 2.72 | 3.4 | 526 | 464 | 1 | 3 | 3 | 0.001 |
| 4 | 2 | 227920837 | rs199710625 | A | G | COL4A4 | . | 2.72 | 3.4 | 526 | 464 | 1 | 3 | 3 | 0.004 |
| 4 | 2 | 227967506 | rs373741172 | C | T | COL4A4 | D | 2.72 | 3.4 | 526 | 464 | 1 | 3 | 3 | 0.001 |
| 4 | 2 | 227985873 | rs190570269 | G | C | COL4A4 | . | 2.72 | 3.4 | 526 | 464 | 1 | 3 | 3 | 0.006 |
| 4 | 22 | 29881766 | rs201416955 | G | A | NEFH | D | 1.81 | 2.28 | 264 | 232 | 1 | 2 | 2 | 0.003 |
| 4 | 22 | 29881844 | rs117036372 | G | A | NEFH | . | 1.81 | 2.28 | 264 | 232 | 1 | 2 | 2 | 0.006 |
| 4 | 22 | 31522450 | rs150976596 | G | A | INPP5J | D | 3.62 | 1.9 | 264 | 232 | 3 | 5 | 5 | 0.0099 |

TABLE 5-continued

Candidate variant list from RA versus control comparison.

| group | chr | pos | id | ref | alt | gene | LR | Gene burden ratio KG East Asia | Gene burden ratio healthy Ctrl | Total No. of alleles in gene healthy Ctrl | Total No. of alleles in gene RA | No. alt alleles in genes healthy Ctrl | No. alt alleles in genes RA | No. of cases with alt alleles | Variant allele frequency KG East Asia |
|---|---|---|---|---|---|---|---|---|---|---|---|---|---|---|---|
| 4 | 22 | 31522715 | rs370874308 | A | T | INPP5J | . | 3.62 | 1.9 | 264 | 232 | 3 | 5 | 5 | 0.003 |
| 4 | 22 | 32614713 | rs78144589 | C | T | SLC5A4 | . | 5.43 | 6.83 | 264 | 232 | 1 | 6 | 6 | 0.0099 |
| 4 | 22 | 32631002 | rs554791323 | T | C | SLC5A4 | D | 5.43 | 6.83 | 264 | 232 | 1 | 6 | 6 | 0.001 |
| 4 | 2 | 234835171 | rs188545335 | G | A | TRPM8 | . | 1.81 | 2.28 | 264 | 232 | 1 | 2 | 2 | 0.002 |
| 4 | 2 | 234890409 | rs202160114 | T | C | TRPM8 | . | 1.81 | 2.28 | 264 | 232 | 1 | 2 | 2 | 0.001 |
| 4 | 2 | 242046783 | rs199503351 | G | A | PASK | . | 5.43 | 3.41 | 396 | 348 | 1 | 3 | 3 | 0.002 |
| 4 | 2 | 242047581 | rs563432464 | C | A | PASK | . | 5.43 | 3.41 | 396 | 348 | 1 | 3 | 3 | 0.001 |
| 4 | 2 | 242089016 | rs187718988 | G | C | PASK | . | 5.43 | 3.41 | 396 | 348 | 1 | 3 | 3 | 0.001 |
| 4 | 2 | 242695306 | rs149628174 | C | T | D2HGDH | D | 4.53 | 2.84 | 132 | 116 | 2 | 5 | 5 | 0.0099 |
| 4 | 2 | 43926729 | rs201816198 | C | A | EFCAB6 | . | 1.63 | 3.41 | 264 | 232 | 1 | 3 | 3 | 0.0079 |
| 4 | 2 | 44030977 | rs181939688 | G | C | EFCAB6 | . | 1.63 | 3.41 | 264 | 232 | 1 | 3 | 3 | 0.001 |
| 4 | 22 | 46664409 | rs144175578 | A | G | TTC38 | . | 3.62 | . | 264 | 232 | 0 | 4 | 4 | 0.0099 |
| 4 | 22 | 46684376 | rs202139216 | C | T | TTC38 | . | 3.62 | . | 264 | 232 | 0 | 4 | 4 | 0.001 |
| 4 | 22 | 51041663 | rs41282359 | C | A | MAPK8IP2 | . | 4.53 | 2.84 | 924 | 812 | 2 | 5 | 5 | 0.002 |
| 4 | 22 | 51042484 | rs56314791 | C | T | MAPK8IP2 | . | 4.53 | 2.84 | 924 | 812 | 2 | 5 | 5 | 0.002 |
| 4 | 22 | 51042861 | rs9616795 | C | G | MAPK8IP2 | . | 4.53 | 2.84 | 924 | 812 | 2 | 5 | 5 | 0.004 |
| 4 | 22 | 51042864 | rs571810591 | G | C | MAPK8IP2 | . | 4.53 | 2.84 | 924 | 812 | 2 | 5 | 5 | 0.001 |
| 4 | 22 | 51043374 | rs550444582 | G | A | MAPK8IP2 | . | 4.53 | 2.84 | 924 | 812 | 2 | 5 | 5 | 0.002 |
| 4 | 22 | 51044243 | rs916005 | C | T | MAPK8IP2 | . | 4.53 | 2.84 | 924 | 812 | 2 | 5 | 5 | 0.004 |
| 4 | 22 | 51045178 | rs200208943 | C | T | MAPK8IP2 | . | 4.53 | 2.84 | 924 | 812 | 2 | 5 | 5 | 0.001 |
| 4 | 2 | 27721143 | rs146175795 | G | A | GCKR | D | 5.43 | 3.41 | 264 | 232 | 1 | 3 | 3 | 0.0069 |
| 4 | 2 | 27730834 | rs200225266 | C | T | GCKR | . | 5.43 | 3.41 | 264 | 232 | 1 | 3 | 3 | 0.004 |

TABLE 5-continued

Candidate variant list from RA versus control comparison.

| group | chr | pos | id | ref | alt | gene | LR | Gene burden ratio KG East Asia | Gene burden ratio healthy Ctrl | Total No. of alleles in gene healthy Ctrl | Total No. of alleles in gene RA | No. alt alleles in genes healthy Ctrl | No. alt alleles in genes RA | No. of cases with alt alleles | Variant allele frequency KG East Asia |
|---|---|---|---|---|---|---|---|---|---|---|---|---|---|---|---|
| 4 | 2 | 31751329 | rs9332966 | G | C | SRD5A2 | . | 1.81 | 2.28 | 264 | 232 | 1 | 2 | 2 | 0.005 |
| 4 | 2 | 31805775 | rs550866120 | C | T | SRD5A2 | . | 1.81 | 2.28 | 264 | 232 | 1 | 2 | 2 | 0.003 |
| 4 | 2 | 46588019 | rs150877473 | C | G | EPAS1 | . | 2.72 | 3.41 | 264 | 232 | 1 | 3 | 3 | 0.0099 |
| 4 | 2 | 46603672 | rs187543960 | C | G | EPAS1 | . | 2.72 | 3.41 | 264 | 232 | 1 | 3 | 3 | 0.004 |
| 4 | 2 | 65571844 | rs182442107 | T | C | SPRED2 | . | 3.62 | 2.28 | 132 | 116 | 1 | 2 | 2 | 0.002 |
| 4 | 2 | 98165911 | rs1839230 | T | C | ANKRD36B | . | 3.62 | . | 132 | 116 | 0 | 4 | 4 | 0.0069 |
| 4 | 3 | 108147410 | rs552849827 | T | C | MYH15 | D | 3.02 | 1.86 | 518 | 464 | 3 | 5 | 5 | 0.001 |
| 4 | 3 | 108178230 | rs560378764 | G | A | MYH15 | D | 3.02 | 1.86 | 518 | 464 | 3 | 5 | 5 | 0.001 |
| 4 | 3 | 108219046 | rs182324086 | C | A | MYH15 | D | 3.02 | 1.86 | 518 | 464 | 3 | 5 | 5 | 0.001 |
| 4 | 3 | 108220556 | rs368131843 | C | T | MYH15 | D | 3.02 | 1.86 | 518 | 464 | 3 | 5 | 5 | 0.006 |
| 4 | 3 | 121713035 | rs142746163 | G | A | ILDR1 | . | 1.81 | . | 264 | 232 | 0 | 3 | 3 | 0.0099 |
| 4 | 3 | 121724081 | rs200883040 | C | G | ILDR1 | . | 1.81 | . | 264 | 232 | 0 | 3 | 3 | 0.003 |
| 4 | 3 | 124485068 | rs200221434 | C | T | ITGB5 | . | 2.72 | . | 396 | 348 | 0 | 3 | 3 | 0.002 |
| 4 | 3 | 124492606 | rs140023830 | G | A | ITGB5 | D | 2.72 | . | 396 | 348 | 0 | 3 | 3 | 0.0079 |
| 4 | 3 | 124567399 | rs28372859 | T | A | ITGB5 | D | 2.72 | . | 396 | 348 | 0 | 3 | 3 | 0.002 |
| 4 | 3 | 124716667 | rs181022733 | G | T | HEG1 | D | 7.24 | 2.28 | 396 | 348 | 2 | 4 | 4 | 0.003 |
| 4 | 3 | 124731800 | rs183321802 | T | A | HEG1 | D | 7.24 | 2.28 | 396 | 348 | 2 | 4 | 4 | 0.004 |
| 4 | 3 | 124738285 | rs200164121 | G | C | HEG1 | D | 7.24 | 2.28 | 396 | 348 | 2 | 4 | 4 | 0.0079 |
| 4 | 3 | 130120633 | rs370632529 | T | G | COL6A5 | D | 3.62 | 1.52 | 528 | 464 | 3 | 4 | 4 | 0.002 |
| 4 | 3 | 130124457 | rs537224684 | A | G | COL6A5 | D | 3.62 | 1.52 | 528 | 464 | 3 | 4 | 4 | 0.001 |
| 4 | 3 | 130145236 | rs202221090 | G | A | COL6A5 | D | 3.62 | 1.52 | 528 | 464 | 3 | 4 | 4 | 0.003 |
| 4 | 3 | 130150614 | rs79358579 | C | T | COL6A5 | D | 3.62 | 1.52 | 528 | 464 | 3 | 4 | 4 | 0.003 |

TABLE 5-continued

Candidate variant list from RA versus control comparison.

| group | chr | pos | id | ref | alt | gene | LR | Gene burden ratio KG East Asia | Gene burden ratio healthy Ctrl | Total No. of alleles in gene healthy Ctrl | Total No. of alleles in gene RA | No. alt alleles in genes healthy Ctrl | No. alt alleles in genes RA | No. of cases with alt alleles | Variant allele frequency KG East Asia |
|---|---|---|---|---|---|---|---|---|---|---|---|---|---|---|---|
| 4 | 3 | 13420488 | rs200748145 | T | C | NUP210 | . | 5.43 | . | 132 | 116 | 0 | 3 | 3 | 0.001 |
| 4 | 3 | 154861227 | rs2304504 | C | T | MME | . | 5.43 | 1.71 | 396 | 348 | 2 | 3 | 3 | 0.003 |
| 4 | 3 | 154861228 | rs182602615 | G | A | MME | . | 5.43 | 1.71 | 396 | 348 | 2 | 3 | 3 | 0.003 |
| 4 | 3 | 154886310 | rs200308077 | G | A | MME | D | 5.43 | 1.71 | 396 | 348 | 2 | 3 | 3 | 0.002 |
| 4 | 3 | 183906578 | rs531703061 | C | T | ABCF3 | D | 5.43 | 4.55 | 264 | 232 | 1 | 4 | 4 | 0.003 |
| 4 | 3 | 183911416 | rs76223160 | G | A | ABCF3 | D | 5.43 | 4.55 | 264 | 232 | 1 | 4 | 4 | 0.006 |
| 4 | 3 | 183952934 | rs374722127 | C | T | VWA5B2 | . | 2.41 | 1.52 | 264 | 232 | 3 | 4 | 4 | 0.001 |
| 4 | 3 | 183957472 | rs565285822 | C | T | VWA5B2 | . | 2.41 | 1.52 | 264 | 232 | 3 | 4 | 4 | 0.0089 |
| 4 | 3 | 186937924 | rs3774266 | C | T | MASP1 | D | 3.62 | 2.28 | 264 | 232 | 1 | 2 | 2 | 0.004 |
| 4 | 3 | 186953975 | rs72549155 | G | C | MASP1 | D | 3.62 | 2.28 | 264 | 232 | 1 | 2 | 2 | 0.003 |
| 4 | 3 | 2928719 | rs184171731 | A | C | CNTN4 | . | 4.53 | 5.69 | 396 | 348 | 1 | 5 | 5 | 0.003 |
| 4 | 3 | 3080611 | rs105110251 | G | C | CNTN4 | . | 4.53 | 5.69 | 396 | 348 | 1 | 5 | 5 | 0.003 |
| 4 | 3 | 3081959 | rs339284 | T | C | CNTN4 | . | 4.53 | 5.69 | 396 | 348 | 1 | 5 | 5 | 0.002 |
| 4 | 3 | 44762826 | rs181738022 | C | T | ZNF502 | D | 2.72 | 3.41 | 264 | 232 | 2 | 6 | 6 | 0.0079 |
| 4 | 3 | 44762827 | rs185260708 | A | T | ZNF502 | D | 2.72 | 3.41 | 264 | 232 | 2 | 6 | 6 | 0.0079 |
| 4 | 3 | 49950176 | rs192575536 | G | A | UBA7 | . | 3.62 | 2.28 | 132 | 116 | 1 | 2 | 2 | 0.002 |
| 4 | 3 | 58107069 | rs76471260 | G | A | FLNB | D | 2.41 | 4.55 | 396 | 348 | 1 | 4 | 4 | 0.002 |
| 4 | 3 | 58109123 | rs199959926 | G | C | FLNB | D | 2.41 | 4.55 | 396 | 348 | 1 | 4 | 4 | 0.006 |
| 4 | 3 | 58134099 | rs143066905 | A | G | FLNB | D | 2.41 | 4.55 | 396 | 348 | 1 | 4 | 4 | 0.0099 |
| 4 | 3 | 62309627 | rs1881268 | G | C | C3orf14 | . | 1.81 | . | 264 | 232 | 0 | 3 | 3 | 0.001 |
| 4 | 3 | 62317022 | rs186089632 | C | A | C3orf14 | . | 1.81 | . | 264 | 232 | 0 | 3 | 3 | 0.003 |
| 4 | 4 | 15599021 | rs117667651 | C | A | CC2D2A | . | 2.72 | . | 132 | 116 | 0 | 3 | 3 | 0.0079 |

TABLE 5-continued

Candidate variant list from RA versus control comparison.

| group | chr | pos | id | ref | alt | gene | LR | Gene burden ratio KG East Asia | Gene burden ratio healthy Ctrl | Total No. of alleles in gene healthy Ctrl | Total No. of alleles in gene RA | No. alt alleles in genes healthy Ctrl | No. alt alleles in genes RA | No. of cases with alt alleles | Variant allele frequency KG East Asia |
|---|---|---|---|---|---|---|---|---|---|---|---|---|---|---|---|
| 4 | 4 | 16168246 | rs2271748 | C | T | TAPT1 | . | 2.9 | 4.55 | 132 | 116 | 1 | 4 | 4 | 0.0099 |
| 4 | 4 | 17842302 | rs527561771 | TAA | T | NCAPG | . | 2.76 | 1.66 | 126 | 114 | 2 | 3 | 3 | 0.0079 |
| 4 | 4 | 26322320 | rs200707132 | A | C | RBPJ | . | 3.62 | 2.28 | 132 | 116 | 1 | 2 | 2 | 0.0079 |
| 4 | 4 | 6596385 | rs32216941 | AC | A | MAN2B2 | . | 5.43 | 3.41 | 132 | 116 | 1 | 3 | 3 | 0.006 |
| 4 | 4 | 674349 | rs376244258 | AC | A | MYL5 | . | 3.62 | 2.28 | 132 | 114 | 1 | 2 | 2 | 0.006 |
| 4 | 4 | 84378118 | rs199634680 | A | AT | MRPS18C | . | 1.84 | 2.32 | 132 | 116 | 1 | 2 | 2 | 0.0079 |
| 4 | 4 | 96762012 | rs144813590 | C | G | PDHA2 | D | 5.43 | . | 132 | 116 | 0 | 3 | 3 | 0.003 |
| 4 | 4 | 983115 | rs143381873 | G | A | SLC26A1 | D | 3.62 | 1.52 | 528 | 464 | 3 | 4 | 4 | 0.005 |
| 4 | 4 | 983342 | rs201608921 | C | T | SLC26A1 | D | 3.62 | 1.52 | 528 | 464 | 3 | 4 | 4 | 0.002 |
| 4 | 4 | 983810 | rs563866785 | G | A | SLC26A1 | D | 3.62 | 1.52 | 528 | 464 | 3 | 4 | 4 | 0.001 |
| 4 | 4 | 984938 | rs139024319 | G | A | SLC26A1 | D | 3.62 | 1.52 | 528 | 464 | 3 | 4 | 4 | 0.002 |
| 4 | 4 | 106716975 | rs201008479 | G | A | EFNA5 | D | 2.41 | . | 132 | 116 | 0 | 4 | 4 | 0.006 |
| 4 | 4 | 118862922 | rs190659146 | T | C | HSD17B4 | . | 3.62 | . | 132 | 116 | 0 | 4 | 4 | 0.005 |
| 4 | 5 | 130815199 | rs187240567 | T | C | RAPGEF6 | . | 3.62 | 2.28 | 264 | 232 | 1 | 2 | 2 | 0.001 |
| 4 | 5 | 130841167 | rs201819833 | G | A | RAPGEF6 | D | 3.62 | 2.28 | 264 | 232 | 1 | 2 | 2 | 0.002 |
| 4 | 5 | 134102599 | rs200408238 | C | G | DDX46 | . | 2.41 | 2.28 | 264 | 232 | 2 | 4 | 4 | 0.001 |
| 4 | 5 | 134143635 | rs200296518 | A | G | DDX46 | . | 2.41 | 2.28 | 264 | 232 | 2 | 4 | 4 | 0.0069 |
| 4 | 5 | 137506607 | rs191895585 | G | A | BRD8 | . | 3.62 | 2.28 | 132 | 116 | 1 | 2 | 2 | 0.005 |
| 4 | 5 | 1495038 | rs201521332 | G | A | LPCAT1 | . | 5.53 | . | 126 | 114 | 0 | 3 | 3 | 0.0069 |
| 4 | 5 | 156675967 | rs34482255 | C | T | ITK | D | 1.81 | 2.28 | 132 | 116 | 1 | 2 | 2 | 0.005 |
| 4 | 5 | 180477285 | rs200084524 | C | T | BTNL9 | . | 1.81 | 1.71 | 264 | 232 | 2 | 3 | 3 | 0.001 |
| 4 | 5 | 180483533 | rs373494500 | T | C | BTNL9 | . | 1.81 | 1.71 | 264 | 232 | 2 | 3 | 3 | 0.0069 |

TABLE 5-continued

Candidate variant list from RA versus control comparison.

| group | chr | pos | id | ref | alt | gene | LR | Gene burden ratio | | Total No. of alleles in gene | | No. alt alleles in genes | | No. of cases with alt alleles | Variant allele frequency KG East Asia |
|---|---|---|---|---|---|---|---|---|---|---|---|---|---|---|---|
| | | | | | | | | KG East Asia | healthy Ctrl | healthy Ctrl | RA | healthy Ctrl | RA | | |
| 4 | 5 | 38337618 | rs376475358 | G | A | EGFLAM | . | 3.62 | 2.28 | 264 | 232 | 1 | 2 | 2 | 0.003 |
| 4 | 5 | 38425202 | rs201409353 | A | G | EGFLAM | . | 3.62 | 2.28 | 264 | 232 | 1 | 2 | 2 | 0.001 |
| 4 | 5 | 43675682 | rs80011859 | C | A | NNT | D | 3.62 | 2.28 | 264 | 232 | 1 | 2 | 2 | 0.002 |
| 4 | 5 | 43677914 | rs144007922 | C | T | NNT | . | 3.62 | 2.28 | 264 | 232 | 1 | 2 | 2 | 0.004 |
| 4 | 5 | 94245090 | rs543643285 | G | GA | MCTP1 | . | 11.05 | 2.28 | 260 | 228 | 6 | 12 | 12 | 0.001 |
| 4 | 5 | 94259730 | rs555638017 | GAAAC | G | MCTP1 | . | 11.05 | 2.28 | 260 | 228 | 6 | 12 | 12 | 0.006 |
| 4 | 5 | 95226800 | rs560418641 | C | T | ELL2 | . | 1.81 | 2.28 | 264 | 232 | 1 | 2 | 2 | 0.001 |
| 4 | 5 | 95278698 | rs74836108 | G | A | ELL2 | . | 1.81 | 2.28 | 264 | 232 | 1 | 2 | 2 | 0.0069 |
| 4 | 6 | 106960382 | rs201789082 | G | C | AIM1 | D | 3.62 | 2.28 | 396 | 348 | 1 | 2 | 2 | 0.005 |
| 4 | 6 | 106968092 | rs371163103 | TC | T | AIM1 | . | 3.62 | 2.28 | 396 | 348 | 1 | 2 | 2 | 0.003 |
| 4 | 6 | 106991468 | rs147230945 | G | A | AIM1 | D | 3.62 | 2.28 | 396 | 348 | 1 | 2 | 2 | 0.001 |
| 4 | 6 | 110636694 | rs141656597 | T | C | METTL24 | . | 1.81 | 2.28 | 132 | 116 | 1 | 2 | 2 | 0.0099 |
| 4 | 6 | 127899925 | rs141247870 | C | T | C6orf58 | . | 5.43 | 3.41 | 132 | 116 | 1 | 3 | 3 | 0.0079 |
| 4 | 6 | 147014059 | rs192310446 | T | C | ADGB | . | 1.81 | . | 132 | 116 | 0 | 3 | 3 | 0.006 |
| 4 | 6 | 149959701 | rs375809770 | AAAG | A | KATNA1 | . | 5.43 | . | 132 | 116 | 0 | 3 | 3 | 0.005 |
| 4 | 6 | 158454680 | rs147847428 | G | A | SYNJ2 | D | 2.41 | 4.55 | 264 | 232 | 1 | 4 | 4 | 0.0079 |
| 4 | 6 | 158516905 | rs202164985 | C | G | SYNJ2 | D | 2.41 | 4.55 | 264 | 232 | 1 | 4 | 4 | 0.001 |
| 4 | 6 | 20113198 | rs199830796 | G | A | MBOAT1 | D | 5.43 | . | 264 | 232 | 0 | 3 | 3 | 0.004 |
| 4 | 6 | 20118693 | rs553353326 | G | A | MBOAT1 | D | 5.43 | . | 264 | 232 | 0 | 3 | 3 | 0.001 |
| 4 | 6 | 33134570 | . | G | A | COL11A2 | D | 1.81 | 3.79 | 660 | 580 | 3 | 10 | 10 | 0.006 |
| 4 | 6 | 33138929 | . | G | A | COL11A2 | D | 1.81 | 3.79 | 660 | 580 | 3 | 10 | 10 | 0.0099 |
| 4 | 6 | 33146518 | . | A | C | COL11A2 | . | 1.81 | 3.79 | 660 | 580 | 3 | 10 | 10 | 0.004 |

TABLE 5-continued

Candidate variant list from RA versus control comparison.

| group | chr | pos | id | ref | alt | gene | LR | Gene burden ratio | | Total No. of alleles in gene | | No. alt alleles in genes | | No. of cases with alt alleles | Variant allele frequency |
|---|---|---|---|---|---|---|---|---|---|---|---|---|---|---|---|
| | | | | | | | | KG East Asia | healthy Ctrl | healthy Ctrl | RA | healthy Ctrl | RA | | KG East Asia |
| 4 | 6 | 33147564 | . | C | A | COL11A2 | D | 1.81 | 3.79 | 660 | 580 | 3 | 10 | 10 | 0.001 |
| 4 | 6 | 33154514 | . | C | A | COL11A2 | D | 1.81 | 3.79 | 660 | 580 | 3 | 10 | 10 | 0.0089 |
| 4 | 6 | 35438350 | rs187631484 | C | T | MIR7111 | . | 2.72 | 1.71 | 132 | 116 | 2 | 3 | 3 | 0.0069 |
| 4 | 6 | 35438350 | rs187631484 | C | T | RPL10A | . | 2.72 | 1.71 | 132 | 116 | 2 | 3 | 3 | 0.0069 |
| 4 | 6 | 39883802 | rs34757428 | A | T | MOCS1 | . | 5.73 | 3.6 | 132 | 110 | 1 | 3 | 3 | 0.0069 |
| 4 | 6 | 42933047 | rs187435179 | A | G | PEX6 | D | 3.62 | 2.28 | 132 | 116 | 1 | 2 | 2 | 0.0089 |
| 4 | 6 | 43160731 | rs568565110 | C | G | CUL9 | . | 5.43 | . | 396 | 348 | 0 | 3 | 3 | 0.001 |
| 4 | 6 | 43170522 | rs200509434 | G | T | CUL9 | D | 5.43 | . | 396 | 348 | 0 | 3 | 3 | 0.0069 |
| 4 | 6 | 43172581 | rs80345623 | G | A | CUL9 | D | 5.43 | . | 396 | 348 | 0 | 3 | 3 | 0.0099 |
| 4 | 6 | 49916648 | rs199555550 | G | A | MUT | . | 9.05 | 5.32 | 370 | 348 | 1 | 5 | 5 | 0.0079 |
| 4 | 6 | 49425591 | rs200908035 | T | C | MUT | . | 9.05 | 5.32 | 370 | 348 | 1 | 5 | 5 | 0.0079 |
| 4 | 6 | 49425720 | rs528689712 | T | C | MUT | D | 9.05 | 5.32 | 370 | 348 | 1 | 5 | 5 | 0.001 |
| 4 | 6 | 72678681 | rs532652925 | C | G | RIMS1 | . | 1.81 | 2.28 | 264 | 232 | 1 | 2 | 2 | 0.001 |
| 4 | 6 | 72974764 | rs564292772 | C | A | RIMS1 | . | 1.81 | 2.28 | 264 | 232 | 1 | 2 | 2 | 0.003 |
| 4 | 6 | 76540124 | rs187811833 | C | T | MYO6 | . | 1.81 | . | 130 | 116 | 0 | 3 | 3 | 0.0089 |
| 4 | 6 | 89977391 | rs146618576 | T | C | GABRR2 | . | 7.24 | 3.03 | 396 | 348 | 3 | 8 | 8 | 0.002 |
| 4 | 6 | 89977789 | rs141423190 | A | C | GABRR2 | . | 7.24 | 3.03 | 396 | 348 | 3 | 8 | 8 | 0.0079 |
| 4 | 6 | 89978946 | rs188424932 | G | A | GABRR2 | D | 7.24 | 3.03 | 396 | 348 | 3 | 8 | 8 | 0.003 |
| 4 | 7 | 100357429 | rs374243234 | C | T | ZAN | . | 1.81 | 3.41 | 396 | 348 | 1 | 3 | 3 | 0.001 |
| 4 | 7 | 100363045 | rs184742914 | A | T | ZAN | . | 1.81 | 3.41 | 396 | 348 | 1 | 3 | 3 | 0.003 |
| 4 | 7 | 100389715 | rs369936309 | C | T | ZAN | D | 1.81 | 3.41 | 396 | 348 | 1 | 3 | 3 | 0.003 |
| 4 | 7 | 100656178 | rs74570695 | G | A | MUC12 | . | 2.72 | 3.41 | 132 | 116 | 1 | 3 | 3 | 0.003 |

TABLE 5-continued

Candidate variant list from RA versus control comparison.

| group | chr | pos | id | ref | alt | gene | LR | Gene burden ratio KG East Asia | Gene burden ratio healthy Ctrl | Total No. of alleles in gene healthy Ctrl | Total No. of alleles in gene RA | No. alt alleles in genes healthy Ctrl | No. alt alleles in genes RA | No. of cases with alt alleles | Variant allele frequency KG East Asia |
|---|---|---|---|---|---|---|---|---|---|---|---|---|---|---|---|
| 4 | 7 | 117144344 | rs1800073 | C | T | CFTR | D | 3.62 | 2.26 | 654 | 580 | 2 | 4 | 4 | 0.002 |
| 4 | 7 | 117171053 | rs141723617 | T | C | CFTR | D | 3.62 | 2.26 | 654 | 580 | 2 | 4 | 4 | 0.0079 |
| 4 | 7 | 117199578 | rs138427145 | A | T | CFTR | D | 3.62 | 2.26 | 654 | 580 | 2 | 4 | 4 | 0.001 |
| 4 | 7 | 117235045 | rs397508395 | G | A | CFTR | D | 3.62 | 2.26 | 654 | 580 | 2 | 4 | 4 | 0.001 |
| 4 | 7 | 117307076 | rs4148725 | C | T | CFTR | D | 3.62 | 2.26 | 654 | 580 | 2 | 4 | 4 | 0.006 |
| 4 | 7 | 131888058 | rs143605398 | TGCTAGCCCCCAGCC (SEQ ID NO: 2) | T | PLXNA4 | . | 1.81 | 2.28 | 264 | 232 | 1 | 2 | 2 | 0.0099 |
| 4 | 7 | 131888117 | rs181597184 | C | T | PLXNA4 | D | 1.81 | 2.28 | 264 | 232 | 1 | 2 | 2 | 0.003 |
| 4 | 7 | 139260038 | rs56338252 | T | C | HIPK2 | . | 2.41 | 2.28 | 264 | 232 | 2 | 4 | 3 | 0.003 |
| 4 | 7 | 143017768 | rs201509501 | C | T | CLCN1 | D | 5.43 | 3.41 | 264 | 232 | 1 | 3 | 3 | 0.002 |
| 4 | 7 | 143029550 | rs202119213 | C | T | CLCN1 | D | 5.43 | 3.41 | 264 | 232 | 1 | 3 | 3 | 0.003 |
| 4 | 7 | 26678881 | rs78525926 | G | A | C7orf71 | . | 3.62 | . | 264 | 232 | 0 | 4 | 4 | 0.004 |
| 4 | 7 | 26678910 | rs111516571 | C | T | C7orf71 | . | 3.62 | . | 264 | 232 | 0 | 4 | 4 | 0.004 |
| 4 | 7 | 29535662 | rs3815512 | G | C | CHN2 | . | 3.62 | 2.28 | 264 | 116 | 1 | 2 | 2 | 0.003 |
| 4 | 7 | 47342658 | rs192974657 | G | A | TNS3 | D | 3.62 | 2.28 | 264 | 232 | 1 | 2 | 2 | 0.002 |
| 4 | 7 | 47454718 | rs187456873 | C | T | TNS3 | . | 3.62 | 2.28 | 264 | 232 | 1 | 2 | 2 | 0.002 |
| 4 | 7 | 75192236 | . | C | A | HIP1 | . | 3.62 | 4.55 | 264 | 232 | 1 | 4 | 4 | 0.0089 |
| 4 | 7 | 75210547 | . | A | T | HIP1 | D | 3.62 | 4.55 | 264 | 232 | 1 | 4 | 4 | 0.001 |
| 4 | 8 | 116426998 | rs181035264 | T | A | TRPS1 | . | 5.43 | 1.71 | 264 | 232 | 2 | 3 | 3 | 0.003 |
| 4 | 8 | 116631783 | rs202001185 | T | C | TRPS1 | . | 5.43 | 1.71 | 264 | 232 | 2 | 3 | 3 | 0.004 |
| 4 | 8 | 133900823 | rs368037086 | C | T | TG | . | 1.84 | . | 260 | 228 | 0 | 3 | 3 | 0.002 |

TABLE 5-continued

Candidate variant list from RA versus control comparison.

| group | chr | pos | id | ref | alt | gene | LR | Gene burden ratio KG East Asia | Gene burden ratio healthy Ctrl | Total No. of alleles in gene healthy Ctrl | Total No. of alleles in gene RA | No. alt alleles in genes healthy Ctrl | No. alt alleles in genes RA | No. of cases with alt alleles | Variant allele frequency KG East Asia |
|---|---|---|---|---|---|---|---|---|---|---|---|---|---|---|---|
| 4 | 8 | 133981695 | rs189500765 | C | T | TG | . | 1.84 | . | 260 | 228 | 0 | 3 | 3 | 0.004 |
| 4 | 8 | 144895478 | . | C | A | SCRIB | . | 1.81 | 4.55 | 132 | 116 | 1 | 4 | 4 | 0.006 |
| 4 | 8 | 145694225 | rs193131687 | C | T | KIFC2 | . | 5.43 | . | 132 | 116 | 0 | 3 | 3 | 0.003 |
| 4 | 8 | 145736896 | rs557256260 | C | T | RECQL4 | . | 1.81 | 1.71 | 660 | 580 | 4 | 6 | 6 | 0.001 |
| 4 | 8 | 145738985 | rs536831548 | G | C | RECQL4 | . | 1.81 | 1.71 | 660 | 580 | 4 | 6 | 6 | 0.001 |
| 4 | 8 | 145741388 | rs200097701 | C | G | RECQL4 | . | 1.81 | 1.71 | 660 | 580 | 4 | 6 | 6 | 0.005 |
| 4 | 8 | 145741602 | rs34633809 | C | T | RECQL4 | . | 1.81 | 1.71 | 660 | 580 | 4 | 6 | 6 | 0.0089 |
| 4 | 8 | 145742799 | rs34642881 | T | C | RECQL4 | . | 1.81 | 1.71 | 660 | 580 | 4 | 6 | 6 | 0.0079 |
| 4 | 8 | 17400906 | rs12680645 | G | A | SLC7A2 | D | 2.26 | 2.84 | 396 | 348 | 2 | 5 | 5 | 0.0079 |
| 4 | 8 | 17407821 | rs188973136 | C | G | SLC7A2 | D | 2.26 | 2.84 | 396 | 348 | 2 | 5 | 5 | 0.006 |
| 4 | 8 | 17417839 | rs201373242 | A | G | SLC7A2 | D | 2.26 | 2.84 | 396 | 348 | 2 | 5 | 5 | 0.001 |
| 4 | 8 | 24771326 | rs182011677 | C | G | NEFM | D | 2.72 | . | 264 | 232 | 0 | 3 | 3 | 0.004 |
| 4 | 8 | 24775743 | rs557507354 | C | T | NEFM | D | 2.72 | . | 264 | 232 | 0 | 3 | 3 | 0.001 |
| 4 | 8 | 25293853 | rs2271114 | A | G | KCTD9 | . | 3.68 | 2.25 | 128 | 114 | 1 | 2 | 2 | 0.005 |
| 4 | 8 | 41470357 | rs372694683 | C | T | GPAT4 | . | 3.62 | 2.28 | 132 | 116 | 1 | 2 | 2 | 0.003 |
| 4 | 8 | 43155706 | rs182905752 | C | T | POTEA | . | 3.68 | 2.23 | 254 | 228 | 1 | 2 | 2 | 0.001 |
| 4 | 8 | 43211970 | rs534445172 | A | C | POTEA | . | 3.68 | 2.23 | 254 | 228 | 1 | 2 | 2 | 0.001 |
| 4 | 8 | 89086826 | rs200104505 | T | A | MMP16 | . | 3.62 | 2.28 | 132 | 116 | 1 | 2 | 2 | 0.0099 |
| 4 | 8 | 136917570 | rs200913664 | G | A | BRD3 | . | 3.62 | 2.28 | 132 | 116 | 1 | 2 | 2 | 0.0069 |
| 4 | 9 | 138235867 | rs531171616 | G | A | C9orf62 | . | 3.62 | 2.28 | 264 | 232 | 1 | 2 | 2 | 0.001 |
| 4 | 9 | 138236230 | rs560393458 | T | G | C9orf62 | . | 3.62 | 2.28 | 264 | 232 | 1 | 2 | 2 | 0.004 |
| 4 | 9 | 139008659 | rs373479265 | C | T | C9orf69 | . | 3.62 | 2.28 | 132 | 116 | 1 | 2 | 2 | 0.003 |

TABLE 5-continued

Candidate variant list from RA versus control comparison.

| group | chr | pos | id | ref | alt | gene | LR | Gene burden ratio KG East Asia | Gene burden ratio healthy Ctrl | Total No. of alleles in gene healthy Ctrl | Total No. of alleles in gene RA | No. alt alleles in genes healthy Ctrl | No. alt alleles in genes RA | No. of cases with alt alleles | Variant allele frequency KG East Asia |
|---|---|---|---|---|---|---|---|---|---|---|---|---|---|---|---|
| 4 | 9 | 139360706 | rs189523223 | C | T | SEC16A | . | 7.24 | . | 264 | 232 | 0 | 4 | 4 | 0.004 |
| 4 | 9 | 139372145 | rs192612248 | G | T | SEC16A | . | 7.24 | . | 264 | 232 | 0 | 4 | 4 | 0.005 |
| 4 | 9 | 15571614 | rs182199324 | T | C | CCDC171 | . | 3.62 | 2.28 | 396 | 348 | 1 | 2 | 2 | 0.002 |
| 4 | 9 | 15745503 | rs530529615 | A | T | CCDC171 | . | 3.62 | 2.28 | 396 | 348 | 1 | 2 | 2 | 0.003 |
| 4 | 9 | 15777828 | rs202139088 | T | G | CCDC171 | . | 3.62 | 2.28 | 396 | 348 | 1 | 2 | 2 | 0.002 |
| 4 | 9 | 439392 | rs117109271 | A | G | DOCK8 | . | 1.81 | 1.52 | 264 | 232 | 3 | 4 | 4 | 0.0099 |
| 4 | 9 | 441423 | rs188141951 | C | T | DOCK8 | . | 1.81 | 1.52 | 264 | 232 | 3 | 4 | 4 | 0.003 |
| 4 | 9 | 5968714 | rs183413824 | C | T | KIAA2026 | D | 3.62 | 2.28 | 132 | 116 | 1 | 2 | 2 | 0.005 |
| 4 | 9 | 72517162 | rs12344550 | T | C | C9orf135 | . | 3.62 | . | 264 | 232 | 0 | 4 | 4 | 0.005 |
| 4 | 9 | 72517293 | rs11140833 | G | T | C9orf135 | . | 3.62 | . | 264 | 232 | 0 | 4 | 4 | 0.005 |
| 4 | X | 8759354 | rs768509456 | A | T | FAM9A | . | 3.69 | 4.56 | 262 | 230 | 1 | 4 | 4 | 0.0013 |
| 4 | X | 8763309 | rs774169916 | GCTGCTGCTG CTGCGGCTT (SEQ ID NO: 3) | G | FAM9A | . | 3.69 | 4.56 | 262 | 230 | 1 | 4 | 4 | 0.0026 |
| 4 | X | 96136645 | rs778550013 | C | T | DIAPH2 | D | 3.66 | 2.24 | 260 | 232 | 2 | 4 | 3 | 0.0013 |
| 5 | 11 | 17394037 | rs61406813 | CTT | C | NCR3LG1 | . | 5.43 | 3.41 | 132 | 116 | 2 | 6 | 5 | 0.0089 |
| 5 | 1 | 21926063 | rs61014678 | C | T | RAP1GAP | D | 7.24 | 4.55 | 264 | 232 | 2 | 8 | 7 | 0.0069 |
| 5 | 2 | 111342071 | rs528909726 | G | A | CHCHD5 | . | . | . | 124 | 90 | 0 | 2 | 1 | 0.002 |
| 5 | 7 | 139285351 | rs3735196 | C | G | HIPK2 | . | 2.41 | 2.28 | 264 | 232 | 2 | 4 | 3 | 0.0089 |
| 5 | X | 96396659 | rs363755 | C | T | DIAPH2 | . | 3.66 | 2.24 | 260 | 232 | 2 | 4 | 3 | 0.0052 |
| 6 | 10 | 126714641 | rs12571821 | G | C | CTBP2 | . | 1.81 | 1.52 | 132 | 116 | 3 | 4 | 4 | 0.0446 |
| 6 | 10 | 28970433 | rs79472556 | G | C | BAMBI | D | 1.81 | 2.28 | 264 | 232 | 1 | 2 | 2 | 0.0159 |

TABLE 5-continued

Candidate variant list from RA versus control comparison.

| group | chr | pos | id | ref | alt | gene | LR | Gene burden ratio KG East Asia | Gene burden ratio healthy Ctrl | Total No. of alleles in gene healthy Ctrl | Total No. of alleles in gene RA | No. alt alleles in genes healthy Ctrl | No. alt alleles in genes RA | No. of cases with alt alleles | Variant allele frequency KG East Asia |
|---|---|---|---|---|---|---|---|---|---|---|---|---|---|---|---|
| 6 | 10 | 28970914 | rs750723477 | C | T | BAMBI | . | 1.81 | 2.28 | 264 | 232 | 1 | 2 | 2 | . |
| 6 | 10 | 61956386 | rs34796699 | GA | G | ANK3 | . | 2.45 | 1.6 | 240 | 236 | 14 | 22 | 19 | . |
| 6 | 10 | 61956386 | rs772920191 | G | GAAA | ANK3 | . | 2.45 | 1.6 | 240 | 236 | 14 | 22 | 19 | . |
| 6 | 10 | 61956386 | rs772920191 | G | GA | ANK3 | . | 2.45 | 1.6 | 240 | 236 | 14 | 22 | 19 | . |
| 6 | 10 | 62023781 | rs144841334 | G | A | ANK3 | . | 2.45 | 1.6 | 240 | 236 | 14 | 22 | 19 | 0.0268 |
| 6 | 10 | 81901943 | rs7080405 | G | C | PLAC9 | . | 3.62 | 2.28 | 132 | 116 | 1 | 2 | 2 | 0.0188 |
| 6 | 10 | 81926637 | rs777020491 | G | A | ANXA11 | . | 2.72 | 1.71 | 264 | 232 | 2 | 3 | 3 | . |
| 6 | 10 | 81926750 | rs34332933 | G | C | ANXA11 | . | 2.72 | 1.71 | 264 | 232 | 2 | 3 | 3 | 0.0188 |
| 6 | 10 | 94822756 | rs58993699 | C | T | CYP26C1 | . | 2.41 | 1.52 | 132 | 116 | 3 | 4 | 4 | 0.0119 |
| 6 | 10 | 94834060 | rs185421897 | C | T | CYP26A1 | . | 1.96 | 2.11 | 396 | 348 | 7 | 13 | 11 | 0.0139 |
| 6 | 10 | 94835071 | rs80188100 | A | G | CYP26A1 | . | 1.96 | 2.11 | 396 | 348 | 7 | 13 | 11 | 0.0119 |
| 6 | 10 | 94835072 | rs75053982 | G | A | CYP26A1 | . | 1.96 | 2.11 | 396 | 348 | 7 | 13 | 11 | 0.0119 |
| 6 | 1 | 10042683 | rs138626416 | G | A | NMNAT1 | D | 1.81 | . | 132 | 116 | 0 | 3 | 3 | 0.0159 |
| 6 | 11 | 121323228 | . | G | A | SORL1 | D | 7.24 | 2.28 | 792 | 696 | 2 | 4 | 4 | . |
| 6 | 11 | 121430331 | . | T | C | SORL1 | D | 7.24 | 2.28 | 792 | 696 | 2 | 4 | 4 | . |
| 6 | 11 | 121440905 | rs753319585 | G | A | SORL1 | D | 7.24 | 2.28 | 792 | 696 | 2 | 4 | 4 | . |
| 6 | 11 | 121457048 | rs146197030 | T | G | SORL1 | . | 7.24 | 2.28 | 792 | 696 | 2 | 4 | 4 | . |
| 6 | 11 | 121460027 | rs752525626 | G | C | SORL1 | D | 7.24 | 2.28 | 792 | 696 | 2 | 4 | 4 | . |
| 6 | 11 | 121489543 | rs751110498 | A | C | SORL1 | . | 7.24 | 2.28 | 792 | 696 | 2 | 4 | 4 | . |
| 6 | 1 | 116933040 | rs28622933 | C | G | ATP1A1 | . | 2.41 | 2.28 | 132 | 116 | 4 | 8 | 8 | 0.0268 |
| 6 | 11 | 22232870 | rs78987921 | G | A | ANO5 | . | 3.62 | 4.55 | 264 | 232 | 1 | 4 | 4 | 0.0109 |
| 6 | 11 | 22239801 | . | C | T | ANO5 | . | 3.62 | 4.55 | 264 | 232 | 1 | 4 | 4 | . |

TABLE 5-continued

Candidate variant list from RA versus control comparison.

| group | chr | pos | id | ref | alt | gene | LR | Gene burden ratio KG East Asia | Gene burden ratio healthy Ctrl | Total No. of alleles in gene healthy Ctrl | Total No. of alleles in gene RA | No. alt alleles in genes healthy Ctrl | No. alt alleles in genes RA | No. of cases with alt alleles | Variant allele frequency KG East Asia |
|---|---|---|---|---|---|---|---|---|---|---|---|---|---|---|---|
| 6 | 1 | 145414790 | . | G | C | HFE2 | . | 2.72 | . | 132 | 116 | 0 | 3 | 3 | 0.0129 |
| 6 | 11 | 487419 | . | G | A | PTDSS2 | . | 3.62 | 4.55 | 396 | 348 | 1 | 4 | 4 | . |
| 6 | 11 | 489522 | rs375041205 | C | T | PTDSS2 | . | 3.62 | 4.55 | 396 | 348 | 1 | 4 | 4 | . |
| 6 | 11 | 490077 | rs374769797 | G | A | PTDSS2 | . | 3.62 | 4.55 | 396 | 348 | 1 | 4 | 4 | . |
| 6 | 1 | 15834360 | rs2020902 | A | G | CASP9 | . | 1.81 | 1.71 | 132 | 116 | 2 | 3 | 3 | 0.0317 |
| 6 | 1 | 15860803 | rs11583306 | C | T | DNAJC16 | . | 2.17 | 3.41 | 132 | 116 | 2 | 6 | 6 | 0.0466 |
| 6 | 1 | 159410340 | rs12409540 | T | A | OR10J1 | . | 1.51 | 5.69 | 132 | 116 | 1 | 5 | 5 | 0.0278 |
| 6 | 1 | 160011511 | rs3795339 | C | T | KCNJ10 | D | 2.72 | 1.71 | 132 | 116 | 2 | 3 | 3 | 0.0129 |
| 6 | 11 | 613605 | . | G | C | IRF7 | . | 1.58 | 2.65 | 526 | 464 | 3 | 7 | 7 | . |
| 6 | 11 | 615010 | rs122909899 | G | T | IRF7 | . | 1.58 | 2.65 | 526 | 464 | 3 | 7 | 7 | 0.0208 |
| 6 | 11 | 615011 | rs12272434 | A | T | IRF7 | . | 1.58 | 2.65 | 526 | 464 | 3 | 7 | 7 | 0.0208 |
| 6 | 11 | 615087 | rs761513714 | G | T | IRF7 | . | 1.58 | 2.65 | 526 | 464 | 3 | 7 | 7 | . |
| 6 | 1 | 16382911 | rs72474563 | A | G | CLCNKB | . | 5.43 | 1.71 | 132 | 116 | 4 | 6 | 6 | 0.0357 |
| 6 | 11 | 7060977 | rs76274604 | A | T | NLRP14 | . | 1.51 | 2.84 | 396 | 348 | 2 | 5 | 5 | 0.0327 |
| 6 | 11 | 74082748 | rs117508615 | C | T | PGM2L1 | . | 1.81 | 1.71 | 132 | 116 | 4 | 6 | 6 | 0.0387 |
| 6 | 1 | 177247693 | rs138799872 | C | T | BRINP2 | . | 3.62 | 2.28 | 132 | 116 | 2 | 4 | 4 | 0.0119 |
| 6 | 1 | 182821420 | rs573535598 | AAGG | A | DHX9 | D | 1.81 | 2.28 | 132 | 116 | 1 | 2 | 2 | 0.0109 |
| 6 | 12 | 1023218 | rs4987207 | G | T | RAD52 | . | 1.81 | 1.71 | 396 | 348 | 14 | 21 | 21 | 0.0268 |
| 6 | 12 | 1036304 | rs2286030 | C | T | RAD52 | . | 1.81 | 1.71 | 396 | 348 | 14 | 21 | 21 | 0.0347 |
| 6 | 12 | 1038978 | rs35278212 | C | CT | RAD52 | . | 1.81 | 1.71 | 396 | 348 | 14 | 21 | 21 | 0.0635 |
| 6 | 12 | 109719311 | rs146550988 | C | T | FOXN4 | . | 1.81 | 2.28 | 132 | 116 | 1 | 2 | 2 | 0.0109 |
| 6 | 12 | 11001963 | . | AT | A | PRR4 | . | 1.81 | 2.24 | 130 | 116 | 1 | 2 | 2 | 0.0149 |

TABLE 5-continued

Candidate variant list from RA versus control comparison.

| group | chr | pos | id | ref | alt | gene | LR | Gene burden ratio KG East Asia | Gene burden ratio healthy Ctrl | Total No. of alleles in gene healthy Ctrl | Total No. of alleles in gene RA | No. alt alleles in genes healthy Ctrl | No. alt alleles in genes RA | No. of cases with alt alleles | Variant allele frequency KG East Asia |
|---|---|---|---|---|---|---|---|---|---|---|---|---|---|---|---|
| 6 | 12 | 113592306 | rs200344876 | G | GC | CFAP73 | . | 2.26 | 2.84 | 132 | 116 | 2 | 5 | 5 | 0.0169 |
| 6 | 12 | 16377347 | rs117974895 | C | T | SLC15A5 | . | 1.51 | 2.84 | 132 | 116 | 2 | 5 | 5 | 0.0337 |
| 6 | 1 | 227968222 | rs12568707 | C | T | SNAP47 | . | 2.26 | 1.9 | 132 | 116 | 3 | 5 | 5 | 0.0188 |
| 6 | 1 | 22924364 | rs72651347 | G | A | EPHA8 | . | 1.81 | 6.83 | 264 | 232 | 1 | 6 | 6 | 0.0179 |
| 6 | 1 | 22927298 | rs569320402 | C | T | EPHA8 | D | 1.81 | 6.83 | 264 | 232 | 1 | 6 | 6 | . |
| 6 | 12 | 404774 | rs140234136 | G | T | KDM5A | D | 2.53 | 1.69 | 420 | 356 | 7 | 10 | 10 | 0.0129 |
| 6 | 12 | 417081 | rs373321785 | G | A | KDM5A | D | 2.53 | 1.69 | 420 | 356 | 7 | 10 | 10 | . |
| 6 | 12 | 432376 | rs751710770 | CAAAA | C | KDM5A | . | 2.53 | 1.69 | 420 | 356 | 7 | 10 | 10 | . |
| 6 | 12 | 432376 | rs756310068 | CAAA | C | KDM5A | . | 2.53 | 1.69 | 420 | 356 | 7 | 10 | 10 | 0.0119 |
| 6 | 12 | 498088 | rs117819701 | G | A | KDM5A | . | 2.53 | 1.69 | 420 | 356 | 7 | 10 | 10 | 0.0228 |
| 6 | 12 | 51510213 | rs77417603 | T | A | TFCP2 | . | 1.58 | 1.99 | 132 | 116 | 4 | 7 | 6 | 0.0129 |
| 6 | 12 | 63974439 | rs61935050 | C | T | DPY19L2 | . | 2.41 | 2.24 | 130 | 116 | 2 | 4 | 4 | . |
| 6 | 1 | 26566248 | rs775335757 | T | C | CEP85 | . | 1.81 | 2.28 | 264 | 232 | 2 | 4 | 3 | 0.0228 |
| 6 | 1 | 26601570 | rs115577318 | A | G | CEP85 | . | 1.81 | 2.28 | 264 | 232 | 2 | 4 | 3 | 0.0308 |
| 6 | 1 | 27943525 | rs2231876 | G | C | FGR | . | 1.63 | 1.71 | 132 | 116 | 6 | 9 | 9 | 0.0248 |
| 6 | 13 | 26155953 | rs7335339 | G | C | ATP8A2 | . | 2.41 | 4.55 | 132 | 116 | 1 | 4 | 3 | 0.1052 |
| 6 | 1 | 39466786 | rs10888613 | C | G | AKIRIN1 | . | 1.63 | 2.56 | 132 | 116 | 8 | 18 | 18 | . |
| 6 | 14 | 39784010 | rs53944606 | A | ATGTG | CTAGE5 | . | 1.64 | 3 | 128 | 128 | 4 | 12 | 12 | 0.0615 |
| 6 | 14 | 39784010 | rs53944606 | A | ATGTGTG | CTAGE5 | . | 1.64 | 3 | 128 | 128 | 4 | 12 | 12 | . |
| 6 | 14 | 39784010 | rs53944606 | A | ATGTGTGTG | CTAGE5 | . | 1.64 | 3 | 128 | 128 | 4 | 12 | 12 | . |

TABLE 5-continued

Candidate variant list from RA versus control comparison.

| group | chr | pos | id | ref | alt | gene | LR | Gene burden ratio KG East Asia | Gene burden ratio healthy Ctrl | Total No. of alleles in gene healthy Ctrl | Total No. of alleles in gene RA | No. alt alleles in genes healthy Ctrl | No. alt alleles in genes RA | No. of cases with alt alleles | Variant allele frequency KG East Asia |
|---|---|---|---|---|---|---|---|---|---|---|---|---|---|---|---|
| 6 | 14 | 39784010 | rs539446066 | A | ATGTGTGTGTG (SEQ ID NO: 4) | CTAGE5 | . | 1.64 | 3 | 128 | 128 | 4 | 12 | 12 | . |
| 6 | 1 | 47403818 | rs79056865 | A | G | CYP4A11 | . | 2.72 | 1.71 | 132 | 116 | 8 | 12 | 12 | 0.0536 |
| 6 | 15 | 48512900 | rs749613571 | G | A | SLC12A1 | D | 10.86 | 2.28 | 396 | 348 | 1 | 2 | 2 | . |
| 6 | 15 | 48580692 | rs537641866 | G | A | SLC12A1 | D | 10.86 | 2.28 | 396 | 348 | 1 | 2 | 2 | . |
| 6 | 15 | 48594989 | rs755737521 | G | T | SLC12A1 | D | 10.86 | 2.28 | 396 | 348 | 1 | 2 | 2 | . |
| 6 | 1 | 55076238 | rs7535372 | C | A | FAM151A | . | 1.62 | 1.53 | 130 | 116 | 19 | 26 | 22 | 0.1687 |
| 6 | 15 | 55484910 | rs3759863 | G | A | RSL24D1 | . | 1.81 | 1.55 | 132 | 116 | 11 | 15 | 14 | 0.0685 |
| 6 | 15 | 75628507 | . | C | T | COMMD4 | . | 1.81 | 2.28 | 264 | 232 | 1 | 2 | 2 | . |
| 6 | 15 | 75631598 | rs200129803 | C | T | COMMD4 | . | 1.81 | 2.28 | 264 | 232 | 1 | 2 | 2 | 0.0149 |
| 6 | 16 | 1825689 | rs3826055 | C | T | EME2 | . | 4.53 | 5.69 | 264 | 232 | 1 | 5 | 5 | 0.0129 |
| 6 | 16 | 1825789 | rs746707908 | T | C | EME2 | . | 4.53 | 5.69 | 264 | 232 | 1 | 5 | 5 | . |
| 6 | 16 | 2017804 | rs146108433 | T | G | RNF151 | D | 3.62 | 2.28 | 132 | 116 | 4 | 8 | 7 | 0.0387 |
| 6 | 16 | 30455945 | rs146596728 | A | C | SEPHS2 | . | 2.72 | 1.71 | 264 | 232 | 2 | 3 | 3 | 0.0248 |
| 6 | 16 | 30456188 | rs550048089 | G | A | SEPHS2 | . | 2.72 | 1.71 | 264 | 232 | 2 | 3 | 3 | . |
| 6 | 16 | 31004812 | rs12445568 | T | C | STX1B | . | 1.91 | 1.8 | 132 | 116 | 12 | 19 | 17 | 0.1002 |
| 6 | 16 | 67198846 | rs115335849 | C | T | HSF4 | . | 2.41 | 1.52 | 132 | 116 | 3 | 4 | 4 | 0.0278 |
| 6 | 16 | 733320 | . | A | T | JMJD8 | . | 2.72 | 1.71 | 264 | 232 | 2 | 3 | 3 | . |
| 6 | 16 | 733604 | rs79868981 | G | A | JMJD8 | . | 2.72 | 1.71 | 264 | 232 | 2 | 3 | 3 | 0.0129 |
| 6 | 1 | 67442275 | rs11208979 | C | T | MIER1 | . | 1.66 | 1.93 | 132 | 116 | 13 | 22 | 20 | 0.1171 |
| 6 | 17 | 16342833 | rs11871958 | T | C | LRRC75A-AS1 | . | 1.81 | 2.11 | 132 | 116 | 7 | 13 | 13 | 0.0823 |

TABLE 5-continued

Candidate variant list from RA versus control comparison.

| group | chr | pos | id | ref | alt | gene | LR | Gene burden ratio KG East Asia | Gene burden ratio healthy Ctrl | Total No. of alleles in gene healthy Ctrl | Total No. of alleles in gene RA | No. alt alleles in genes healthy Ctrl | No. alt alleles in genes RA | No. of cases with alt alleles | Variant allele frequency KG East Asia |
|---|---|---|---|---|---|---|---|---|---|---|---|---|---|---|---|
| 6 | 17 | 18022218 | rs765495851 | G | A | MYO15A | D | 2.04 | 1.71 | 1056 | 928 | 4 | 6 | 6 | . |
| 6 | 17 | 18023739 | rs766303371 | T | G | MYO15A | D | 2.04 | 1.71 | 1056 | 928 | 4 | 6 | 6 | . |
| 6 | 17 | 18028490 | . | A | G | MYO15A | D | 2.04 | 1.71 | 1056 | 928 | 4 | 6 | 6 | . |
| 6 | 17 | 18043856 | . | A | G | MYO15A | D | 2.04 | 1.71 | 1056 | 928 | 4 | 6 | 6 | . |
| 6 | 17 | 18051423 | . | A | G | MYO15A | . | 2.04 | 1.71 | 1056 | 928 | 4 | 6 | 6 | . |
| 6 | 17 | 18057215 | rs9916193 | C | G | MYO15A | D | 2.04 | 1.71 | 1056 | 928 | 4 | 6 | 6 | 0.0119 |
| 6 | 17 | 18064722 | rs140029076 | C | T | MYO15A | . | 2.04 | 1.71 | 1056 | 928 | 4 | 6 | 6 | . |
| 6 | 17 | 18071031 | rs201763265 | C | T | MYO15A | D | 2.04 | 1.71 | 1056 | 928 | 4 | 6 | 6 | . |
| 6 | 17 | 38511509 | rs188616110 | C | T | RARA | . | 4.53 | 2.84 | 132 | 116 | 2 | 5 | 5 | 0.0149 |
| 6 | 17 | 47486684 | rs2277637 | T | C | PHB | D | 1.65 | 1.71 | 132 | 116 | 14 | 21 | 17 | 0.123 |
| 6 | 17 | 67079441 | rs143326198 | C | G | ABCA6 | D | 1.63 | 2.26 | 656 | 580 | 2 | 4 | 4 | 0.0119 |
| 6 | 17 | 67081193 | rs527461596 | G | C | ABCA6 | D | 1.63 | 2.26 | 656 | 580 | 2 | 4 | 4 | . |
| 6 | 17 | 67109811 | rs777203184 | T | G | ABCA6 | D | 1.63 | 2.26 | 656 | 580 | 2 | 4 | 4 | . |
| 6 | 17 | 67121068 | . | A | G | ABCA6 | D | 1.63 | 2.26 | 656 | 580 | 2 | 4 | 4 | . |
| 6 | 17 | 67124939 | . | A | C | ABCA6 | D | 1.63 | 2.26 | 656 | 580 | 2 | 4 | 4 | . |
| 6 | 1 | 78420930 | rs151051327 | T | C | FUBP1 | . | 1.52 | 1.76 | 396 | 346 | 13 | 20 | 19 | 0.0109 |
| 6 | 1 | 78429408 | rs2274257 | G | C | FUBP1 | . | 1.52 | 1.76 | 396 | 346 | 13 | 20 | 19 | 0.0903 |
| 6 | 1 | 78432563 | . | A | G | FUBP1 | . | 1.52 | 1.76 | 396 | 346 | 13 | 20 | 19 | . |
| 6 | 18 | 50432706 | rs17389547 | A | C | DCC | . | 1.81 | 1.51 | 396 | 348 | 40 | 53 | 43 | 0.0109 |
| 6 | 18 | 50912515 | rs3764494 | G | A | DCC | . | 1.81 | 1.51 | 396 | 348 | 40 | 53 | 43 | 0.0238 |
| 6 | 18 | 50937026 | rs11873515 | A | G | DCC | . | 1.81 | 1.51 | 396 | 348 | 40 | 53 | 43 | 0.2252 |

TABLE 5-continued

Candidate variant list from RA versus control comparison.

| group | chr | pos | id | ref | alt | gene | LR | Gene burden ratio KG East Asia | Gene burden ratio healthy Ctrl | Total No. of alleles in gene healthy Ctrl | Total No. of alleles in gene RA | No. alt alleles in genes healthy Ctrl | No. alt alleles in genes RA | No. of cases with alt alleles | Variant allele frequency KG East Asia |
|---|---|---|---|---|---|---|---|---|---|---|---|---|---|---|---|
| 6 | 19 | 13318672 | . | CCTGCTGCTGCTGCTGCTGCTGCTG (SEQ ID NO: 5) | C | CACNA1A | . | . | 2.06 | 708 | 668 | 36 | 70 | 70 | . |
| 6 | 19 | 13318672 | rs16054 | CCTGCTG | C | CACNA1A | . | 2.45 | 2.06 | 708 | 668 | 36 | 70 | 70 | 0.0714 |
| 6 | 19 | 13318672 | rs370146696 | CCTG | C | CACNA1A | . | 2.45 | 2.06 | 708 | 668 | 36 | 70 | 70 | . |
| 6 | 19 | 13318672 | rs753460234 | C | CCTG | CACNA1A | . | 2.45 | 2.06 | 708 | 668 | 36 | 70 | 70 | . |
| 6 | 19 | 13318672 | rs753460234 | C | CCTGCTG | CACNA1A | . | 2.45 | 2.06 | 708 | 668 | 36 | 70 | 70 | . |
| 6 | 19 | 13318672 | rs765169827 | CCTGCTGCTGCTGCTG (SEQ ID NO: 6) | C | CACNA1A | . | 2.45 | 2.06 | 708 | 668 | 36 | 70 | 70 | . |
| 6 | 19 | 13394158 | . | T | C | CACNA1A | D | 2.45 | 2.06 | 708 | 668 | 36 | 70 | 70 | . |
| 6 | 19 | 13410044 | . | C | G | CACNA1A | D | 2.45 | 2.06 | 708 | 668 | 36 | 70 | 70 | . |
| 6 | 19 | 13616741 | . | G | A | CACNA1A | . | 2.45 | 2.06 | 708 | 668 | 36 | 70 | 70 | . |
| 6 | 19 | 13616977 | rs15999 | G | A | CACNA1A | D | 2.45 | 2.06 | 708 | 668 | 36 | 70 | 70 | 0.0159 |
| 6 | 19 | 1367226 | rs11668809 | G | A | MUM1 | . | 1.81 | 2.28 | 132 | 116 | 1 | 2 | 2 | 0.0149 |
| 6 | 19 | 32083223 | rs11880125 | A | G | THEG5 | . | 3.02 | 2.84 | 264 | 232 | 4 | 10 | 10 | 0.0179 |
| 6 | 19 | 32083250 | rs79323410 | T | C | THEG5 | . | 3.02 | 2.84 | 264 | 232 | 4 | 10 | 10 | 0.0179 |
| 6 | 19 | 36394245 | rs74258162 | T | C | HCST | . | 1.81 | 3.41 | 132 | 116 | 2 | 6 | 6 | 0.0357 |
| 6 | 19 | 38572367 | rs562186095 | GGCCACC | G | SIPA1L3 | . | 4.66 | 2.17 | 392 | 348 | 14 | 27 | 27 | . |
| 6 | 19 | 38572367 | rs569252662 | G | GGCCACC | SIPA1L3 | . | 4.66 | 2.17 | 392 | 348 | 14 | 27 | 27 | 0.0337 |
| 6 | 19 | 38590722 | . | C | T | SIPA1L3 | D | 4.66 | 2.17 | 392 | 348 | 14 | 27 | 27 | . |

TABLE 5-continued

Candidate variant list from RA versus control comparison.

| group | chr | pos | id | ref | alt | gene | LR | Gene burden ratio | | Total No. of alleles in gene | | No. alt alleles in genes | | No. of cases with alt alleles | Variant allele frequency |
|---|---|---|---|---|---|---|---|---|---|---|---|---|---|---|---|
| | | | | | | | | KG East Asia | healthy Ctrl | healthy Ctrl | RA | healthy Ctrl | RA | | KG East Asia |
| 6 | 19 | 39421820 | rs2304116 | T | G | MRPS12 | . | 3.62 | 2.28 | 132 | 116 | 1 | 2 | 2 | 0.0119 |
| 6 | 19 | 39591919 | rs182155157 | C | G | ACP7 | . | 1.92 | 1.93 | 264 | 232 | 10 | 17 | 16 | 0.0387 |
| 6 | 19 | 39592099 | rs186807855 | T | C | ACP7 | . | 1.92 | 1.93 | 264 | 232 | 10 | 17 | 16 | 0.0179 |
| 6 | 19 | 4099225 | rs200371894 | G | A | MAP2K2 | D | 1.81 | 2.28 | 264 | 232 | 1 | 2 | 2 | 0.0119 |
| 6 | 19 | 4099246 | . | G | A | MAP2K2 | D | 1.81 | 2.28 | 264 | 232 | 1 | 2 | 2 | . |
| 6 | 19 | 51582802 | rs199715229 | C | T | KLK14 | D | 2.72 | 1.71 | 264 | 232 | 2 | 3 | 3 | 0.0119 |
| 6 | 19 | 51585822 | rs769468261 | G | A | KLK14 | . | 2.72 | 1.71 | 264 | 232 | 2 | 3 | 3 | . |
| 6 | 19 | 51729577 | rs201473304 | ACCCAACAACTGGTATCTTT (SEQ ID NO: 7) | A | CD33 | . | 2.11 | 1.99 | 132 | 116 | 4 | 7 | 7 | 0.0258 |
| 6 | 19 | 53554075 | rs1650983 | A | G | ERVV-2 | . | 1.81 | 4.55 | 132 | 116 | 1 | 4 | 4 | 0.0188 |
| 6 | 19 | 54872594 | . | G | A | LAIR1 | . | 1.81 | 1.9 | 396 | 348 | 9 | 15 | 15 | 0.0317 |
| 6 | 19 | 54872611 | . | A | T | LAIR1 | . | 1.81 | 1.9 | 396 | 348 | 9 | 15 | 15 | 0.0308 |
| 6 | 19 | 54872698 | . | C | G | LAIR1 | . | 1.81 | 1.9 | 396 | 348 | 9 | 15 | 15 | 0.0308 |
| 6 | 19 | 55739813 | rs10419308 | G | A | TMEM86B | . | 1.53 | 1.79 | 132 | 116 | 7 | 11 | 11 | 0.0704 |
| 6 | 19 | 57956740 | rs148699125 | C | CA | ZNF749 | . | 1.81 | 6.83 | 132 | 116 | 1 | 6 | 6 | 0.0357 |
| 6 | 19 | 58118371 | rs78803667 | G | A | ZNF530 | D | 4.53 | 1.9 | 132 | 116 | 3 | 5 | 5 | 0.0159 |
| 6 | 19 | 6147453 | rs16993408 | G | C | ACSBG2 | . | 12.07 | 1.9 | 396 | 348 | 6 | 10 | 9 | 0.0119 |
| 6 | 19 | 6161219 | rs78713134 | C | T | ACSBG2 | . | 12.07 | 1.9 | 396 | 348 | 6 | 10 | 9 | 0.0238 |
| 6 | 19 | 6183085 | . | A | ATAG | ACSBG2 | . | 12.07 | 1.9 | 396 | 348 | 6 | 10 | 9 | . |
| 6 | 20 | 31040031 | rs2236156 | C | T | NOL4L | . | 5.43 | . | 132 | 116 | 0 | 3 | 3 | 0.0248 |
| 6 | 20 | 31672812 | rs71349705 | C | T | BPIFB4 | . | 2.72 | 1.71 | 264 | 232 | 2 | 3 | 3 | . |

TABLE 5-continued

Candidate variant list from RA versus control comparison.

| group | chr | pos | id | ref | alt | gene | LR | Gene burden ratio KG East Asia | Gene burden ratio healthy Ctrl | Total No. of alleles in gene healthy Ctrl | Total No. of alleles in gene RA | No. alt alleles in genes healthy Ctrl | No. alt alleles in genes RA | No. of cases with alt alleles | Variant allele frequency KG East Asia |
|---|---|---|---|---|---|---|---|---|---|---|---|---|---|---|---|
| 6 | 20 | 31677295 | rs142982767 | C | T | BPIFB4 | . | 2.72 | 1.71 | 264 | 232 | 2 | 3 | 3 | 0.0179 |
| 6 | 20 | 34572606 | rs6142471 | A | G | CNBD2 | D | 1.81 | 4.55 | 132 | 116 | 1 | 4 | 3 | 0.0278 |
| 6 | 20 | 44511257 | rs35972756 | G | A | ZSWIM1 | . | 2.72 | 1.71 | 132 | 116 | 2 | 3 | 3 | 0.0159 |
| 6 | 20 | 44676727 | rs12481488 | T | A | SLC12A5 | . | 1.81 | 2.28 | 132 | 116 | 2 | 4 | 4 | 0.0238 |
| 6 | 21 | 43412786 | rs200509586 | GTCA | G | ZBTB21 | . | 5.43 | 3.41 | 132 | 116 | 2 | 6 | 6 | 0.0109 |
| 6 | 21 | 44293806 | rs146400491 | G | A | WDR4 | . | 3.02 | 5.69 | 132 | 116 | 1 | 5 | 4 | 0.0208 |
| 6 | 21 | 44488667 | . | C | T | CBS | D | 3.62 | 2.28 | 264 | 232 | 2 | 4 | 4 | . |
| 6 | 21 | 44492252 | rs201827340 | G | A | CBS | D | 3.62 | 2.28 | 264 | 232 | 2 | 4 | 4 | 0.0129 |
| 6 | 2 | 16979766 | . | G | A | ABCB11 | D | 3.02 | 2.84 | 396 | 348 | 2 | 5 | 5 | . |
| 6 | 2 | 169801131 | rs118109635 | G | A | ABCB11 | D | 3.02 | 2.84 | 396 | 348 | 2 | 5 | 5 | 0.0129 |
| 6 | 2 | 169953135 | . | A | G | ABCB11 | . | 3.02 | 2.84 | 396 | 348 | 2 | 5 | 5 | . |
| 6 | 2 | 175304621 | rs67227536 | C | G | GPR155 | . | 3.62 | 2.28 | 264 | 232 | 2 | 4 | 4 | 0.0139 |
| 6 | 2 | 175333632 | rs28588913 | G | A | GPR155 | D | 3.62 | 2.28 | 264 | 232 | 2 | 4 | 4 | 0.0248 |
| 6 | 2 | 25603008 | rs13055430 | C | T | CRYBB3 | . | 3.62 | 3.03 | 132 | 116 | 3 | 8 | 8 | 0.0268 |
| 6 | 22 | 31521167 | rs150867939 | C | T | INPP5J | D | 3.62 | 2.28 | 924 | 812 | 3 | 6 | 6 | 0.0129 |
| 6 | 22 | 31521324 | . | C | A | INPP5J | D | 3.62 | 2.28 | 924 | 812 | 3 | 6 | 6 | . |
| 6 | 22 | 31521552 | rs774897780 | G | A | INPP5J | D | 3.62 | 2.28 | 924 | 812 | 3 | 6 | 6 | . |
| 6 | 22 | 31522468 | rs767028605 | G | A | INPP5J | D | 3.62 | 2.28 | 924 | 812 | 3 | 6 | 6 | . |
| 6 | 22 | 31524007 | rs769593351 | A | G | INPP5J | D | 3.62 | 2.28 | 924 | 812 | 3 | 6 | 6 | . |
| 6 | 22 | 31524578 | rs202068549 | C | T | INPP5J | D | 3.62 | 2.28 | 924 | 812 | 3 | 6 | 6 | . |
| 6 | 22 | 31530095 | . | G | C | INPP5J | D | 3.62 | 2.28 | 924 | 812 | 3 | 6 | 6 | . |
| 6 | 2 | 232458085 | rs145183277 | TGAGA | T | C2orf57 | . | 2.09 | 2.84 | 132 | 116 | 6 | 15 | 15 | 0.0536 |

TABLE 5-continued

Candidate variant list from RA versus control comparison.

| group | chr | pos | id | ref | alt | gene | LR | Gene burden ratio KG East Asia | Gene burden ratio healthy Ctrl | Total No. of alleles in gene healthy Ctrl | Total No. of alleles in gene RA | No. alt alleles in genes healthy Ctrl | No. alt alleles in genes RA | No. of cases with alt alleles | Variant allele frequency KG East Asia |
|---|---|---|---|---|---|---|---|---|---|---|---|---|---|---|---|
| 6 | 22 | 32992729 | rs191241866 | G | A | SYN3 | . | 5.43 | . | 132 | 116 | 0 | 3 | 3 | 0.0129 |
| 6 | 2 | 237246998 | . | G | T | IQCA1 | D | 2.72 | 1.71 | 264 | 232 | 2 | 3 | 3 | . |
| 6 | 2 | 237247013 | rs186626813 | G | A | IQCA1 | D | 2.72 | 1.71 | 264 | 232 | 2 | 3 | 3 | 0.0129 |
| 6 | 2 | 239344663 | rs11904390 | T | A | ASB1 | . | 1.97 | 3.41 | 132 | 116 | 4 | 12 | 12 | 0.0595 |
| 6 | 22 | 40801855 | rs188579679 | C | T | SGSM3 | . | 2.72 | . | 132 | 116 | 0 | 6 | 6 | 0.0169 |
| 6 | 22 | 43933284 | rs3833393 | CCT | C | EFCAB6 | . | 1.63 | 2.28 | 264 | 232 | 2 | 4 | 4 | 0.0159 |
| 6 | 22 | 44131813 | . | C | T | EFCAB6 | D | 1.63 | 2.28 | 264 | 232 | 2 | 4 | 4 | . |
| 6 | 22 | 46668317 | rs779119363 | A | G | TTC38 | . | 3.62 | 1.71 | 396 | 348 | 2 | 3 | 3 | . |
| 6 | 22 | 46679924 | rs201314224 | G | C | TTC38 | D | 3.62 | 1.71 | 396 | 348 | 2 | 3 | 3 | 0.0198 |
| 6 | 22 | 46684341 | rs763990471 | G | A | TTC38 | . | 3.62 | 1.71 | 396 | 348 | 2 | 3 | 3 | 0.0208 |
| 6 | 22 | 50754445 | rs80243206 | A | T | DENND6B | . | 1.51 | 2.84 | 264 | 232 | 2 | 5 | 5 | . |
| 6 | 22 | 50756452 | rs73439320 | A | G | DENND6B | . | 1.51 | 2.84 | 264 | 232 | 2 | 5 | 5 | . |
| 6 | 2 | 27729343 | . | C | A | GCKR | . | 5.43 | 2.28 | 264 | 232 | 1 | 2 | 2 | 0.1835 |
| 6 | 2 | 27729453 | . | G | A | GCKR | . | 5.43 | 2.28 | 264 | 232 | 1 | 2 | 2 | 0.0179 |
| 6 | 22 | 28634790 | rs12624279 | G | A | FOSL2 | . | 1.65 | 1.63 | 132 | 116 | 21 | 30 | 25 | . |
| 6 | 2 | 31412347 | rs78099670 | G | A | CAPN14 | . | 5.07 | 1.59 | 660 | 580 | 5 | 7 | 7 | . |
| 6 | 2 | 31414833 | . | G | T | CAPN14 | D | 5.07 | 1.59 | 660 | 580 | 5 | 7 | 7 | 0.0149 |
| 6 | 2 | 31414844 | rs147299374 | C | T | CAPN14 | D | 5.07 | 1.59 | 660 | 580 | 5 | 7 | 7 | 0.0139 |
| 6 | 2 | 31414959 | rs141014145 | A | G | CAPN14 | D | 5.07 | 1.59 | 660 | 580 | 5 | 7 | 7 | . |
| 6 | 2 | 31422395 | rs200657395 | TCTC | T | CAPN14 | . | 5.07 | 1.59 | 660 | 580 | 5 | 7 | 7 | 0.0327 |
| 6 | 2 | 47399601 | rs4953472 | A | G | CALM2 | . | 3.62 | 1.71 | 132 | 116 | 4 | 6 | 6 | 0.0317 |
| 6 | 3 | 107097080 | rs138204694 | CAAATG | C | CCDC54 | . | 1.81 | 7.97 | 132 | 116 | 1 | 7 | 7 | . |

TABLE 5-continued

Candidate variant list from RA versus control comparison.

| group | chr | pos | id | ref | alt | gene | LR | Gene burden ratio | | Total No. of alleles in gene | | No. alt alleles in genes | | No. of cases with alt alleles | Variant allele frequency |
|---|---|---|---|---|---|---|---|---|---|---|---|---|---|---|---|
| | | | | | | | | KG East Asia | healthy Ctrl | healthy Ctrl | RA | healthy Ctrl | RA | | KG East Asia |
| 6 | 3 | 111828384 | rs397949663 | G | GT | C3orf52 | . | 1.56 | 1.54 | 132 | 116 | 28 | 38 | 33 | 0.2569 |
| 6 | 3 | 119242443 | rs58978800 | C | T | TIMMDC1 | . | 1.81 | 4.55 | 132 | 116 | 1 | 4 | 4 | 0.0258 |
| 6 | 3 | 122459290 | rs16338 | G | GAGA | HSPBAP1 | . | 1.93 | 1.52 | 264 | 232 | 24 | 32 | 30 | 0.126 |
| 6 | 3 | 122459732 | rs35887395 | G | A | HSPBAP1 | . | 1.93 | 1.52 | 264 | 232 | 24 | 32 | 30 | 0.126 |
| 6 | 3 | 169546730 | rs149140811 | C | T | LRRIQ4 | . | 2.11 | 1.99 | 132 | 116 | 4 | 7 | 6 | 0.0357 |
| 6 | 3 | 183908937 | rs765039315 | C | T | ABCF3 | D | 5.43 | 1.71 | 396 | 348 | 2 | 3 | 3 | . |
| 6 | 3 | 183910604 | rs118183801 | T | C | ABCF3 | D | 5.43 | 1.71 | 396 | 348 | 2 | 3 | 3 | 0.0169 |
| 6 | 3 | 183911455 | . | . | . | ABCF3 | D | 5.43 | 1.71 | 396 | 348 | 2 | 3 | 3 | . |
| 6 | 3 | 187451313 | rs140944763 | T | A | BCL6 | . | 1.55 | 6.83 | 132 | 116 | 1 | 6 | 6 | 0.0228 |
| 6 | 3 | 32030579 | rs373566244 | GT | G | ZNF860 | . | 2.72 | 1.71 | 132 | 116 | 2 | 3 | 3 | 0.0129 |
| 6 | 3 | 50219709 | rs12639175 | A | G | SEMA3F | . | 1.81 | 2.28 | 132 | 116 | 1 | 2 | 2 | 0.0129 |
| 6 | 3 | 121719584 | rs35363618 | T | TA | PRDM5 | . | 1.77 | 1.99 | 132 | 116 | 24 | 42 | 34 | 0.1885 |
| 6 | 4 | 16181283 | rs78942971 | A | G | TAPT1 | . | 2.9 | 2.25 | 98 | 190 | 3 | 8 | 8 | 0.0248 |
| 6 | 4 | 177109395 | rs200650536 | T | G | SPATA4 | D | 2.72 | 3.39 | 262 | 190 | 1 | 3 | 3 | 0.0149 |
| 6 | 4 | 177116495 | . | C | A | SPATA4 | . | 2.72 | 3.39 | 262 | 232 | 1 | 3 | 3 | . |
| 6 | 4 | 2233893 | rs117602484 | A | G | HAUS3 | . | 3.32 | 1.66 | 210 | 190 | 2 | 3 | 3 | 0.0119 |
| 6 | 4 | 2240347 | rs376063631 | C | T | HAUS3 | D | 3.32 | 1.66 | 210 | 190 | 2 | 3 | 3 | . |
| 6 | 4 | 69094459 | rs75647314 | C | A | TMPRSS11B | . | 2.11 | 1.59 | 264 | 232 | 5 | 7 | 7 | 0.0278 |
| 6 | 4 | 69096987 | rs575638339 | C | T | TMPRSS11B | D | 2.11 | 1.59 | 264 | 232 | 5 | 7 | 7 | . |
| 6 | 4 | 71888240 | rs67437265 | C | T | DCK | D | 1.81 | 1.82 | 132 | 116 | 5 | 8 | 8 | 0.0387 |
| 6 | 4 | 76447062 | rs76333976 | G | C | THAP6 | . | 1.81 | 2.28 | 132 | 116 | 1 | 2 | 2 | 0.0129 |
| 6 | 4 | 76581064 | rs6823013 | C | T | G3BP2 | . | 1.81 | 1.71 | 132 | 116 | 2 | 3 | 3 | 0.0198 |

TABLE 5-continued

Candidate variant list from RA versus control comparison.

| group | chr | pos | id | ref | alt | gene | LR | Gene burden ratio KG East Asia | Gene burden ratio healthy Ctrl | Total No. of alleles in gene healthy Ctrl | Total No. of alleles in gene RA | No. alt alleles in genes healthy Ctrl | No. alt alleles in genes RA | No. of cases with alt alleles | Variant allele frequency KG East Asia |
|---|---|---|---|---|---|---|---|---|---|---|---|---|---|---|---|
| 6 | 5 | 140182074 | rs17844259 | G | A | PCDHA3 | D | 3.62 | 2.28 | 132 | 116 | 2 | 4 | 4 | 0.0179 |
| 6 | 5 | 26886200 | rs41271091 | C | A | CDH9 | . | 1.84 | 1.87 | 128 | 114 | 12 | 20 | 20 | 0.0972 |
| 6 | 5 | 70898466 | . | T | TC | MCCC2 | . | 1.81 | 1.71 | 264 | 232 | 2 | 3 | 3 | 0.0179 |
| 6 | 5 | 70922542 | rs549784997 | C | T | MCCC2 | D | 1.81 | 1.71 | 264 | 232 | 2 | 3 | 3 | . |
| 6 | 6 | 109721228 | rs4946972 | A | C | PPIL6 | . | 1.93 | 1.82 | 132 | 116 | 10 | 16 | 15 | 0.1032 |
| 6 | 6 | 109763947 | rs35444917 | TC | T | SMPD2 | . | 1.81 | 1.82 | 132 | 116 | 10 | 16 | 15 | 0.1032 |
| 6 | 6 | 116783619 | rs117361304 | T | G | FAM26F | . | 2.63 | 3.03 | 132 | 116 | 6 | 16 | 16 | 0.0635 |
| 6 | 6 | 136554647 | rs2274141 | A | T | MTFR2 | . | 2.02 | 2.15 | 112 | 104 | 1 | 2 | 2 | 0.0407 |
| 6 | 6 | 167738715 | rs12526096 | G | A | TTLL2 | . | 3.62 | 3.03 | 132 | 116 | 3 | 8 | 8 | 0.0347 |
| 6 | 6 | 25691362 | rs17492659 | C | T | SCGN | . | 1.81 | 1.99 | 132 | 116 | 4 | 7 | 7 | 0.0417 |
| 6 | 6 | 26507069 | rs188130447 | T | C | BTN1A1 | . | 1.81 | 4.55 | 264 | 232 | 1 | 4 | 4 | 0.0208 |
| 6 | 6 | 26509379 | rs752379950 | C | T | BTN1A1 | . | 1.81 | 4.55 | 264 | 232 | 1 | 4 | 4 | . |
| 6 | 6 | 32361841 | . | T | C | BTNL2 | . | 1.85 | 1.67 | 660 | 580 | 53 | 78 | 74 | 0.0417 |
| 6 | 6 | 32361842 | . | G | A | BTNL2 | . | 1.85 | 1.67 | 660 | 580 | 53 | 78 | 74 | 0.0417 |
| 6 | 6 | 32369554 | . | G | A | BTNL2 | . | 1.85 | 1.67 | 660 | 580 | 53 | 78 | 74 | 0.1171 |
| 6 | 6 | 32369586 | . | GAA | G | BTNL2 | . | 1.85 | 1.67 | 660 | 580 | 53 | 78 | 74 | . |
| 6 | 6 | 32370969 | . | TG | T | BTNL2 | . | 1.85 | 1.67 | 660 | 580 | 53 | 78 | 74 | 0.1984 |
| 6 | 6 | 36929653 | rs144897670 | C | T | PI16 | . | 1.81 | 3.41 | 132 | 116 | 1 | 3 | 3 | 0.0129 |
| 6 | 6 | 39330207 | rs9349115 | C | G | KIF6 | . | 1.81 | . | 132 | 116 | 0 | 7 | 7 | 0.0367 |
| 6 | 6 | 87994504 | rs35259282 | C | T | GJB7 | D | 1.81 | 4.55 | 264 | 232 | 1 | 4 | 4 | 0.0188 |
| 6 | 6 | 87994537 | rs112552839 | G | A | GJB7 | D | 1.81 | 4.55 | 264 | 232 | 1 | 4 | 4 | . |
| 6 | 7 | 123267310 | rs116956332 | C | T | ASB15 | . | 3.62 | 2.28 | 132 | 116 | 1 | 2 | 2 | 0.0208 |

TABLE 5-continued

Candidate variant list from RA versus control comparison.

| group | chr | pos | id | ref | alt | gene | LR | Gene burden ratio KG East Asia | Gene burden ratio healthy Ctrl | Total No. of alleles in gene healthy Ctrl | Total No. of alleles in gene RA | No. alt alleles in genes healthy Ctrl | No. alt alleles in genes RA | No. of cases with alt alleles | Variant allele frequency KG East Asia |
|---|---|---|---|---|---|---|---|---|---|---|---|---|---|---|---|
| 6 | 7 | 12727793 | rs117537847 | G | A | ARL4A | . | 1.61 | 2.03 | 132 | 114 | 4 | 7 | 7 | 0.0466 |
| 6 | 7 | 40277228 | rs76667176 | T | C | SUGCT | . | 1.51 | . | 396 | 348 | 0 | 5 | 5 | 0.0119 |
| 6 | 7 | 40899963 | rs751805172 | C | G | SUGCT | D | 1.51 | . | 396 | 348 | 0 | 5 | 5 | . |
| 6 | 7 | 40899965 | rs767692645 | C | G | SUGCT | D | 1.51 | . | 396 | 348 | 0 | 5 | 5 | . |
| 6 | 7 | 72984917 | . | CGTT | C | TBL2 | . | 1.81 | 2.84 | 132 | 116 | 2 | 5 | 5 | 0.0159 |
| 6 | 7 | 73083744 | . | C | T | VPS37D | . | 5.43 | 1.71 | 132 | 116 | 2 | 3 | 3 | 0.0129 |
| 6 | 7 | 73630406 | . | G | A | LAT2 | . | 1.97 | 2.28 | 132 | 116 | 6 | 12 | 11 | 0.0446 |
| 6 | 7 | 7476098 | rs11984435 | T | C | COL28A1 | . | 2.41 | 2.28 | 396 | 348 | 4 | 8 | 8 | 0.0208 |
| 6 | 7 | 7491996 | rs148703211 | G | C | COL28A1 | D | 2.41 | 2.28 | 396 | 348 | 4 | 8 | 8 | 0.0109 |
| 6 | 7 | 7559695 | . | G | C | COL28A1 | D | 2.41 | 2.28 | 396 | 348 | 4 | 8 | 8 | . |
| 6 | 8 | 10677699 | rs61757720 | A | T | PINX1 | . | 2.74 | 1.72 | 264 | 230 | 2 | 3 | 3 | 0.0139 |
| 6 | 8 | 10692283 | rs746583094 | G | A | PINX1 | D | 2.74 | 1.72 | 264 | 230 | 2 | 3 | 3 | . |
| 6 | 8 | 116599274 | rs745384526 | G | A | TRPS1 | D | 5.43 | 2.28 | 264 | 232 | 1 | 2 | 2 | . |
| 6 | 8 | 116599415 | . | T | C | TRPS1 | D | 5.43 | 2.28 | 264 | 232 | 1 | 2 | 2 | . |
| 6 | 8 | 30697414 | rs149889016 | A | G | TEX15 | . | 3.62 | 2.24 | 130 | 116 | 1 | 2 | 2 | 0.0188 |
| 6 | 9 | 137998709 | rs35408956 | T | A | OLFM1 | . | 2.07 | 2.28 | 132 | 116 | 4 | 8 | 8 | 0.0367 |
| 6 | 9 | 140248783 | rs372878424 | G | A | EXD3 | . | 1.81 | 2.28 | 264 | 232 | 1 | 2 | 2 | . |
| 6 | 9 | 140249147 | rs143654067 | C | T | EXD3 | . | 1.81 | 2.28 | 264 | 232 | 1 | 2 | 2 | 0.0119 |

TABLE 5-continued

Candidate variant list from RA versus control comparison.

| group | chr | pos | id | ref | alt | gene | LR | Gene burden ratio KG East Asia | Gene burden ratio healthy Ctrl | Total No. of alleles in gene healthy Ctrl | Total No. of alleles in gene RA | No. alt alleles in genes healthy Ctrl | No. alt alleles in genes RA | No. of cases with alt alleles | Variant allele frequency KG East Asia |
|---|---|---|---|---|---|---|---|---|---|---|---|---|---|---|---|
| 6 | 9 | 5892552 | rs148372841 | G | C | MLANA | . | 4.53 | 5.69 | 132 | 116 | 1 | 5 | 5 | 0.0139 |
| 6 | X | 2871176 | rs56393981 | G | A | ARSE | . | 2.74 | 3.41 | 132 | 116 | 2 | 6 | 5 | 0.0262 |
| 6 | X | 49114808 | . | C | A | FOXP3 | D | 2.06 | 5.12 | 132 | 116 | 2 | 9 | 8 | 0.0393 |
| 6 | X | 8763309 | . | GCTGCTGCTG CTGCGGCTT (SEQ ID NO: 8) | * | FAM9A | . | 3.69 | . | 130 | 114 | 0 | 4 | 4 | . |

TABLE 6

High priority candidate gene list in Rheumatoid Arthritis disease.

| Gene | SNP | p-Value | Odd ratio | References |
| --- | --- | --- | --- | --- |
| ABHD6 | rs73081554 | 5.00E−08 | 1.18 | Okada Y, PMID: 24390342 |
| ACOXL | rs6732565 | 3.00E−08 | 1.07 | Okada Y, PMID: 24390342 |
| AFF3 | rs9653442\| rs11676922\| rs10865035 | 1.00E−14\| 1.00E−08\| 2.00E−08\| 2.00E−06 | 1.12\|1.12\| 1.12 | Okada Y, PMID: 24390342\|Stahl E A, PMID: 20453842\|Jiang L, PMID: 24782177\|Stahl E A, PMID: 20453842 |
| AHNAK2 | rs2582532 | 3.00E−07 | 1.17 | Okada Y, PMID: 24390342 |
| AIRE | rs2075876\| rs760426 | 4.00E−09\| 4.40E−08 | 1.18\|1.16 | Terao C, PMID: 21505073\|Terao C, PMID: 21505073 |
| ANAPC4 | rs3816587 | 9.00E−06 | 1.09 | WTCCC, PMID: 17554300 |
| ANKRD55 | rs77331626\| rs7731626\| rs6859219 | 7.00E−24\| 8.00E−23\| 1.00E−11 | 1.21\|1.21\| 1.28 | Okada Y, PMID: 24390342\|Okada Y, PMID: 24390342\|Stahl E A, PMID: 20453842 |
| ANXA3 | rs2867461 | 1.00E−12 | 1.13 | Okada Y, PMID: 22446963 |
| APOM | rs805297 | 3.00E−10 | 1.56 | Hu H J, PMID: 21844665 |
| ARAP1 | rs3781913 | 6.00E−10 | 1.12 | Okada Y, PMID: 22446963 |
| ARHGEF3 | rs2062583 | 2.16E−06 | 0.63 | Freudenberg J, PMID: 21452313 |
| ARID5B | rs71508903\| rs71508903\| rs10821944 | 1.00E−08\| 1.00E−08\| 6.00E−18 | 1.18\|1.18\| 1.16 | Okada Y, PMID: 24390342\|Okada Y, PMID: 24390342\|Okada Y, PMID: 22446963 |
| ARL15 | rs255758 | 7.00E−06 | 1.42 | Negi S, PMID: 23918589 |
| ATG5 | rs9372120 | 4.00E−08 | 1.10 | Okada Y, PMID: 24390342 |
| ATM | chr11: 107967350 | 1.00E−08 | 1.21 | Okada Y, PMID: 24390342 |
| B3GNT2 | rs13385025\| rs11900673 | 9.00E−07\| 1.00E−08 | 1.11\|1.11 | Okada Y, PMID: 24390342\|Okada Y, PMID: 22446963 |
| BATF | rs7155603 | 1.00E−07 | 1.16 | Stahl E A, PMID: 20453842 |
| BLK | rs2736337\| rs1600249\| rs2736340 | 2.00E−07\| 5.00E−06\| 1.22E−05\| 6.00E−09 | 1.15\|0.77\| 1.29\|1.19 | Okada Y, PMID: 24390342\|Freudenberg J, PMID: 21452313\|Freudenberg J, PMID: 21452313\|Gregersen P K, PMID: 19503088 |
| BTNL2 | rs3763309 | 2.00E−124 | 2.30 | Orozco G, PMID: 24449572 |
| C1QBP | rs72634030 | 2.00E−09 | 1.12 | Okada Y, PMID: 24390342 |
| C4orf52 | rs11933540 | 1.00E−16 | 1.15 | Okada Y, PMID: 24390342 |
| C5 | rs10985070\| rs3761847\| rs881375 | 4.00E−09\| 2.00E−07\| 4.00E−08 | 1.09\|1.13\| NR | Okada Y, PMID: 24390342\|Stahl E A, PMID: 20453842\|Gregersen P K, PMID: 19503088 |
| C5orf30 | rs2561477\| rs26232 | 1.00E−10\| 4.00E−08 | 1.09\|1.14 | Okada Y, PMID: 24390342\|Stahl E A, PMID: 20453842 |
| C6orf10 | rs9275406 | 3.00E−12 | 2.10 | Negi S, PMID: 23918589 |
| CASP8 | rs6715284 | 2.00E−09 | 1.15 | Okada Y, PMID: 24390342 |
| CCL19 | rs11574914 | 2.00E−15 | 1.13 | Okada Y, PMID: 24390342 |
| CCL21 | rs951005\| rs2812378\| rs11574914 | 4.00E−10\| 3.00E−08\| 2.00E−15 | 1.19\|1.12\| 1.13 | Stahl E A, PMID: 20453842\|Raychaudhuri S, PMID: 18794853\|Okada Y, PMID: 24390342 |
| CCR6 | rs1571878\| rs3093023\| rs1854853\| rs3093024 | 1.00E−22\| 2.00E−11\| 4.00E−09\| 2.00E−10\| 8.00E−19 | 1.28\|1.13\| NR\|NR | Okada Y, PMID: 24390342\|Stahl E A, PMID: 20453842\|Jiang L, PMID: 24782177\|Jiang L, PMID: 24782177\|Kochi Y, PMID: 20453841 |
| CD2 | rs624988 | 8.00E−10 | 1.09 | Okada Y, PMID: 24390342 |
| CD226 | rs2469434 | 1.00E−08 | NR | Okada Y, PMID: 24390342 |
| CD244 | rs11265493\| rs3753389\| rs3766379\| rs1319651\| rs6682654 | 4.10E−07\| 8.00E−08\| 3.00E−08\| 6.40E−07\| 7.00E−08 | 1.28\|1.3\| 1.31\|1.28\| 1.31 | Suzuki A, PMID: 18794858\|Suzuki A, PMID: 18794858\|Suzuki A, PMID: 18794858\|Suzuki A, PMID: 18794858\|Suzuki A, PMID: 18794858 |
| CD247 | rs840016 | 2.00E−06 | 1.11 | Stahl E A, PMID: 20453842 |
| CD28 | rs1980422 | 2.00E−13 | 1.13 | Okada Y, PMID: 24390342 |
| CD40 | rs4239702\| rs4810485 | 1.00E−16\| 3.00E−09\| 8.00E−09 | 1.14\|0.85\| 1.15 | Okada Y, PMID: 24390342\|Stahl E A, PMID: 20453842\|Raychaudhuri S, PMID: 18794853 |
| CD5 | rs508970 | 3.00E−06 | 1.07 | Okada Y, PMID: 24390342 |
| CD83 | chr6: 14103212\| rs12529514 | 3.00E−06\| 2.00E−08 | 1.16\|1.14 | Okada Y, PMID: 24390342\|Okada Y, PMID: 22446963 |
| CDK2 | rs773125 | 1.00E−10 | 1.09 | Okada Y, PMID: 24390342 |
| CDK4 | rs1633360 | 1.00E−07 | 1.07 | Okada Y, PMID: 24390342 |

TABLE 6-continued

High priority candidate gene list in Rheumatoid Arthritis disease.

| Gene | SNP | p-Value | Odd ratio | References |
|---|---|---|---|---|
| CDK5RAP2 | rs12379034 | 1.00E−12 | 1.34 | Jiang L, PMID: 24782177 |
| CDK6 | rs4272\|rs42041 | 1.00E−08\|<br>4.00E−06 | 1.10\|1.11 | Okada Y, PMID:<br>24390342\|Raychaudhuri<br>S, PMID: 18794853 |
| CEP57 | rs4409785 | 1.00E−11 | 1.12 | Okada Y, PMID: 24390342 |
| CFLAR | rs6715284 | 2.00E−09 | 1.15 | Okada Y, PMID: 24390342 |
| CLNK | rs13142500 | 2.00E−06 | 1.10 | Okada Y, PMID: 24390342 |
| CLYBL | rs9557321 | 6.00E−08 | 1.73 | Bossini-Castillo L, PMID:<br>24532677 |
| COG6 | rs9603616 | 2.00E−12 | 1.10 | Okada Y, PMID: 24390342 |
| CSF2 | rs657075\|<br>rs657075 | 6.00E−06\|<br>3.00E−10 | 1.12\|1.12 | Okada Y, PMID:<br>24390342\|Okada Y, PMID:<br>22446963 |
| CSF3 | chr17: 38031857 | 2.00E−12 | 1.09 | Okada Y, PMID: 24390342 |
| CTLA4 | rs3087243\|<br>rs3087243\|<br>rs231775\|<br>rs231735 | 3.00E−25\|<br>1.00E−08\|<br>6.30E−07\|<br>6.00E−09 | 1.14\|1.15\|<br>1.09\|NR | Okada Y, PMID: 24390342\|Stahl<br>E A, PMID: 20453842\|Doroth??e<br>Diogo, PMID: 23261300\|Gregersen<br>P K, PMID: 19503088 |
| CXCR5 | rs10790268 | 1.00E−15 | 1.14 | Okada Y, PMID: 24390342 |
| DNASE1L3 | rs73081554 | 5.00E−08 | 1.18 | Okada Y, PMID: 24390342 |
| DPP4 | rs12617656 | 1.00E−08 | 1.24 | Jiang L, PMID: 24782177 |
| EOMES | rs3806624 | 3.00E−08 | 1.08 | Okada Y, PMID: 24390342 |
| ETS1 | rs73013527\|<br>rs4937362 | 1.00E−06\|<br>8.00E−07 | 1.08\|1.09 | Okada Y, PMID:<br>24390342\|Okada Y, PMID:<br>22446963 |
| ETV7 | rs2234067 | 1.60E−09 | 1.15 | Okada Y, PMID: 24390342 |
| FADS1 | rs968567 | 2.00E−08 | 1.12 | Okada Y, PMID: 24390342 |
| FADS2 | rs968567 | 2.00E−08 | 1.12 | Okada Y, PMID: 24390342 |
| FADS3 | rs968567 | 2.00E−08 | 1.12 | Okada Y, PMID: 24390342 |
| FAM124A | rs3790022 | 1.00E−06 | 1.49 | Bossini-Castillo L, PMID:<br>24532677 |
| FCGR2A | rs72717009\|<br>rs1801274\|<br>rs11810143 | 1.00E−07\|<br>2.40E−07\|<br>1.80E−07 | 1.13\|1.10\|<br>1.14 | Okada Y, PMID:<br>24390342\|Doroth??e<br>Diogo, PMID:<br>23261300\|Doroth??e<br>Diogo, PMID: 23261300 |
| FCRL3 | rs2317230 | 2.00E−07 | 1.07 | Okada Y, PMID: 24390342 |
| FLI1 | rs4937362 | 8.00E−07 | 1.09 | Okada Y, PMID: 22446963 |
| GATA3 | rs3824660 | 2.00E−08 | 1.08 | Okada Y, PMID: 24390342 |
| GATSL3 | rs1043099 | 7.00E−09 | 1.19 | Orozco G, PMID: 24449572 |
| GCH1 | rs3783637 | 2.00E−06 | 1.10 | Okada Y, PMID: 22446963 |
| GMCL1L | rs2961663 | 4.00E−06 | NR | Padyukov L, PMID: 21156761 |
| GPR125 | rs6448119 | 7.00E−06 | NR | Padyukov L, PMID: 21156761 |
| GRHL2 | rs678347 | 2.00E−08 | 1.08 | Okada Y, PMID: 24390342 |
| GRM5 | rs518167 | 2.00E−06 | 2.24 | Bossini-Castillo L, PMID:<br>24532677 |
| HLA | rs12194148\|<br>rs2157337 | 5.00E−58\|<br>9.00E−52 | NR\|NR | Padyukov L, PMID:<br>21156761\|Padyukov L, PMID:<br>21156761 |
| HLA-B | rs2596565 | 9.00E−09 | 1.40 | Bossini-Castillo L, PMID:<br>24532677 |
| HLA-DQA1 | rs9271348\|<br>rs6457617\|<br>rs9275406 | 5.00E−07\|<br>1.00E−09\|<br>3.00E−12 | 1.28\|NR\|<br>2.10 | Bossini-Castillo L, PMID:<br>24532677\|Julia A, PMID:<br>18668548\|Negi S, PMID:<br>23918589 |
| HLA-DQA2 | rs12525220\|<br>rs6457617\|<br>rs9275406 | 2.00E−13\|<br>1.00E−09\|<br>3.00E−12 | 2.87\|NR\|<br>2.10 | Jiang L, PMID: 24782177\|Julia<br>A, PMID: 18668548\|Negi<br>S, PMID: 23918589 |
| HLA-DQB1 | rs12525220\|<br>rs9275406 | 2.00E−13\|<br>3.00E−12 | 2.87\|2.10 | Jiang L, PMID: 24782177\|Negi<br>S, PMID: 23918589 |
| HLA-DRB1 | rs9268839\|<br>rs9268839\|<br>rs6910071\|<br>rs7765379\|<br>rs13192471\|<br>rs660895\|<br>rs6457620\|<br>rs615672\|<br>rs9271348 | 1.00E−250\|<br>1.00E−250\|<br>1.00E−299\|<br>5.00E−23\|<br>2.00E−58\|<br>1.00E−108\|<br>4.00E−186\|<br>8.00E−27\|<br>5.00E−07 | 2.47\|2.47\|<br>2.88\|2.51\|<br>NR\|3.62\|<br>2.55\|NR\|<br>1.28 | Okada Y, PMID:<br>24390342\|Okada Y, PMID:<br>24390342\|Stahl E A, PMID:<br>20453842\|Freudenberg J, PMID<br>21452313\|Kochi Y, PMID:<br>20453841\|Plenge R M, PMID:<br>17804836\|Raychaudhuri<br>S, PMID: 18794853\|WTCCC,<br>PMID: 17554300\|Bossini-<br>Castillo L, PMID: 24532677 |
| IFNGR2 | rs73194058 | 1.00E−06 | 1.08 | Okada Y, PMID: 24390342 |
| IGFBP1 | rs6956740 | 5.00E−07 | NR | Padyukov L, PMID: 21156761 |
| IKZF3 | chr17: 38031857\|<br>rs2872507 | 2.00E−12\|<br>9.00E−07 | 1.09\|1.10 | Okada Y, PMID: 24390342\|Stahl<br>E A, PMID: 20453842 |
| IL2 | rs45475795\|<br>rs13119723 | 4.00E−06\|<br>7.00E−07 | 1.14\|1.12 | Okada Y, PMID: 24390342\|Stahl<br>E A, PMID: 20453842 |

TABLE 6-continued

High priority candidate gene list in Rheumatoid Arthritis disease.

| Gene | SNP | p-Value | Odd ratio | References |
|---|---|---|---|---|
| IL20RB | rs9826828 | 9.00E−10 | 1.44 | Okada Y, PMID: 24390342 |
| IL21 | rs4547579\| rs13119723 | 4.00E−06\| 7.00E−07 | 1.14\|1.12 | Okada Y, PMID: 24390342\|Stahl E A, PMID: 20453842 |
| IL2RA | rs706778\| rs706778\| rs2228150\| rs2104286 | 5.00E−14\| 1.00E−11\| 6.60E−06\| 1.00E−06 | 1.10\|1.14\| 1.25\|1.19 | Okada Y, PMID: 24390342\|Stahl E A, PMID: 20453842\|Doroth??e Diogo, PMID: 23261300\|Orozco G, PMID: 24449572 |
| IL2RB | rs3218251 | 6.00E−06 | 1.08 | Okada Y, PMID: 24390342 |
| IL3 | rs657075 | 6.00E−06 | 1.12 | Okada Y, PMID: 24390342 |
| IL6R | rs2228145 | 4.00E−09 | 1.08 | Okada Y, PMID: 24390342 |
| IL6ST | rs6859219 | 1.00E−11 | 1.28 | Stahl E A, PMID: 20453842 |
| INPP5B | rs28411352 | 3.00E−12 | 1.11 | Okada Y, PMID: 24390342 |
| intergenic | rs12413578 | 5.00E−08 | NR | Okada Y, PMID: 24390342 |
| IRAK1 | rs5987194 | 3.00E−12 | 1.16 | Okada Y, PMID: 24390342 |
| IRF4 | rs9378815 | 1.00E−07 | 1.09 | Okada Y, PMID: 24390342 |
| IRF5 | chr7: 128580042\| rs10488631\| rs3807306 | 1.00E−14\| 4.00E−11\| 3.00E−07 | 1.12\|1.19\| 1.44 | Okada Y, PMID: 24390342\|Stahl E A, PMID: 20453842\|Padyukov L, PMID: 21156761 |
| IRF8 | rs13330176\| rs2280381 | 1.00E−12\| 2.00E−06 | 1.12\|1.12 | Okada Y, PMID: 24390342\|Okada Y, PMID: 22446963 |
| JAZF1 | rs67250450 | 3.00E−09 | 1.11 | Okada Y, PMID: 24390342 |
| KCNIP4 | rs6448119 | 7.00E−06 | NR | Padyukov L, PMID: 21156761 |
| KIF3 | rs17374222 | 2.00E−06 | 1.13 | Stahl E A, PMID: 20453842 |
| KIF5A | rs1678542\| rs1678542 | 1.00E−07\| 9.00E−08 | 1.20\|1.12 | Orozco G, PMID: 24449572\|Raychaudhuri S, PMID: 18794853 |
| LBH | rs10175798 | 1.00E−09 | 1.08 | Okada Y, PMID: 24390342 |
| LOC100506023 | rs2105325 | 3.00E−11 | 1.12 | Okada Y, PMID: 24390342 |
| LOC100506403 | rs8133843 | 2.00E−08 | 1.09 | Okada Y, PMID: 24390342 |
| LOC145837 | rs8026898 | 4.00E−19 | 1.15 | Okada Y, PMID: 24390342 |
| LOC339442 | rs12140275 | 2.00E−09 | 1.11 | Okada Y, PMID: 24390342 |
| MED1 | rs1877030 | 2.00E−08 | 1.09 | Okada Y, PMID: 24390342 |
| MHC | rs7748270\| rs6457617\| rs12525220 | 1.00E−16\| 5.00E−75\| 2.00E−13 | 2.01\|2.36\| 2.87 | Jiang L, PMID: 24782177\|WTCCC, PMID: 17554300\|Jiang L, PMID: 24782177 |
| MICA | rs2596565 | 9.00E−09 | 1.40 | Bossini-Castillo L, PMID: 24532677 |
| MMEL1 | chr1: 2523811\| rs3890745 | 5.00E−09\| 1.00E−07 | 1.10\|1.12 | Okada Y, PMID: 24390342\|Raychaudhuri S, PMID: 18794853 |
| MTF1 | rs28411352 | 3.00E−12 | 1.11 | Okada Y, PMID: 24390342 |
| NFKBIE | rs2233424\| rs2233434 | 1.00E−19\| 6.00E−19\| 1.00E−15 | 1.26\|1.19 | Okada Y, PMID: 24390342\|Okada Y, PMID: 22446963\|Myouzen K, PMID: 23028356 |
| OLIG3 | rs2230926\| rs6920220\| rs10499194 | 2.00E−06\| 1.00E−07\| 1.00E−09 | 1.31\|1.22\| 1.33 | Kochi Y, PMID: 20453841\|Plenge R M, PMID: 17982456\|Plenge R M, PMID: 17982456 |
| P2RY10 | chrX: 78464616 | 4.00E−08 | 1.11 | Okada Y, PMID: 24390342 |
| PADI4 | rs2301888\| rs2240335 | 1.00E−18\| 2.00E−08 | 1.13\|1.50 | Okada Y, PMID: 24390342\|Freudenberg J, PMID: 21452313 |
| PDE2A | rs3781913 | 6.00E−10 | 1.12 | Okada Y, PMID: 22446963 |
| PIP4K2C | rs1678542 | 9.00E−08 | 1.12 | Raychaudhuri S, PMID: 18794853 |
| PLCL2 | rs4452313 | 2.00E−10 | NR | Okada Y, PMID: 24390342 |
| PLD4 | rs2582532\| rs2841277 | 3.00E−07\| 2.00E−14 | 1.17\|1.15 | Okada Y, PMID: 24390342\|Okada Y, PMID: 22446963 |
| POU3F1 | rs12131057 | 4.00E−07 | 1.16 | Stahl E A, PMID: 20453842 |
| PPIL4 | rs9373594 | 3.00E−09 | 1.09 | Okada Y, PMID: 24390342 |
| PRKCB1 | rs7404928 | 4.00E−06 | 1.08 | Okada Y, PMID: 22446963 |
| PRKCH | rs3783782\| rs1957895 | 2.00E−09\| 4.00E−07 | 1.14\|1.09 | Okada Y, PMID: 24390342\|Okada Y, PMID: 22446963 |
| PRKCQ | rs947474\| rs4750316 | 3.00E−10\| 2.00E−06\| 4.00E−06 | 1.12\|1.15\| 1.14 | Okada Y, PMID: 24390342\|Stahl E A, PMID: 20453842\|Raychaudhuri S, PMID: 18794853 |
| PTPN11 | rs10774624 | 7.00E−09 | 1.09 | Okada Y, PMID: 24390342 |
| PTPN2 | rs8083786\| rs2847297 | 2.00E−11\| 2.00E−08 | 1.18\|1.10 | Okada Y, PMID: 24390342\|Okada Y, PMID: 22446963 |

TABLE 6-continued

High priority candidate gene list in Rheumatoid Arthritis disease.

| Gene | SNP | p-Value | Odd ratio | References |
|---|---|---|---|---|
| PTPN22 | rs2476601\| | 9.00E−170\| | 1.80\|1.94\| | Okada Y, PMID: 24390342\|Stahl |
| | rs2476601\| | 9.00E−74\|0\| | 1.82\|1.79\| | E A, PMID: 20453842\|Doroth??e |
| | rs6679677 | 1.00E−08\| | 1.98 | Diogo, PMID: 23261300\|Padyukov |
| | | 6.00E−42\| | | L, PMID: 21156761\|Raychaudhuri |
| | | 6.00E−25 | | S, PMID: 18794853\|WTCCC, |
| | | | | PMID: 17554300 |
| PVT1 | rs1516971 | 1.00E−10 | 1.15 | Okada Y, PMID: 24390342 |
| PXK | rs73081554\| | 5.00E−08\| | 1.18\|1.29 | Okada Y, PMID: 24390342\|Stahl |
| | rs13315591 | 5.00E−08 | | E A, PMID: 20453842 |
| RAD51B | rs1950897 | 5.00E−08 | 1.09 | Okada Y, PMID: 24390342 |
| RAG1 | rs331463 | 1.00E−07 | 1.12 | Okada Y, PMID: 24390342 |
| RAG2 | rs331463 | 1.00E−07 | 1.12 | Okada Y, PMID: 24390342 |
| RASGRP1 | rs8032939 | 2.00E−18 | 1.13 | Okada Y, PMID: 24390342 |
| RBPJ | rs874040\| | 1.00E−16\| | 1.14\|1.19 | Stahl E A, PMID: |
| | rs6448432 | 4.00E−07 | | 20453842\|Orozco G, PMID: |
| | | | | 24449572 |
| RCAN1 | chr21: 35928240 | 3.00E−07 | 1.11 | Okada Y, PMID: 24390342 |
| REL | rs34695944\| | 2.00E−15\| | 1.12\|1.13\| | Okada Y, PMID: 24390342\|Stahl |
| | rs13031237\| | 8.00E−07\| | NR | E A, PMID: 20453842\|Gregersen |
| | rs13017599 | 2.00E−12 | | P K, PMID: 19503088 |
| RNASEH2B | rs3790022 | 1.00E−06 | 1.4925 | Bossini-Castillo L, PMID: |
| | | | | 24532677 |
| RPS12P4 | rs4305317 | 2.00E−06 | 1.45 | Padyukov L, PMID: 21156761 |
| RTKN2 | rs6479800\| | 4.00E−06\| | 1.19\|NR | Okada Y, PMID: |
| | rs3125734 | 5.00E−09 | | 24390342\|Myouzen K, PMID: |
| | | | | 23028356 |
| RUNX1 | rs8133843 | 2.00E−08 | 1.09 | Okada Y, PMID: 24390342 |
| SALL3 | rs2002842 | 6.00E−06 | 1.61 | Julia A, PMID: 18668548 |
| SFTPD | rs726288 | 9.00E−09 | 1.22 | Okada Y, PMID: 24390342 |
| SH2B3 | rs10774624\| | 7.00E−09\| | 1.09\|1.08 | Okada Y, PMID: 24390342\|Stahl |
| | rs3184504 | 6.00E−06 | | E A, PMID: 20453842 |
| SMIM21 | rs1943199 | 2.00E−08 | 1.94 | Bossini-Castillo L, PMID: |
| | | | | 24532677 |
| SPRED2 | rs1858037\| | 1.00E−08\| | 1.19\|1.13 | Okada Y, PMID: 24390342\|Stahl |
| | rs934734 | 5.00E−10\| | | E A, PMID: 20453842\|Jiang |
| | | 2.00E−08 | | L, PMID: 24782177 |
| STAT4 | rs11889341\| | 1.00E−12\| | 1.12\|1.16 | Okada Y, PMID: 24390342\|Stahl |
| | rs7574865 | 3.00E−07\| | | E A, PMID: 20453842\|Kochi |
| | | 2.00E−06 | | Y, PMID: 20453841 |
| SYNGR1 | rs909685 | 1.00E−16 | 1.13 | Okada Y, PMID: 24390342 |
| TAGAP | rs2451258 | 2.00E−10 | 1.10 | Okada Y, PMID: 24390342 |
| TEC | rs2664035 | 1.00E−07 | 1.07 | Okada Y, PMID: 24390342 |
| TNFAIP3 | rs7752903\| | 2.00E−20\| | 1.41\|1.22\| | Okada Y, PMID: 24390342\|Stahl |
| | rs6920220\| | 9.00E−13\| | 1.38\|1.33 | E A, PMID: 20453842\|Plenge |
| | rs2230926\| | 1.00E−07\| | | R M, PMID: 17982456\|Doroth??e |
| | rs10499194 | 6.80E−14\| | | Diogo, PMID: 23261300\|Kochi |
| | | 2.00E−06\| | | Y, PMID: 20453841\|Plenge |
| | | 1.00E−09 | | R M, PMID: 17982456 |
| TNFRSF14 | chr1: 2523811\| | 5.00E−09\| | 1.10\|1.12\| | Okada Y, PMID: 24390342\|Stahl |
| | rs3890745 | 4.00E−06\| | NR\|1.12 | E A, PMID: 20453842\|Orozco |
| | | 1.00E−06\| | | G, PMID: |
| | | 1.00E−07 | | 24449572\|Raychaudhuri |
| | | | | S, PMID: 18794853 |
| TNFRSF9 | rs227163 | 3.00E−09 | 1.11 | Okada Y, PMID: 24390342 |
| TPD52 | rs998731 | 2.00E−08 | 1.08 | Okada Y, PMID: 24390342 |
| TRAF1 | rs10985070\| | 4.00E−09\| | 1.09\|1.13\| | Okada Y, PMID: 24390342\|Stahl |
| | rs3761847\| | 2.00E−07\| | 1.10\|NR\|NR | E A, PMID: 20453842\|Doroth??e |
| | rs2239657\| | 5.40E−08\| | | Diogo, PMID: 23261300\|Gregersen |
| | rs881375\| | 4.00E−08\| | | P K, PMID: 19503088\|Jiang |
| | rs2072438 | 3.00E−09 | | L, PMID: 24782177 |
| TRAF1-C5 | rs3761847 | 4.00E−14 | 1.32 | Plenge R M, PMID: 17804836 |
| TRAF6 | rs331463 | 1.00E−07 | 1.12 | Okada Y, PMID: 24390342 |
| TRHDE | rs12831974 | 6.00E−06 | 1.27 | Freudenberg J, PMID: 21452313 |
| TXNDC11 | rs4780401 | 4.00E−08 | 1.07 | Okada Y, PMID: 24390342 |
| TYK2 | rs34536443 | 5.00E−16 | 1.46 | Okada Y, PMID: 24390342 |
| UBASH3A | rs1893592\| | 7.00E−12\| | 1.11\|1.11 | Okada Y, PMID: 24390342\|Stahl |
| | rs11203203 | 4.00E−07 | | E A, PMID: 20453842 |
| UBE2L3 | rs11089637 | 2.00E−07 | 1.10 | Okada Y, PMID: 24390342 |
| WDFY4 | rs2671692 | 3.00E−09 | 1.07 | Okada Y, PMID: 24390342 |
| YDJC | rs11089637 | 2.00E−07 | 1.10 | Okada Y, PMID: 24390342 |
| ZNF438 | rs793108 | 1.00E−09 | 1.08 | Okada Y, PMID: 24390342 |
| ZNF774 | rs6496667 | 1.00E−06 | 1.09 | Okada Y, PMID: 22446963 |

TABLE 7

Clinical conditions associated with group 2 variants in RA and control comparison.

| chr | pos | id | ref | alt | gene | LR | Clinical conditions reported in ClinVar | Function |
|---|---|---|---|---|---|---|---|---|
| 10 | 101829514 | rs61751507 | C | T | CPN1 | T | Anaphylotoxin inactivator deficiency | Peptide hormone metabolism; Protects the body from potent vasoactive and inflammatory peptides. |
| 11 | 18291302 | rs79681911 | G | A | SAA1 | T | Serum amyloid a variant | Activated TLR4 signaling; Cytokine Signaling in Immune system. |
| 3 | 133476698 | rs41295774 | A | G | TF | T | Atransferrinemia | Vesicle-mediated transport; Iron metabolism in placenta. |
| 5 | 41862758 | rs75134564 | G | A | OXCT1 | D | Succinyl-CoA acetoacetate transferase deficiency | Ketone body metabolism; Regulation of lipid metabolism. |
| 7 | 44104839 | rs77938727 | C | T | PGAM2 | D | Glycogen storage disease type X | Glycosaminoglycan metabolism; Immune response in T lymphocytes. |
| X | 38229135 | rs72554348 | G | C | OTC | . | Ornithine carbamoltransferase deficiency | Carbon metabolism; Viral mRNA Translation. |

TABLE 8

Pathway analysis for candidate genes conferring susceptibility to RA

| Pathway | P value | Genes |
|---|---|---|
| Based on genes identified in comparison of RA patients and controls | | |
| ECM-receptor interaction | $2.1 \times 10^{-3}$ | COL4A4, COL6A5, COL11A1, COL11A2, HSPG2, ITGB5, LAMC1, THBS1 |
| Protein digestion and absorption | $2.3 \times 10^{-3}$ | ATP1A1, ATP1A4, COL4A4, COL6A5, COL11A1, COL11A2, MME, PRCP |
| Focal adhesion | $2.8 \times 10^{-2}$ | RASGRF1, COL4A4, COL6A5, COL11A1, COL11A2, FLNB, ITGB5, LAMC1, MYL5, THBS1 |
| Glycerophospholipid metabolism | $4.8 \times 10^{-2}$ | CHAT, GPAT4, LPIN3, LPCAT1, MBOAT1, PTDSS2 |
| Based on genes only identified in disease duration comparison of RA patients | | |
| Olfactory transduction | $1.2 \times 10^{-2}$ | OR14C36, OR4A15, OR52N4, OR6C74, OR6C75, OR7G3, OR9K2 |

TABLE 9

Candidate variant list from RA disease duration comparison.

| group | chr | pos | id | ref | alt | gene | LR | Gene burden ratio KG East Asia | Gene burden ratio ≤1-Year | Total No. of alleles in gene ≤1-Year | Total No. of alleles in gene ≥3-Year | No. alt alleles in genes ≤1-Year | No. alt alleles in genes ≥3-Year | No. of ≥3-Year cases with alt alleles | Variant allele frequency KG East Asia |
|---|---|---|---|---|---|---|---|---|---|---|---|---|---|---|---|
| 2 | 10 | 101829514 | rs61751507 | C | T | CPN1 | T | 2.28 | 2.26 | 52 | 46 | 1 | 2 | 2 | 0.0248 |
| 2 | 1 | 115220086 | rs121912682 | C | T | AMPD1 | D | 4.57 | . | 52 | 46 | 0 | 3 | 3 | 0.0109 |
| 2 | 11 | 18291302 | rs79681911 | G | A | SAA1 | T | 3.04 | 2.26 | 52 | 46 | 1 | 2 | 2 | 0.0198 |
| 2 | 5 | 149212243 | rs77732671 | G | C | PPARGC1B | T | 1.76 | 1.88 | 52 | 46 | 3 | 5 | 5 | 0.0625 |
| 2 | 7 | 138417791 | rs3807153 | A | G | ATP6V0A4 | T | 1.71 | . | 52 | 46 | 0 | 3 | 3 | 0.0516 |
| 2 | X | 38229135 | rs72554348 | G | C | OTC | . | 4.61 | 4.35 | 50 | 46 | 1 | 4 | 3 | 0.0144 |
| 4 | 10 | 135086331 | rs536126291 | C | T | ADAM8 | . | 9.13 | 2.26 | 104 | 92 | 1 | 2 | 2 | 0.002 |
| 4 | 10 | 135087305 | rs3810960 | G | A | ADAM8 | . | 9.13 | 2.26 | 104 | 92 | 1 | 2 | 2 | 0.003 |
| 4 | 10 | 25144247 | rs199794379 | A | G | PRTFDC1 | D | 9.13 | 2.26 | 104 | 92 | 1 | 2 | 2 | 0.004 |
| 4 | 10 | 25147326 | rs199983667 | C | A | PRTFDC1 | D | 9.13 | 2.26 | 104 | 92 | 1 | 2 | 2 | 0.001 |
| 4 | 10 | 70987060 | rs10823320 | A | G | HKDC1 | D | 18.26 | . | 208 | 184 | 0 | 4 | 4 | 0.001 |
| 4 | 10 | 70992606 | rs575180113 | G | A | HKDC1 | D | 18.26 | . | 208 | 184 | 0 | 4 | 4 | 0.003 |
| 4 | 10 | 71002935 | rs185650169 | C | T | HKDC1 | . | 18.26 | . | 208 | 184 | 0 | 4 | 4 | 0.0069 |
| 4 | 10 | 71021004 | rs143285779 | C | C | HKDC1 | D | 18.26 | . | 208 | 184 | 0 | 4 | 4 | 0.001 |
| 4 | 1 | 100174455 | rs192583899 | T | G | FRRS1 | . | 3.04 | 2.26 | 104 | 92 | 1 | 2 | 2 | 0.003 |
| 4 | 1 | 100177969 | rs187278122 | A | G | FRRS1 | . | 3.04 | 2.26 | 104 | 92 | 1 | 2 | 2 | 0.006 |
| 4 | 11 | 130060344 | rs199819888 | C | T | ST14 | . | 1.52 | 2.26 | 156 | 138 | 1 | 2 | 2 | 0.003 |
| 4 | 11 | 130064039 | rs76687780 | C | G | ST14 | . | 1.52 | 2.26 | 156 | 138 | 1 | 2 | 2 | 0.006 |
| 4 | 1 | 11826069 | rs560354825 | G | C | C1orf167 | D | 6.09 | 1.51 | 156 | 138 | 3 | 4 | 4 | 0.002 |
| 4 | 1 | 11826663 | rs374366683 | G | A | C1orf167 | . | 6.09 | 1.51 | 156 | 138 | 3 | 4 | 4 | 0.004 |
| 4 | 1 | 11844289 | rs76627351 | C | T | C1orf167 | . | 6.09 | 1.51 | 156 | 138 | 3 | 4 | 4 | 0.0079 |

TABLE 9-continued

Candidate variant list from RA disease duration comparison.

| group | chr | pos | id | ref | alt | gene | LR | Gene burden ratio KG East Asia | Gene burden ratio ≤1-Year | Total No. of alleles in gene ≤1-Year | Total No. of alleles in gene ≥3-Year | No. alt alleles in genes ≤1-Year | No. alt alleles in genes ≥3-Year | No. of ≥3-Year cases with alt alleles | Variant allele frequency KG East Asia |
|---|---|---|---|---|---|---|---|---|---|---|---|---|---|---|---|
| 4 | 1 | 146759364 | . | C | T | CHD1L | . | 13.7 | . | 48 | 46 | 0 | 3 | 3 | 0.001 |
| 4 | 11 | 74716666 | rs202090872 | G | C | NEU3 | D | 9.13 | 2.26 | 156 | 138 | 1 | 2 | 2 | 0.003 |
| 4 | 11 | 74716935 | rs200629627 | G | A | NEU3 | D | 9.13 | 2.26 | 156 | 138 | 1 | 2 | 2 | 0.003 |
| 4 | 11 | 74717001 | rs539514716 | C | T | NEU3 | D | 9.13 | 2.26 | 156 | 138 | 1 | 2 | 2 | 0.002 |
| 4 | 1 | 176853472 | rs79630456 | C | T | ASTN1 | . | 4.57 | 2.26 | 52 | 46 | 1 | 2 | 2 | 0.0089 |
| 4 | 1 | 19566783 | rs201918168 | C | T | EMC1 | . | 3.04 | 2.26 | 52 | 46 | 1 | 2 | 2 | 0.0079 |
| 4 | 1 | 197070906 | rs118010078 | C | T | ASPM | D | 6.85 | 3.39 | 104 | 92 | 1 | 3 | 3 | 0.0069 |
| 4 | 1 | 197072871 | rs144969324 | C | T | ASPM | D | 6.85 | 3.39 | 104 | 92 | 1 | 3 | 3 | 0.005 |
| 4 | 12 | 21011481 | rs145334570 | C | A | SLCO1B3 | D | 6.85 | . | 52 | 46 | 0 | 3 | 3 | 0.0099 |
| 4 | 1 | 36056256 | rs114404250 | G | A | TFAP2E | D | 6.85 | . | 52 | 46 | 0 | 3 | 3 | 0.0069 |
| 4 | 14 | 21793077 | rs543867152 | C | T | RPGRIP1 | D | 13.7 | 3.39 | 104 | 92 | 1 | 3 | 3 | 0.001 |
| 4 | 14 | 21793236 | rs7157052 | G | A | RPGRIP1 | . | 13.7 | 3.39 | 104 | 92 | 1 | 3 | 3 | 0.002 |
| 4 | 14 | 94703898 | rs148831396 | G | T | PPP4R4 | . | 9.13 | 2.26 | 52 | 46 | 1 | 2 | 2 | 0.005 |
| 4 | 15 | 39876498 | rs200938835 | T | C | THBS1 | D | 4.57 | 2.26 | 156 | 138 | 1 | 2 | 2 | 0.002 |
| 4 | 15 | 39881204 | rs200366954 | A | G | THBS1 | . | 4.57 | 2.26 | 156 | 138 | 1 | 2 | 2 | 0.001 |
| 4 | 15 | 39886402 | rs185847032 | G | A | THBS1 | . | 4.57 | 2.26 | 156 | 138 | 1 | 2 | 2 | 0.002 |
| 4 | 15 | 48512855 | rs116848967 | G | A | SLC12A1 | D | 9.13 | 2.26 | 104 | 92 | 1 | 2 | 2 | 0.003 |
| 4 | 15 | 48566800 | rs201516084 | T | C | SLC12A1 | D | 9.13 | 2.26 | 104 | 92 | 1 | 2 | 2 | 0.005 |
| 4 | 15 | 79298783 | rs182075492 | G | C | RASGRF1 | . | 3.04 | 2.26 | 52 | 46 | 1 | 2 | 2 | 0.005 |
| 4 | 16 | 27492392 | rs200088316 | C | T | GTF3C1 | . | 9.13 | 2.26 | 104 | 92 | 1 | 2 | 2 | 0.001 |
| 4 | 16 | 27494449 | rs536534746 | G | A | GTF3C1 | . | 9.13 | 2.26 | 104 | 92 | 1 | 2 | 2 | 0.003 |

TABLE 9-continued

Candidate variant list from RA disease duration comparison.

| group | chr | pos | id | ref | alt | gene | LR | Gene burden ratio KG East Asia | Gene burden ratio ≤1-Year | Total No. of alleles in gene ≤1-Year | Total No. of alleles in gene ≥3-Year | No. alt alleles in genes ≤1-Year | No. alt alleles in genes ≥3-Year | No. of ≥3-Year cases with alt alleles | Variant allele frequency KG East Asia |
|---|---|---|---|---|---|---|---|---|---|---|---|---|---|---|---|
| 4 | 16 | 57935248 | rs374813501 | C | G | CNGB1 | . | 6.85 | 3.39 | 208 | 184 | 1 | 3 | 3 | 0.0069 |
| 4 | 16 | 57984441 | rs146170855 | C | T | CNGB1 | D | 6.85 | 3.39 | 208 | 184 | 1 | 3 | 3 | 0.002 |
| 4 | 16 | 57993840 | rs201703193 | C | T | CNGB1 | D | 6.85 | 3.39 | 208 | 184 | 1 | 3 | 3 | 0.001 |
| 4 | 16 | 57996967 | rs570828500 | G | A | CNGB1 | D | 6.85 | 3.39 | 208 | 184 | 1 | 3 | 3 | 0.003 |
| 4 | 1 | 6638781 | rs201116489 | C | T | TAS1R1 | D | 4.57 | 2.26 | 104 | 92 | 1 | 2 | 2 | 0.003 |
| 4 | 1 | 6638995 | rs150612979 | C | T | TAS1R1 | D | 4.57 | 2.26 | 104 | 92 | 1 | 2 | 2 | 0.006 |
| 4 | 16 | 70916556 | rs9932260 | G | A | HYDIN | . | 18.26 | 1.51 | 52 | 46 | 3 | 4 | 2 | 0.002 |
| 4 | 17 | 10398298 | rs140873918 | G | T | MYH1 | D | 3.04 | 2.26 | 416 | 368 | 2 | 4 | 4 | 0.002 |
| 4 | 17 | 10401217 | rs148588034 | C | T | MYH1 | D | 3.04 | 2.26 | 416 | 368 | 2 | 4 | 4 | 0.0069 |
| 4 | 17 | 10402103 | rs3744564 | G | A | MYH1 | D | 3.04 | 2.26 | 416 | 368 | 2 | 4 | 4 | 0.003 |
| 4 | 17 | 10403323 | rs534110923 | G | C | MYH1 | D | 3.04 | 2.26 | 416 | 368 | 2 | 4 | 4 | 0.005 |
| 4 | 17 | 10408380 | rs191339081 | T | A | MYH1 | D | 3.04 | 2.26 | 416 | 368 | 2 | 4 | 4 | 0.005 |
| 4 | 17 | 10412897 | rs534998190 | C | T | MYH1 | D | 3.04 | 2.26 | 416 | 368 | 2 | 4 | 4 | 0.002 |
| 4 | 17 | 10417137 | rs141592934 | C | T | MYH1 | . | 3.04 | 2.26 | 416 | 368 | 2 | 4 | 4 | 0.0069 |
| 4 | 17 | 10419751 | rs535620022 | C | T | MYH1 | . | 3.04 | 2.26 | 416 | 368 | 2 | 4 | 4 | 0.001 |
| 4 | 17 | 10541353 | rs201166774 | G | A | MYH3 | . | 2.28 | 2.26 | 104 | 92 | 1 | 2 | 2 | 0.006 |
| 4 | 17 | 10558169 | rs374786690 | G | C | MYH3 | . | 2.28 | 2.26 | 104 | 92 | 1 | 2 | 2 | 0.002 |
| 4 | 17 | 26856125 | rs188424977 | G | A | FOXN1 | D | 3.04 | 2.26 | 156 | 138 | 1 | 2 | 2 | 0.002 |
| 4 | 17 | 26861343 | rs200401045 | C | T | FOXN1 | . | 3.04 | 2.26 | 156 | 138 | 1 | 2 | 2 | 0.001 |
| 4 | 17 | 26864171 | rs187814037 | C | T | FOXN1 | D | 3.04 | 2.26 | 156 | 138 | 1 | 2 | 2 | 0.005 |
| 4 | 17 | 46878711 | rs184362955 | G | A | TTLL6 | D | 13.7 | . | 52 | 46 | 0 | 3 | 3 | 0.001 |
| 4 | 17 | 48245315 | rs186669379 | C | T | SGCA | D | 1.83 | 2.26 | 156 | 138 | 1 | 2 | 2 | 0.006 |

TABLE 9-continued

Candidate variant list from RA disease duration comparison.

| group | chr | pos | id | ref | alt | gene | LR | Gene burden ratio KG East Asia | Gene burden ratio ≤1-Year | Total No. of alleles in gene ≥3-Year | Total No. of alleles in gene ≤1-Year | No. alt alleles in genes ≤1-Year | No. alt alleles in genes ≥3-Year | No. of ≥3-Year cases with alt alleles | Variant allele frequency KG East Asia |
|---|---|---|---|---|---|---|---|---|---|---|---|---|---|---|---|
| 4 | 17 | 48245924 | rs200945974 | G | A | SGCA | D | 1.83 | 2.26 | 138 | 156 | 1 | 2 | 2 | 0.001 |
| 4 | 17 | 48246530 | rs138254713 | G | A | SGCA | D | 1.83 | 2.26 | 138 | 156 | 1 | 2 | 2 | 0.0079 |
| 4 | 17 | 67079395 | rs117323775 | G | T | ABCA6 | D | 9.13 | 2.26 | 92 | 104 | 1 | 2 | 2 | 0.001 |
| 4 | 17 | 67121109 | rs200376492 | A | G | ABCA6 | D | 9.13 | 2.26 | 92 | 104 | 1 | 2 | 2 | 0.0079 |
| 4 | 17 | 73827216 | rs140184929 | C | T | UNC13D | D | 9.13 | 2.26 | 92 | 104 | 1 | 2 | 2 | 0.006 |
| 4 | 17 | 73839609 | rs527842266 | C | G | UNC13D | . | 9.13 | 2.26 | 92 | 104 | 1 | 2 | 2 | 0.002 |
| 4 | 18 | 72179676 | rs201407255 | C | T | CNDP2 | . | 4.57 | 2.26 | 92 | 104 | 1 | 2 | 2 | 0.003 |
| 4 | 18 | 72185883 | rs201217537 | G | A | CNDP2 | . | 4.57 | 2.26 | 92 | 104 | 1 | 2 | 2 | 0.0069 |
| 4 | 19 | 38934191 | rs192495718 | C | G | RYR1 | . | 1.96 | . | 322 | 364 | 0 | 3 | 3 | 0.004 |
| 4 | 19 | 38948941 | rs573737900 | C | T | RYR1 | D | 1.96 | . | 322 | 364 | 0 | 3 | 3 | 0.001 |
| 4 | 19 | 38964364 | rs551509462 | G | C | RYR1 | . | 1.96 | . | 322 | 364 | 0 | 3 | 3 | 0.004 |
| 4 | 19 | 38981375 | rs78851466 | A | G | RYR1 | . | 1.96 | . | 322 | 364 | 0 | 3 | 3 | 0.0089 |
| 4 | 19 | 39014545 | rs200939091 | G | A | RYR1 | . | 1.96 | . | 322 | 364 | 0 | 3 | 3 | 0.002 |
| 4 | 19 | 39014556 | rs370630840 | C | T | RYR1 | D | 1.96 | 2.26 | 322 | 364 | 0 | 3 | 3 | 0.001 |
| 4 | 19 | 39018329 | rs538497899 | C | T | RYR1 | D | 1.96 | 2.26 | 322 | 364 | 0 | 3 | 3 | 0.001 |
| 4 | 19 | 8140232 | rs145316149 | G | A | FBN3 | D | 3.04 | 2.26 | 184 | 208 | 1 | 2 | 2 | 0.004 |
| 4 | 19 | 8150331 | rs142940013 | G | A | FBN3 | D | 3.04 | 2.26 | 184 | 208 | 1 | 2 | 2 | 0.004 |
| 4 | 19 | 8155130 | rs183278638 | G | A | FBN3 | D | 3.04 | 2.26 | 184 | 208 | 1 | 2 | 2 | 0.002 |
| 4 | 19 | 8188820 | rs145435433 | C | T | FBN3 | D | 3.04 | 2.26 | 184 | 208 | 1 | 2 | 2 | 0.006 |
| 4 | 19 | 8979212 | rs149481309 | C | T | MUC16 | . | 5.71 | 2.83 | 184 | 208 | 2 | 5 | 5 | 0.0089 |
| 4 | 19 | 9002496 | rs553074376 | C | T | MUC16 | . | 5.71 | 2.83 | 184 | 208 | 2 | 5 | 5 | 0.006 |

TABLE 9-continued

Candidate variant list from RA disease duration comparison.

| group | chr | pos | id | ref | alt | gene | LR | Gene burden ratio KG East Asia | Gene burden ratio ≤1-Year | Total No. of alleles in gene ≤1-Year | Total No. of alleles in gene ≥3-Year | No. alt alleles in genes ≤1-Year | No. alt alleles in genes ≥3-Year | No. of ≥3-Year cases with alt alleles | Variant allele frequency KG East Asia |
|---|---|---|---|---|---|---|---|---|---|---|---|---|---|---|---|
| 4 | 19 | 9043416 | rs17417801 | G | A | MUC16 | . | 5.71 | 2.83 | 208 | 184 | 2 | 5 | 5 | 0.0079 |
| 4 | 19 | 9056878 | rs200934751 | GAGA | G | MUC16 | . | 5.71 | 2.83 | 208 | 184 | 2 | 5 | 5 | 0.0069 |
| 4 | 20 | 21142998 | rs191064527 | G | A | KIZ | . | 1.96 | . | 156 | 138 | 0 | 3 | 3 | 0.004 |
| 4 | 20 | 21143067 | rs116937124 | T | C | KIZ | . | 1.96 | . | 156 | 138 | 0 | 3 | 3 | 0.006 |
| 4 | 20 | 39788407 | rs201733074 | T | C | PLCG1 | . | 3.04 | 4.52 | 156 | 138 | 1 | 4 | 4 | 0.0079 |
| 4 | 20 | 39797820 | rs547025579 | GACCAGAACC (SEQ ID NO: 9) | G | PLCG1 | . | 3.04 | 4.52 | 156 | 138 | 1 | 4 | 4 | 0.0069 |
| 4 | 20 | 39798092 | rs183538599 | C | T | PLCG1 | . | 3.04 | 4.52 | 156 | 138 | 1 | 4 | 4 | 0.0079 |
| 4 | 21 | 10908822 | rs546417233 | T | C | TPTE | . | 9.13 | 2.26 | 208 | 184 | 1 | 2 | 2 | 0.002 |
| 4 | 21 | 10908886 | rs532224827 | T | C | TPTE | . | 9.13 | 2.26 | 208 | 184 | 1 | 2 | 2 | 0.002 |
| 4 | 21 | 10920159 | rs557556075 | G | T | TPTE | . | 9.13 | 2.26 | 208 | 184 | 1 | 2 | 2 | 0.002 |
| 4 | 21 | 10970067 | rs547492558 | T | C | TPTE | . | 9.13 | 2.26 | 208 | 184 | 1 | 2 | 2 | 0.003 |
| 4 | 21 | 43621840 | rs564785493 | T | A | ABCG1 | . | 9.13 | 2.26 | 104 | 92 | 1 | 2 | 2 | 0.001 |
| 4 | 21 | 43636306 | rs149713099 | C | T | ABCG1 | . | 9.13 | 2.26 | 104 | 92 | 1 | 2 | 2 | 0.0079 |
| 4 | 2 | 170038100 | rs140572511 | G | A | LRP2 | D | 11.41 | . | 260 | 230 | 0 | 5 | 5 | 0.002 |
| 4 | 2 | 170038761 | rs3213760 | C | T | LRP2 | D | 11.41 | . | 260 | 230 | 0 | 5 | 5 | 0.004 |
| 4 | 2 | 170042008 | rs563916043 | C | T | LRP2 | D | 11.41 | . | 260 | 230 | 0 | 5 | 5 | 0.001 |
| 4 | 2 | 170058290 | rs138382534 | C | T | LRP2 | D | 11.41 | . | 260 | 230 | 0 | 5 | 5 | 0.003 |
| 4 | 2 | 170163815 | rs142594441 | C | T | LRP2 | D | 11.41 | . | 260 | 230 | 0 | 5 | 5 | 0.001 |
| 4 | 2 | 179404792 | rs556524594 | C | T | TTN | . | 4.57 | 1.7 | 416 | 368 | 2 | 3 | 3 | 0.001 |
| 4 | 2 | 179425208 | rs142478636 | G | T | TTN | . | 4.57 | 1.7 | 416 | 368 | 2 | 3 | 3 | 0.004 |
| 4 | 2 | 179430305 | rs185887755 | G | A | TTN | . | 4.57 | 1.7 | 416 | 368 | 2 | 3 | 3 | 0.003 |

TABLE 9-continued

Candidate variant list from RA disease duration comparison.

| group | chr | pos | id | ref | alt | gene | LR | Gene burden ratio KG East Asia | Gene burden ratio ≤1-Year | Total No. of alleles in gene ≤1-Year | Total No. of alleles in gene ≥3-Year | No. alt alleles in genes ≤1-Year | No. alt alleles in genes ≥3-Year | No. of ≥3-Year cases with alt alleles | Variant allele frequency KG East Asia |
|---|---|---|---|---|---|---|---|---|---|---|---|---|---|---|---|
| 4 | 2 | 179437342 | rs567446185 | C | T | TTN | D | 4.57 | 1.7 | 416 | 368 | 2 | 3 | 3 | 0.001 |
| 4 | 2 | 179481839 | rs144688960 | C | A | TTN | . | 4.57 | 1.7 | 416 | 368 | 2 | 3 | 3 | 0.001 |
| 4 | 2 | 179504772 | rs551963261 | C | T | TTN | . | 4.57 | 1.7 | 416 | 368 | 2 | 3 | 3 | 0.001 |
| 4 | 2 | 179577222 | rs186857044 | C | A | TTN | D | 4.57 | 1.7 | 416 | 368 | 2 | 3 | 3 | 0.001 |
| 4 | 2 | 179585717 | rs367826445 | C | T | TTN | D | 4.57 | 1.7 | 416 | 368 | 2 | 3 | 3 | 0.002 |
| 4 | 2 | 203058233 | rs13024221 | T | C | KIAA2012 | . | 9.13 | 2.26 | 104 | 92 | 1 | 2 | 2 | 0.003 |
| 4 | 2 | 203059076 | rs141298049 | G | A | KIAA2012 | . | 9.13 | 2.26 | 104 | 92 | 1 | 2 | 2 | 0.006 |
| 4 | 2 | 31522450 | rs150976596 | G | A | INPP5J | D | 4.57 | 3.39 | 104 | 92 | 1 | 3 | 3 | 0.0099 |
| 4 | 2 | 31522715 | rs370874308 | A | T | INPP5J | . | 4.57 | 3.39 | 104 | 92 | 1 | 3 | 3 | 0.003 |
| 4 | 2 | 32614713 | rs78144589 | C | C | SLC5A4 | . | 6.85 | 3.39 | 104 | 92 | 1 | 3 | 3 | 0.0099 |
| 4 | 2 | 32631002 | rs554791323 | T | T | SLC5A4 | D | 6.85 | 3.39 | 104 | 92 | 1 | 3 | 3 | 0.001 |
| 4 | 2 | 70031769 | rs193084283 | A | G | ANXA4 | . | 1.83 | 2.26 | 104 | 92 | 1 | 2 | 2 | 0.0079 |
| 4 | 2 | 70039849 | rs184226986 | G | A | ANXA4 | . | 1.83 | 2.26 | 104 | 92 | 1 | 2 | 2 | 0.0079 |
| 4 | 2 | 71801442 | rs147483765 | C | T | DYSF | D | 3.04 | 2.26 | 156 | 138 | 1 | 2 | 2 | 0.002 |
| 4 | 2 | 71901318 | rs573892877 | C | G | DYSF | . | 3.04 | 2.26 | 156 | 138 | 1 | 2 | 2 | 0.001 |
| 4 | 2 | 71901432 | rs144355449 | C | T | DYSF | . | 3.04 | 2.26 | 156 | 138 | 1 | 2 | 2 | 0.003 |
| 4 | 3 | 130282510 | rs150427289 | T | C | COL6A6 | . | 2.28 | 1.51 | 208 | 184 | 3 | 4 | 4 | 0.0089 |
| 4 | 3 | 130286067 | rs145020873 | A | G | COL6A6 | D | 2.28 | 1.51 | 208 | 184 | 3 | 4 | 4 | 0.0099 |
| 4 | 3 | 130289976 | rs200963433 | C | T | COL6A6 | D | 2.28 | 1.51 | 208 | 184 | 3 | 4 | 4 | 0.004 |
| 4 | 3 | 130346196 | rs117951912 | G | A | COL6A6 | D | 2.28 | 1.51 | 208 | 184 | 3 | 4 | 4 | 0.0069 |
| 4 | 3 | 148904379 | rs555339346 | C | G | CP | D | 9.13 | 2.26 | 156 | 138 | 1 | 2 | 2 | 0.001 |
| 4 | 3 | 148917507 | rs17847018 | T | C | CP | D | 9.13 | 2.26 | 156 | 138 | 1 | 2 | 2 | 0.003 |

TABLE 9-continued

Candidate variant list from RA disease duration comparison.

| group | chr | pos | id | ref | alt | gene | LR | Gene burden ratio KG East Asia | ≤1-Year | Total No. of alleles in gene ≤1-Year | ≥3-Year | No. alt alleles in genes ≤1-Year | ≥3-Year | No. of ≥3-Year cases with alt alleles | Variant allele frequency KG East Asia |
|---|---|---|---|---|---|---|---|---|---|---|---|---|---|---|---|
| 4 | 3 | 148930242 | rs563241895 | A | T | CP | D | 9.13 | 2.26 | 156 | 138 | 1 | 2 | 2 | 0.002 |
| 4 | 3 | 183822730 | rs560673114 | C | CATTCCTCT | HTR3E | . | 2.28 | 2.26 | 156 | 138 | 1 | 2 | 2 | 0.0089 |
| 4 | 3 | 183823729 | rs187832026 | G | T | HTR3E | D | 2.28 | 2.26 | 156 | 138 | 1 | 2 | 2 | 0.0069 |
| 4 | 3 | 183823919 | rs532417196 | T | C | HTR3E | D | 2.28 | 2.26 | 156 | 138 | 1 | 2 | 2 | 0.001 |
| 4 | 3 | 2928719 | rs184171731 | A | C | CNTN4 | . | 2.28 | 1.7 | 156 | 138 | 2 | 3 | 3 | 0.003 |
| 4 | 3 | 3080611 | rs10510251 | G | C | CNTN4 | . | 2.28 | 1.7 | 156 | 138 | 2 | 3 | 3 | 0.003 |
| 4 | 3 | 3081959 | rs339284 | T | C | CNTN4 | . | 6.85 | 1.7 | 156 | 138 | 2 | 3 | 3 | 0.002 |
| 4 | 3 | 62309627 | rs1881268 | G | C | C3orf14 | . | 6.85 | . | 104 | 92 | 0 | 3 | 3 | 0.001 |
| 4 | 3 | 62317022 | rs186089632 | C | A | C3orf14 | . | 6.85 | . | 104 | 92 | 0 | 3 | 3 | 0.003 |
| 4 | 4 | 106158550 | rs141975400 | G | T | TET2 | . | 4.57 | 2.26 | 52 | 46 | 1 | 2 | 2 | 0.005 |
| 4 | 4 | 6596385 | rs3216941 | AC | A | MAN2B2 | . | 9.13 | 2.26 | 52 | 46 | 1 | 2 | 2 | 0.006 |
| 4 | 4 | 983115 | rs143381873 | G | A | SLC26A1 | D | 4.57 | 2.26 | 208 | 184 | 1 | 2 | 2 | 0.005 |
| 4 | 4 | 983342 | rs201608921 | C | T | SLC26A1 | D | 4.57 | 2.26 | 208 | 184 | 1 | 2 | 2 | 0.002 |
| 4 | 4 | 983810 | rs563866785 | G | A | SLC26A1 | D | 4.57 | 2.26 | 208 | 184 | 1 | 2 | 2 | 0.001 |
| 4 | 4 | 984938 | rs139024319 | G | A | SLC26A1 | D | 4.57 | 2.26 | 208 | 184 | 1 | 2 | 2 | 0.002 |
| 4 | 5 | 1495038 | rs201521332 | G | A | LPCAT1 | . | 9.55 | 2.36 | 52 | 44 | 1 | 2 | 2 | 0.0069 |
| 4 | 5 | 180477285 | rs200084524 | C | T | BTNL9 | . | 4.57 | . | 104 | 92 | 0 | 3 | 3 | 0.001 |
| 4 | 5 | 180483533 | rs373494500 | T | C | BTNL9 | . | 4.57 | . | 104 | 92 | 0 | 3 | 3 | 0.0069 |
| 4 | 6 | 169622491 | rs138932100 | G | A | THBS2 | D | 2.28 | 2.26 | 208 | 184 | 1 | 2 | 2 | 0.006 |
| 4 | 6 | 169623562 | rs181173220 | G | A | THBS2 | D | 2.28 | 2.26 | 208 | 184 | 1 | 2 | 2 | 0.001 |
| 4 | 6 | 169628312 | rs368102843 | C | T | THBS2 | D | 2.28 | 2.26 | 208 | 184 | 1 | 2 | 2 | 0.001 |

TABLE 9-continued

Candidate variant list from RA disease duration comparison.

| group | chr | pos | id | ref | alt | gene | LR | Gene burden ratio KG East Asia | Gene burden ratio ≤1-Year | Total No. of alleles in gene ≤1-Year | Total No. of alleles in gene ≥3-Year | No. alt alleles in genes ≤1-Year | No. alt alleles in genes ≥3-Year | No. of ≥3-Year cases with alt alleles | Variant allele frequency KG East Asia |
|---|---|---|---|---|---|---|---|---|---|---|---|---|---|---|---|
| 4 | 6 | 169646282 | rs76393784 | A | T | THBS2 | . | 2.28 | 2.26 | 208 | 184 | 1 | 2 | 2 | 0.002 |
| 4 | 6 | 35438350 | rs187631484 | C | T | MIR7111 | . | 4.57 | 2.26 | 52 | 46 | 1 | 2 | 2 | 0.0069 |
| 4 | 6 | 35438350 | rs187631484 | C | T | RPL10A | . | 4.57 | 2.26 | 52 | 46 | 1 | 2 | 2 | 0.0069 |
| 4 | 6 | 43160731 | rs568565110 | C | G | CUL9 | . | 9.13 | 2.26 | 156 | 138 | 1 | 2 | 2 | 0.001 |
| 4 | 6 | 43170522 | rs200509434 | G | T | CUL9 | D | 9.13 | 2.26 | 156 | 138 | 1 | 2 | 2 | 0.0069 |
| 4 | 6 | 43172581 | rs80345623 | G | A | CUL9 | D | 9.13 | 2.26 | 156 | 138 | 1 | 2 | 2 | 0.0099 |
| 4 | 6 | 49916648 | rs199555550 | G | A | MUT | . | 13.7 | . | . | 138 | 0 | 3 | 3 | 0.0079 |
| 4 | 6 | 49925591 | rs200908035 | T | C | MUT | D | 13.7 | . | . | 138 | 0 | 3 | 3 | 0.0079 |
| 4 | 6 | 49925720 | rs528689712 | T | C | MUT | D | 13.7 | . | . | 138 | 0 | 3 | 3 | 0.001 |
| 4 | 6 | 100357429 | rs374243234 | C | T | ZAN | . | 3.04 | 2.26 | 156 | 138 | 1 | 2 | 2 | 0.001 |
| 4 | 6 | 100363045 | rs184742914 | A | T | ZAN | D | 3.04 | 2.26 | 156 | 138 | 1 | 2 | 2 | 0.003 |
| 4 | 6 | 100389715 | rs369936309 | C | T | ZAN | . | 3.04 | 2.26 | 156 | 138 | 1 | 2 | 2 | 0.003 |
| 4 | 7 | 128483506 | rs200215903 | G | A | FLNC | D | 2.28 | 3.39 | 208 | 184 | 1 | 3 | 3 | 0.005 |
| 4 | 7 | 128485314 | rs199917473 | G | A | FLNC | . | 2.28 | 3.39 | 208 | 184 | 1 | 3 | 3 | 0.003 |
| 4 | 7 | 128490926 | rs140857707 | C | T | FLNC | D | 2.28 | 3.39 | 208 | 184 | 1 | 3 | 3 | 0.002 |
| 4 | 7 | 128497224 | rs180834558 | G | T | FLNC | D | 2.28 | 3.39 | 208 | 184 | 1 | 3 | 3 | 0.0099 |
| 4 | 7 | 149481919 | rs561989729 | C | G | SSPO | . | 2.79 | 2.71 | 1484 | 1312 | 5 | 12 | 12 | 0.002 |
| 4 | 7 | 149484595 | rs532285725 | A | G | SSPO | . | 2.79 | 2.71 | 1484 | 1312 | 5 | 12 | 12 | 0.004 |
| 4 | 7 | 149484976 | rs372638209 | G | A | SSPO | . | 2.79 | 2.71 | 1484 | 1312 | 5 | 12 | 12 | 0.002 |
| 4 | 7 | 149486719 | rs185269282 | C | G | SSPO | . | 2.79 | 2.71 | 1484 | 1312 | 5 | 12 | 12 | 0.003 |
| 4 | 7 | 149489049 | rs189781142 | G | T | SSPO | . | 2.79 | 2.71 | 1484 | 1312 | 5 | 12 | 12 | 0.002 |
| 4 | 7 | 149490676 | rs4725314 | C | T | SSPO | . | 2.79 | 2.71 | 1484 | 1312 | 5 | 12 | 12 | 0.001 |

TABLE 9-continued

Candidate variant list from RA disease duration comparison.

| group | chr | pos | id | ref | alt | gene | LR | Gene burden ratio KG East Asia | Gene burden ratio ≤1-Year | Total No. of alleles in gene ≤1-Year | Total No. of alleles in gene ≥3-Year | No. alt alleles in genes ≤1-Year | No. alt alleles in genes ≥3-Year | No. of ≥3-Year cases with alt alleles | Variant allele frequency KG East Asia |
|---|---|---|---|---|---|---|---|---|---|---|---|---|---|---|---|
| 4 | 7 | 149491991 | rs550645855 | G | A | SSPO | . | 2.79 | 2.71 | 1484 | 1312 | 5 | 12 | 12 | 0.003 |
| 4 | 7 | 149492720 | rs573097199 | G | A | SSPO | . | 2.79 | 2.71 | 1484 | 1312 | 5 | 12 | 12 | 0.001 |
| 4 | 7 | 149493767 | rs118118675 | G | A | SSPO | . | 2.79 | 2.71 | 1484 | 1312 | 5 | 12 | 12 | 0.004 |
| 4 | 7 | 149494380 | rs376898523 | C | T | SSPO | . | 2.79 | 2.71 | 1484 | 1312 | 5 | 12 | 12 | 0.002 |
| 4 | 7 | 149501078 | rs147663076 | C | A | SSPO | . | 2.79 | 2.71 | 1484 | 1312 | 5 | 12 | 12 | 0.005 |
| 4 | 7 | 149502637 | rs375487670 | C | T | SSPO | . | 2.79 | 2.71 | 1484 | 1312 | 5 | 12 | 12 | 0.0069 |
| 4 | 7 | 149503944 | rs191161538 | C | T | SSPO | . | 2.79 | 2.71 | 1484 | 1312 | 5 | 12 | 12 | 0.004 |
| 4 | 7 | 149506195 | rs73727627 | C | T | SSPO | . | 2.79 | 2.71 | 1484 | 1312 | 5 | 12 | 12 | 0.001 |
| 4 | 7 | 149509035 | rs189816441 | A | G | SSPO | . | 2.79 | 2.71 | 1484 | 1312 | 5 | 12 | 12 | 0.006 |
| 4 | 7 | 149509064 | rs73727632 | T | C | SSPO | . | 2.79 | 2.71 | 1484 | 1312 | 5 | 12 | 12 | 0.004 |
| 4 | 7 | 149509079 | rs73727633 | T | C | SSPO | . | 2.79 | 2.71 | 1484 | 1312 | 5 | 12 | 12 | 0.004 |
| 4 | 7 | 149509381 | rs757724 | C | T | SSPO | . | 2.79 | 2.71 | 1484 | 1312 | 5 | 12 | 12 | 0.004 |
| 4 | 7 | 149509407 | rs146934333 | G | C | SSPO | . | 2.79 | 2.71 | 1484 | 1312 | 5 | 12 | 12 | 0.0089 |
| 4 | 7 | 149509691 | rs73727635 | G | A | SSPO | . | 2.79 | 2.71 | 1484 | 1312 | 5 | 12 | 12 | 0.004 |
| 4 | 7 | 149515870 | rs371607382 | G | A | SSPO | . | 2.79 | 2.71 | 1484 | 1312 | 5 | 12 | 12 | 0.001 |
| 4 | 7 | 149518144 | rs577743302 | A | C | SSPO | . | 2.79 | 2.71 | 1484 | 1312 | 5 | 12 | 12 | 0.001 |
| 4 | 7 | 149519649 | rs58369703 | G | C | SSPO | . | 2.79 | 2.71 | 1484 | 1312 | 5 | 12 | 12 | 0.003 |
| 4 | 7 | 149519705 | rs55857423 | G | A | SSPO | . | 2.79 | 2.71 | 1484 | 1312 | 5 | 12 | 12 | 0.003 |
| 4 | 7 | 149519711 | rs547007891 | G | T | SSPO | . | 2.79 | 2.71 | 1484 | 1312 | 5 | 12 | 12 | 0.005 |
| 4 | 7 | 149521545 | rs143632762 | G | A | SSPO | . | 2.79 | 2.71 | 1484 | 1312 | 5 | 12 | 12 | 0.001 |
| 4 | 17 | 67246623 | rs559974558 | G | A | ABCA5 | D | 2.9 | 1.5 | 652 | 580 | 6 | 8 | 8 | 0.001 |

TABLE 9-continued

Candidate variant list from RA disease duration comparison.

| group | chr | pos | id | ref | alt | gene | LR | KG East Asia | Gene burden ratio ≤1-Year | Total No. of alleles in gene ≤1-Year | ≥3-Year | No. alt alleles in genes ≤1-Year | ≥3-Year | No. of ≥3-Year cases with alt alleles | Variant allele frequency KG East Asia |
|---|---|---|---|---|---|---|---|---|---|---|---|---|---|---|---|
| 4 | 17 | 67247973 | rs201343208 | G | A | ABCA5 | D | 2.9 | 1.5 | 652 | 580 | 6 | 8 | 8 | 0.001 |
| 4 | 17 | 67250466 | rs199641093 | C | T | ABCA5 | D | 2.9 | 1.5 | 652 | 580 | 6 | 8 | 8 | 0.004 |
| 4 | 17 | 67299017 | rs201944918 | A | G | ABCA5 | D | 2.9 | 1.5 | 652 | 580 | 6 | 8 | 8 | 0.0079 |
| 4 | 17 | 67305519 | rs199888749 | G | A | ABCA5 | D | 2.9 | 1.5 | 652 | 580 | 6 | 8 | 8 | 0.0079 |
| 4 | 17 | 73827216 | rs140184929 | C | T | UNC13D | D | 5.43 | . | 264 | 232 | 0 | 3 | 3 | 0.006 |
| 4 | 17 | 73839609 | rs527842266 | C | G | UNC13D | . | 5.43 | . | 264 | 232 | 0 | 3 | 3 | 0.002 |
| 4 | 17 | 7701543 | rs141742705 | G | A | DNAH2 | D | 1.81 | 2.28 | 396 | 348 | 1 | 2 | 2 | 0.001 |
| 4 | 17 | 7705344 | rs8073196 | G | C | DNAH2 | . | 1.81 | 2.28 | 396 | 348 | 1 | 2 | 2 | 0.001 |
| 4 | 17 | 7736250 | rs201527036 | G | A | DNAH2 | D | 1.81 | 2.28 | 396 | 348 | 1 | 2 | 2 | 0.001 |
| 4 | 17 | 79684531 | rs201577202 | C | T | SLC25A10 | . | 3.62 | 1.52 | 264 | 232 | 3 | 4 | 4 | 0.001 |
| 4 | 17 | 79684871 | rs77609145 | A | T | SLC25A10 | D | 3.62 | 1.52 | 264 | 232 | 3 | 4 | 4 | 0.006 |
| 4 | 18 | 2707800 | rs184984483 | C | T | SMCHD1 | . | 5.48 | 3.37 | 258 | 230 | 1 | 3 | 3 | 0.001 |
| 4 | 18 | 2777922 | rs527648000 | C | T | SMCHD1 | . | 5.48 | 3.37 | 258 | 230 | 1 | 3 | 3 | 0.005 |
| 4 | 18 | 28911778 | rs147775289 | T | C | DSG1 | D | 5.43 | 1.71 | 528 | 464 | 2 | 3 | 3 | 0.003 |
| 4 | 18 | 28934293 | rs149191001 | C | T | DSG1 | D | 5.43 | 1.71 | 528 | 464 | 2 | 3 | 3 | 0.001 |
| 4 | 18 | 28934674 | rs181411154 | G | A | DSG1 | D | 5.43 | 1.71 | 528 | 464 | 2 | 3 | 3 | 0.001 |
| 4 | 18 | 28934927 | rs148488583 | C | G | DSG1 | D | 5.43 | 1.71 | 528 | 464 | 2 | 3 | 3 | 0.004 |
| 4 | 18 | 580853 | rs114933134 | G | A | CETN1 | D | 3.62 | . | 132 | 116 | 0 | 4 | 4 | 0.005 |
| 4 | 18 | 61160178 | rs370525785 | T | C | SERPINB5 | . | 3.62 | 2.28 | 264 | 232 | 1 | 2 | 2 | 0.001 |
| 4 | 18 | 61170818 | rs185364126 | G | A | SERPINB5 | D | 3.62 | 2.28 | 264 | 232 | 1 | 2 | 2 | 0.002 |
| 4 | 18 | 61305002 | rs201297323 | T | C | SERPINB4 | D | 1.81 | 3.41 | 264 | 232 | 1 | 3 | 3 | 0.0069 |
| 4 | 18 | 61305289 | rs188021365 | A | T | SERPINB4 | . | 1.81 | 3.41 | 264 | 232 | 1 | 3 | 3 | 0.005 |

TABLE 9-continued

Candidate variant list from RA disease duration comparison.

| group | chr | pos | id | ref | alt | gene | LR | KG East Asia | Gene burden ratio ≤1-Year | Total No. of alleles in gene ≤1-Year | ≥3-Year | No. alt alleles in genes ≤1-Year | ≥3-Year | No. of ≥3-Year cases with alt alleles | Variant allele frequency KG East Asia |
|---|---|---|---|---|---|---|---|---|---|---|---|---|---|---|---|
| 4 | 1 | 87380851 | rs546745 | A | G | HS2ST1 | . | 3.62 | 2.28 | 264 | 232 | 1 | 2 | 2 | 0.006 |
| 4 | 1 | 87563514 | rs143260332 | G | A | HS2ST1 | . | 3.62 | 2.28 | 264 | 232 | 1 | 2 | 2 | 0.004 |
| 4 | 18 | 76886315 | rs200431802 | C | T | ATP9B | D | 3.62 | 2.28 | 264 | 232 | 1 | 2 | 2 | 0.004 |
| 4 | 18 | 77096664 | rs201172611 | G | A | ATP9B | D | 3.62 | 2.28 | 264 | 232 | 1 | 2 | 2 | 0.001 |
| 4 | 18 | 9549345 | rs199964908 | G | A | PPP4R1 | . | 2.72 | 1.71 | 132 | 116 | 2 | 3 | 3 | 0.0079 |
| 4 | 19 | 14071095 | rs140301367 | G | A | DCAF15 | . | 5.43 | 3.41 | 132 | 116 | 1 | 3 | 3 | 0.0079 |
| 4 | 7 | 149521647 | rs564348526 | C | T | SSPO | . | 2.79 | 2.71 | 1484 | 1312 | 5 | 12 | 12 | 0.0069 |
| 4 | 7 | 149521654 | rs578088844 | G | A | SSPO | . | 2.79 | 2.71 | 1484 | 1312 | 5 | 12 | 12 | 0.002 |
| 4 | 7 | 149522951 | rs200469643 | C | T | SSPO | . | 2.79 | 2.71 | 1484 | 1312 | 5 | 12 | 12 | 0.001 |
| 4 | 7 | 75192236 | . | C | A | HIP1 | . | 4.57 | 2.26 | 104 | 92 | 1 | 2 | 2 | 0.0089 |
| 4 | 7 | 75210547 | . | A | T | HIP1 | . | 4.57 | 2.26 | 104 | 92 | 1 | 2 | 2 | 0.001 |
| 4 | 8 | 110439252 | rs375463553 | C | A | PKHD1L1 | D | 4.57 | 2.26 | 208 | 184 | 1 | 2 | 2 | 0.005 |
| 4 | 8 | 110463357 | rs202241413 | C | T | PKHD1L1 | D | 4.57 | 2.26 | 208 | 184 | 1 | 2 | 2 | 0.003 |
| 4 | 8 | 110493660 | rs139600051 | A | G | PKHD1L1 | . | 4.57 | 2.26 | 208 | 184 | 1 | 2 | 2 | 0.005 |
| 4 | 8 | 110527435 | rs559437602 | C | T | PKHD1L1 | D | 4.57 | 2.26 | 208 | 184 | 1 | 2 | 2 | 0.002 |
| 4 | 8 | 145736896 | rs557256260 | C | T | RECQL4 | . | 2.28 | 1.7 | 260 | 230 | 2 | 3 | 3 | 0.001 |
| 4 | 8 | 145738985 | rs536831548 | G | C | RECQL4 | . | 2.28 | 1.7 | 260 | 230 | 2 | 3 | 3 | 0.001 |
| 4 | 8 | 145741388 | rs200097701 | C | G | RECQL4 | . | 2.28 | 1.7 | 260 | 230 | 2 | 3 | 3 | 0.005 |
| 4 | 8 | 145741602 | rs34633809 | C | T | RECQL4 | . | 2.28 | 1.7 | 260 | 230 | 2 | 3 | 3 | 0.0089 |
| 4 | 8 | 145742799 | rs34642881 | T | C | RECQL4 | . | 2.28 | 1.7 | 260 | 230 | 2 | 3 | 3 | 0.0079 |
| 4 | 8 | 17400906 | rs12680645 | G | A | SLC7A2 | D | 3.42 | 1.7 | 156 | 138 | 2 | 3 | 3 | 0.0079 |

TABLE 9-continued

Candidate variant list from RA disease duration comparison.

| group | chr | pos | id | ref | alt | gene | LR | Gene burden ratio KG East Asia | Gene burden ratio ≤1-Year | Total No. of alleles in gene ≤1-Year | Total No. of alleles in gene ≥3-Year | No. alt alleles in genes ≤1-Year | No. alt alleles in genes ≥3-Year | No. of ≥3-Year cases with alt alleles | Variant allele frequency KG East Asia |
|---|---|---|---|---|---|---|---|---|---|---|---|---|---|---|---|
| 4 | 8 | 17407821 | rs188973136 | C | G | SLC7A2 | D | 3.42 | 1.7 | 156 | 138 | 2 | 3 | 3 | 0.006 |
| 4 | 8 | 17417839 | rs201373242 | A | G | SLC7A2 | D | 3.42 | 1.7 | 156 | 138 | 2 | 3 | 3 | 0.001 |
| 4 | 9 | 439392 | rs117109271 | A | G | DOCK8 | . | 3.42 | 3.39 | 104 | 92 | 1 | 3 | 3 | 0.0099 |
| 4 | 9 | 441423 | rs188141951 | C | T | DOCK8 | . | 3.42 | 3.39 | 104 | 92 | 1 | 3 | 3 | 0.003 |
| 4 | X | 1460714 | . | C | T | IL3RA | D | 9.33 | 2.31 | 104 | 90 | 1 | 2 | 2 | 0.001 |
| 4 | X | 1471130 | . | G | T | IL3RA | . | 9.33 | 2.31 | 104 | 90 | 1 | 2 | 2 | 0.004 |
| 4 | 2 | 113342071 | rs528909726 | G | A | CHCHD5 | . | . | . | 38 | 40 | 0 | 2 | 1 | 0.002 |
| 5 | 3 | 63898360 | rs576518931 | G | GGCAGCA | ATXN7 | . | . | 1.76 | 38 | 36 | 3 | 5 | 4 | 0.004 |
| 5 | 4 | 46994972 | rs34464680 | G | GAA | GABRA4 | . | 1.41 | 1.81 | 70 | 54 | 5 | 7 | 6 | 0.0089 |
| 6 | 10 | 122618148 | rs2241846 | G | C | WDR11 | . | 1.57 | 1.67 | 50 | 46 | 15 | 23 | 19 | 0.3472 |
| 6 | 10 | 35485028 | rs137918654 | G | T | CREM | . | 2.74 | 3.39 | 52 | 46 | 1 | 3 | 2 | 0.0347 |
| 6 | 10 | 44788826 | rs58189594 | C | T | C10orf142 | . | 1.87 | 3.39 | 52 | 46 | 3 | 9 | 8 | 0.1121 |
| 6 | 10 | 47087078 | rs2229967 | G | T | CH17-360D5.1 | . | 1.86 | 1.83 | 260 | 230 | 13 | 21 | 21 | . |
| 6 | 10 | 47087078 | rs2229967 | G | T | NPY4R | . | 1.86 | 1.83 | 260 | 230 | 13 | 21 | 21 | . |
| 6 | 10 | 47087403 | rs781881744 | T | C | CH17-360D5.1 | . | 1.86 | 1.83 | 260 | 230 | 13 | 21 | 21 | . |
| 6 | 10 | 47087403 | rs781881744 | T | C | NPY4R | . | 1.86 | 1.83 | 260 | 230 | 13 | 21 | 21 | . |
| 6 | 10 | 47087499 | rs114592738 | G | A | CH17-360D5.1 | . | 1.86 | 1.83 | 260 | 230 | 13 | 21 | 21 | . |
| 6 | 10 | 47087499 | rs114592738 | G | A | NPY4R | . | 1.86 | 1.83 | 260 | 230 | 13 | 21 | 21 | . |
| 6 | 10 | 47087520 | rs115443559 | G | A | CH17-360D5.1 | . | 1.86 | 1.83 | 260 | 230 | 13 | 21 | 21 | 0.0179 |
| 6 | 10 | 47087520 | rs115443559 | G | A | NPY4R | . | 1.86 | 1.83 | 260 | 230 | 13 | 21 | 21 | 0.0179 |

TABLE 9-continued

Candidate variant list from RA disease duration comparison.

| group | chr | pos | id | ref | alt | gene | LR | Gene burden ratio KG East Asia | Gene burden ratio ≤1-Year | Total No. of alleles in gene ≤1-Year | Total No. of alleles in gene ≥3-Year | No. alt alleles in genes ≤1-Year | No. alt alleles in genes ≥3-Year | No. of ≥3-Year cases with alt alleles | Variant allele frequency KG East Asia |
|---|---|---|---|---|---|---|---|---|---|---|---|---|---|---|---|
| 6 | 10 | 47087609 | rs79871698 | G | A | CH17-360D5.1 | . | . | 1.83 | 260 | 230 | 13 | 21 | 21 | 0.0923 |
| 6 | 10 | 47087609 | rs79871698 | G | A | NPY4R | . | 1.86 | 1.83 | 260 | 230 | 13 | 21 | 21 | 0.0923 |
| 6 | 10 | 7747155 | rs76983422 | G | C | ITIH2 | . | 2.74 | 1.7 | 52 | 46 | 2 | 3 | 3 | 0.0397 |
| 6 | 1 | 100617938 | rs78161968 | T | C | LRRC39 | . | 1.68 | 2.29 | 156 | 136 | 3 | 6 | 6 | 0.0446 |
| 6 | 1 | 100618085 | rs773979041 | A | G | LRRC39 | . | 1.68 | 2.29 | 156 | 136 | 3 | 6 | 6 | . |
| 6 | 1 | 100620728 | rs78962557 | G | A | LRRC39 | . | 1.68 | 2.29 | 156 | 136 | 3 | 6 | 6 | 0.0198 |
| 6 | 1 | 109456983 | rs141562079 | C | T | GPSM2 | D | 2.28 | 6.78 | 156 | 138 | 1 | 6 | 6 | 0.0258 |
| 6 | 1 | 109465156 | rs199964596 | TCAA | T | GPSM2 | . | 2.28 | 6.78 | 156 | 138 | 1 | 6 | 6 | 0.0129 |
| 6 | 1 | 109465165 | rs35029887 | ACTT | A | GPSM2 | . | 2.28 | 6.78 | 156 | 138 | 1 | 6 | 6 | . |
| 6 | 11 | 118886656 | rs7131534 | G | A | RPS25 | . | 1.52 | 1.7 | 52 | 46 | 2 | 3 | 3 | 0.0704 |
| 6 | 11 | 13410690 | rs375824034 | TGAAA | T | BTBD10 | . | 2.49 | 1.7 | 52 | 46 | 4 | 6 | 6 | 0.0675 |
| 6 | 11 | 16812551 | rs116885602 | C | T | PLEKHA7 | . | 1.61 | 1.85 | 100 | 90 | 6 | 10 | 9 | 0.0456 |
| 6 | 11 | 16863087 | rs452745 | A | G | PLEKHA7 | . | 1.61 | 1.85 | 100 | 90 | 6 | 10 | 9 | 0.1617 |
| 6 | 11 | 118530450 | rs184368389 | T | C | SPAG17 | . | 4.57 | 3.39 | 52 | 46 | 1 | 3 | 3 | 0.0179 |
| 6 | 1 | 12082881 | rs11588779 | C | T | MIIP | . | 4.57 | 3.39 | 52 | 46 | 2 | 6 | 6 | 0.0685 |
| 6 | 11 | 22232870 | rs78987921 | G | A | ANO5 | . | 4.57 | 2.26 | 104 | 92 | 1 | 2 | 2 | 0.0109 |
| 6 | 11 | 22239801 | . | C | T | ANO5 | . | 4.57 | 2.26 | 104 | 92 | 1 | 2 | 2 | . |
| 6 | 11 | 32636495 | rs145888197 | T | C | CCDC73 | . | 1.52 | 2.26 | 52 | 46 | 1 | 2 | 2 | 0.0377 |
| 6 | 1 | 145414790 | . | G | C | HFE2 | . | 4.57 | 2.26 | 52 | 46 | 1 | 2 | 2 | 0.0129 |
| 6 | 1 | 145456731 | rs6694055 | G | C | POLR3GL | . | 1.83 | 2.26 | 52 | 46 | 1 | 2 | 2 | 0.0119 |
| 6 | 1 | 145527604 | rs2274620 | A | G | ITGA10 | . | 1.62 | 2.94 | 260 | 230 | 5 | 13 | 12 | 0.0208 |

TABLE 9-continued

Candidate variant list from RA disease duration comparison.

| group | chr | pos | id | ref | alt | gene | LR | Gene burden ratio KG East Asia | Gene burden ratio ≤1-Year | Total No. of alleles in gene ≤1-Year | Total No. of alleles in gene ≥3-Year | No. alt alleles in genes ≤1-Year | No. alt alleles in genes ≥3-Year | No. of ≥3-Year cases with alt alleles | Variant allele frequency KG East Asia |
|---|---|---|---|---|---|---|---|---|---|---|---|---|---|---|---|
| 6 | 1 | 145534221 | . | G | T | ITGA10 | . | 1.62 | 2.94 | 260 | 230 | 5 | 13 | 12 | . |
| 6 | 1 | 145536082 | rs2274616 | G | A | ITGA10 | . | 1.62 | 2.94 | 260 | 230 | 5 | 13 | 12 | 0.0704 |
| 6 | 1 | 145541806 | rs77912414 | T | C | ITGA10 | . | 1.62 | 2.94 | 260 | 230 | 5 | 13 | 12 | 0.0119 |
| 6 | 1 | 152484245 | rs2282298 | C | T | LCE5A | . | 2.28 | 3.39 | 52 | 46 | 1 | 3 | 3 | 0.0228 |
| 6 | 1 | 155136125 | rs117954374 | C | T | OR4A15 | . | 2.08 | 2.83 | 52 | 46 | 2 | 5 | 5 | 0.0585 |
| 6 | 11 | 551644 | rs113026126 | C | T | LRRC56 | . | 2.54 | 1.88 | 52 | 46 | 3 | 5 | 5 | 0.0476 |
| 6 | 11 | 5776484 | rs4910844 | A | T | OR52N4 | . | 1.56 | 2.64 | 52 | 46 | 6 | 14 | 10 | 0.1974 |
| 6 | 1 | 15834360 | rs2020902 | A | G | CASP9 | . | 3.04 | 2.26 | 52 | 46 | 1 | 2 | 2 | 0.0317 |
| 6 | 1 | 15860803 | rs11583306 | C | T | DNAJC16 | . | 2.74 | 1.7 | 52 | 46 | 2 | 3 | 3 | 0.0466 |
| 6 | 1 | 159799808 | rs10430458 | C | T | SLAMF8 | . | 3.42 | 1.7 | 52 | 46 | 2 | 3 | 3 | 0.0317 |
| 6 | 1 | 159958290 | rs3795334 | T | A | CFAP45 | . | 1.52 | 2.83 | 52 | 46 | 2 | 5 | 5 | 0.0556 |
| 6 | 11 | 61048196 | rs78505441 | G | C | VWCE | . | 1.83 | 2.26 | 52 | 46 | 1 | 2 | 2 | 0.0268 |
| 6 | 11 | 61071331 | rs28720346 | C | T | DDB1 | . | 1.83 | 2.26 | 52 | 46 | 1 | 2 | 2 | 0.0258 |
| 6 | 11 | 62365619 | rs11231155 | A | G | MTA2 | . | 1.83 | 2.26 | 52 | 46 | 2 | 4 | 4 | 0.0526 |
| 6 | 11 | 62369881 | rs35156678 | G | A | EML3 | . | 2.03 | 2.26 | 52 | 46 | 2 | 4 | 4 | 0.0437 |
| 6 | 1 | 16382911 | rs72474563 | A | G | CLCNKB | . | 9.13 | 2.26 | 52 | 46 | 2 | 4 | 4 | 0.0357 |
| 6 | 11 | 67771408 | rs188940236 | C | T | UNC93B1 | . | 1.62 | 2.2 | 44 | 40 | 2 | 4 | 4 | 0.0308 |
| 6 | 1 | 168105581 | rs200664972 | A | AG | GPR161 | . | 1.83 | 4.52 | 52 | 46 | 1 | 4 | 4 | 0.0516 |
| 6 | 11 | 71710425 | rs373342292 | CTCA | C | IL18BP | . | 3.65 | . | 52 | 46 | 0 | 4 | 4 | 0.0198 |
| 6 | 1 | 177247693 | rs138799872 | C | T | BRINP2 | . | 4.57 | 2.26 | 52 | 46 | 1 | 2 | 2 | 0.0119 |
| 6 | 11 | 797714 | . | T | A | PANO1 | . | 7.72 | 2.83 | 154 | 136 | 2 | 5 | 5 | . |

TABLE 9-continued

Candidate variant list from RA disease duration comparison.

| group | chr | pos | id | ref | alt | gene | LR | KG East Asia | Gene burden ratio ≤1-Year | Total No. of alleles in gene ≤1-Year | ≥3-Year | No. alt alleles in genes ≤1-Year | ≥3-Year | No. of ≥3-Year cases with alt alleles | Variant allele frequency KG East Asia |
|---|---|---|---|---|---|---|---|---|---|---|---|---|---|---|---|
| 6 | 11 | 798082 | rs201547522 | C | CT | PANO1 | . | 7.72 | 2.83 | 154 | 136 | 2 | 5 | 5 | 0.0248 |
| 6 | 11 | 798222 | rs572464433 | T | TCGC | PANO1 | . | 7.72 | 2.83 | 154 | 136 | 2 | 5 | 5 | . |
| 6 | 1 | 180240510 | rs2764449 | T | C | LHX4 | . | 2.28 | . | 156 | 138 | 0 | 3 | 3 | 0.0139 |
| 6 | 1 | 180243593 | rs200119009 | C | T | LHX4 | D | 2.28 | . | 156 | 138 | 0 | 3 | 3 | . |
| 6 | 1 | 180243601 | . | G | A | LHX4 | D | 2.28 | . | 156 | 138 | 0 | 3 | 3 | . |
| 6 | 1 | 201356001 | . | CCCA | * | LAD1 | . | 4.38 | 1.92 | 184 | 160 | 12 | 20 | 20 | 0.0575 |
| 6 | 1 | 201356001 | rs398053706 | CCCA | C | LAD1 | . | 4.38 | 1.92 | 184 | 160 | 12 | 20 | 20 | . |
| 6 | 1 | 201356004 | . | ACC | * | LAD1 | . | 4.38 | 1.92 | 184 | 160 | 12 | 20 | 20 | . |
| 6 | 1 | 201356004 | rs552300739 | ACC | A | LAD1 | . | 4.38 | 1.92 | 184 | 160 | 12 | 20 | 20 | 0.0486 |
| 6 | 1 | 210267893 | rs144713062 | TGAA | T | SYT14 | . | 3.2 | 3.96 | 52 | 46 | 2 | 7 | 6 | 0.0655 |
| 6 | 1 | 110923012 | rs142702785 | A | G | FAM216A | . | 2.74 | . | 52 | 46 | 0 | 3 | 3 | 0.0149 |
| 6 | 1 | 113592306 | rs200344876 | G | GC | CFAP73 | . | 3.42 | 3.39 | 52 | 46 | 1 | 3 | 3 | 0.0169 |
| 6 | 1 | 2117557 | rs547643542 | G | A | FAAP20 | . | 3.65 | 1.51 | 104 | 92 | 6 | 8 | 7 | 0.0139 |
| 6 | 12 | 122243731 | rs557334621 | C | T | SETD1B | . | 2.28 | 2.26 | 156 | 138 | 1 | 2 | 2 | . |
| 6 | 12 | 122255354 | rs541427059 | TGCG | T | SETD1B | . | 2.28 | 2.26 | 156 | 138 | 1 | 2 | 2 | 0.0129 |
| 6 | 12 | 122265770 | rs111774166 | G | A | SETD1B | . | 2.28 | 2.26 | 156 | 138 | 1 | 2 | 2 | 0.0188 |
| 6 | 12 | 12630665 | rs142947418 | TGCACGCTGG (SEQ ID NO: 10) | T | DUSP16 | . | 1.55 | 1.64 | 178 | 154 | 48 | 68 | 57 | 0.13 |
| 6 | 12 | 12630675 | rs201941751 | GCACGC | G | DUSP16 | . | 1.55 | 1.64 | 178 | 154 | 48 | 68 | 57 | 0.2698 |
| 6 | 12 | 12630681 | rs200271649 | TGGGC | T | DUSP16 | . | 1.55 | 1.64 | 178 | 154 | 48 | 68 | 57 | 0.2698 |
| 6 | 12 | 12633287 | rs10845555 | A | G | DUSP16 | . | 1.55 | 1.64 | 178 | 154 | 48 | 68 | 57 | 0.4097 |
| 6 | 1 | 2130262 | rs144802031 | C | G | FAAP20 | . | 3.65 | 1.51 | 104 | 92 | 6 | 8 | 7 | 0.0754 |

TABLE 9-continued

Candidate variant list from RA disease duration comparison.

| group | chr | pos | id | ref | alt | gene | LR | Gene burden ratio KG East Asia | Gene burden ratio ≤1-Year | Total No. of alleles in gene ≤1-Year | Total No. of alleles in gene ≥3-Year | No. alt alleles in genes ≤1-Year | No. alt alleles in genes ≥3-Year | No. of ≥3-Year cases with alt alleles | Variant allele frequency KG East Asia |
|---|---|---|---|---|---|---|---|---|---|---|---|---|---|---|---|
| 6 | 12 | 14923935 | rs199781231 | T | TC | HIST4H4 | . | 1.52 | 2.26 | 52 | 46 | 1 | 2 | 2 | 0.0198 |
| 6 | 12 | 16377347 | rs117974895 | C | T | SLC15A5 | . | 2.28 | 1.7 | 52 | 46 | 2 | 3 | 3 | 0.0337 |
| 6 | 1 | 224008913 | rs3738370 | G | A | TP53BP2 | . | 1.89 | 1.51 | 52 | 46 | 9 | 12 | 11 | 0.1925 |
| 6 | 1 | 228289872 | rs373634959 | G | A | C1orf35 | . | 2.28 | 2.26 | 52 | 46 | 1 | 2 | 2 | 0.0139 |
| 6 | 1 | 22924364 | rs72651347 | G | A | EPHA8 | . | 2.28 | 1.7 | 104 | 92 | 2 | 3 | 3 | 0.0179 |
| 6 | 1 | 22927298 | rs569320402 | C | T | EPHA8 | D | 2.28 | 1.7 | 104 | 92 | 2 | 3 | 3 | . |
| 6 | 1 | 234509972 | rs73099933 | A | G | COA6 | . | 2.5 | 2.89 | 52 | 42 | 3 | 7 | 7 | 0.0804 |
| 6 | 1 | 247719769 | rs56043070 | G | A | GCSAML | . | 2.28 | 3.39 | 52 | 46 | 1 | 3 | 3 | 0.0327 |
| 6 | 1 | 248512939 | rs201185608 | AC | A | OR14C36 | . | 1.76 | 1.88 | 52 | 46 | 3 | 5 | 5 | 0.0615 |
| 6 | 12 | 49721122 | rs73309977 | C | T | TROAP | . | 1.96 | 3.39 | 52 | 46 | 1 | 3 | 3 | 0.0397 |
| 6 | 12 | 51510213 | rs77417603 | T | A | TFCP2 | . | 2.28 | 2.26 | 52 | 46 | 2 | 4 | 4 | 0.0228 |
| 6 | 12 | 52156281 | rs187002252 | A | G | SCN8A | . | 1.83 | 2.26 | 52 | 46 | 1 | 2 | 2 | 0.0179 |
| 6 | 12 | 53427826 | rs140133257 | G | T | EIF4B | . | 2.74 | . | 52 | 46 | 0 | 3 | 3 | 0.0228 |
| 6 | 12 | 54756528 | rs77759698 | A | G | GPR84 | D | 1.76 | 5.65 | 52 | 46 | 1 | 5 | 5 | 0.0347 |
| 6 | 12 | 55523586 | rs398102299 | AT | A | OR9K2 | . | 1.66 | 3.01 | 52 | 46 | 3 | 8 | 7 | 0.1141 |
| 6 | 12 | 55641255 | rs4522268 | C | T | OR6C74 | . | 1.96 | 3.39 | 52 | 46 | 3 | 9 | 8 | 0.1171 |
| 6 | 12 | 55759191 | rs398102300 | AT | A | OR6C75 | . | 2.28 | 3.96 | 52 | 46 | 2 | 7 | 7 | 0.0724 |
| 6 | 12 | 58007149 | rs141337782 | G | C | ARHGEF25 | . | 1.52 | 2.83 | 52 | 46 | 2 | 5 | 4 | 0.1151 |
| 6 | 1 | 26524503 | rs199601379 | C | T | CATSPER4 | D | 1.71 | 3.39 | 104 | 92 | 1 | 3 | 2 | . |
| 6 | 1 | 26526554 | rs6700024 | G | A | CATSPER4 | . | 1.71 | 3.39 | 104 | 92 | 1 | 3 | 2 | 0.0208 |
| 6 | 12 | 70928745 | rs3752702 | G | A | PTPRB | . | 3.04 | 2.26 | 52 | 46 | 1 | 2 | 2 | 0.0486 |

TABLE 9-continued

Candidate variant list from RA disease duration comparison.

| group | chr | pos | id | ref | alt | gene | LR | KG East Asia | Gene burden ratio ≤1-Year | Total No. of alleles in gene ≤1-Year | ≥3-Year | No. alt alleles in genes ≤1-Year | ≥3-Year | No. of ≥3-Year cases with alt alleles | Variant allele frequency KG East Asia |
|---|---|---|---|---|---|---|---|---|---|---|---|---|---|---|---|
| 6 | 12 | 95456367 | rs138805411 | T | C | NR2C1 | D | 4.57 | 4.52 | 52 | 46 | 1 | 4 | 4 | 0.0208 |
| 6 | 13 | 76457183 | rs9530477 | T | C | LMO7DN | . | 1.66 | 1.88 | 52 | 46 | 12 | 20 | 15 | 0.3284 |
| 6 | 14 | 35182348 | rs35515423 | GA | G | CFL2 | . | 1.55 | 1.7 | 46 | 44 | 8 | 13 | 11 | 0.2034 |
| 6 | 14 | 94750501 | rs77844573 | A | G | SERPINA10 | . | 1.6 | 1.98 | 104 | 92 | 4 | 7 | 7 | 0.0258 |
| 6 | 14 | 94756458 | rs2232699 | A | T | SERPINA10 | D | 1.6 | 1.98 | 104 | 92 | 4 | 7 | 7 | 0.0298 |
| 6 | 15 | 101013123 | rs1566775 | G | A | CERS3 | . | 4.57 | 2.26 | 52 | 46 | 1 | 2 | 2 | 0.0258 |
| 6 | 15 | 101601367 | rs148929418 | C | CACTT | LRRK1 | . | 3.26 | 2.26 | 52 | 46 | 5 | 10 | 10 | 0.1409 |
| 6 | 15 | 28947605 | rs3893142 | C | A | GOLGA8M | . | 1.75 | 1.53 | 46 | 40 | 3 | 4 | 4 | 0.0675 |
| 6 | 15 | 60803458 | rs779626945 | C | T | RORA | D | 2.28 | . | 104 | 92 | 0 | 3 | 3 | . |
| 6 | 15 | 60919432 | rs73424068 | C | T | RORA | . | 2.28 | . | 104 | 92 | 0 | 3 | 3 | 0.0149 |
| 6 | 15 | 78458485 | rs3816253 | T | C | IDH3A | . | 1.64 | 1.58 | 52 | 46 | 10 | 14 | 11 | 0.1885 |
| 6 | 16 | 1272750 | rs113856625 | G | A | TPSG1 | D | 2.13 | 3.96 | 104 | 92 | 2 | 7 | 7 | . |
| 6 | 16 | 1273444 | rs61587627 | G | T | TPSG1 | D | 2.13 | 3.96 | 104 | 92 | 2 | 7 | 7 | 0.0972 |
| 6 | 16 | 13297242 | rs13331224 | C | T | SHISA9 | . | 1.64 | 1.57 | 48 | 46 | 6 | 9 | 9 | 0.1042 |
| 6 | 16 | 1825689 | rs3826055 | C | T | EME2 | . | 6.85 | 1.7 | 104 | 92 | 2 | 3 | 3 | 0.0129 |
| 6 | 16 | 1825789 | rs746707908 | T | C | EME2 | . | 6.85 | 1.7 | 104 | 92 | 2 | 3 | 3 | . |
| 6 | 1 | 6266793 | rs72853039 | G | C | RNF207 | . | 1.71 | 3.39 | 52 | 46 | 2 | 6 | 6 | 0.0972 |
| 6 | 16 | 28998111 | rs4788115 | T | A | LAT | . | 1.74 | 2.26 | 52 | 46 | 4 | 8 | 8 | 0.1359 |
| 6 | 16 | 30455945 | rs146596728 | A | C | SEPHS2 | . | 4.57 | 2.26 | 104 | 92 | 1 | 2 | 2 | 0.0248 |
| 6 | 16 | 30456188 | rs550048089 | G | A | SEPHS2 | . | 4.57 | 2.26 | 104 | 92 | 1 | 2 | 2 | . |
| 6 | 16 | 3075701 | rs27117664 | C | T | THOC6 | . | 1.72 | 2.75 | 104 | 92 | 14 | 34 | 28 | 0.1825 |
| 6 | 16 | 3075999 | rs2245000 | C | G | THOC6 | . | 1.72 | 2.75 | 104 | 92 | 14 | 34 | 28 | 0.3046 |

TABLE 9-continued

Candidate variant list from RA disease duration comparison.

| group | chr | pos | id | ref | alt | gene | LR | Gene burden ratio KG East Asia | Gene burden ratio ≤1-Year | Total No. of alleles in gene ≤1-Year | Total No. of alleles in gene ≥3-Year | No. alt alleles in genes ≤1-Year | No. alt alleles in genes ≥3-Year | No. of ≥3-Year cases with alt alleles | Variant allele frequency KG East Asia |
|---|---|---|---|---|---|---|---|---|---|---|---|---|---|---|---|
| 6 | 16 | 3554840 | rs80187466 | G | T | CLUAP1 | . | 1.96 | . | 156 | 138 | 0 | 9 | 9 | 0.0556 |
| 6 | 16 | 3558283 | rs59492947 | A | T | CLUAP1 | . | 1.96 | . | 156 | 138 | 0 | 9 | 9 | 0.0556 |
| 6 | 16 | 3580565 | rs79684678 | T | C | CLUAP1 | . | 1.96 | . | 156 | 138 | 0 | 9 | 9 | 0.0556 |
| 6 | 16 | 5077897 | rs112669475 | G | A | NAGPA | . | 2.03 | . | 52 | 46 | 0 | 4 | 4 | 0.0397 |
| 6 | 16 | 57736047 | rs72795521 | G | A | DRC7 | . | 1.71 | 1.7 | 156 | 138 | 14 | 21 | 17 | 0.2669 |
| 6 | 16 | 57756907 | rs113469607 | C | A | DRC7 | . | 1.71 | 1.7 | 156 | 138 | 14 | 21 | 17 | 0.0218 |
| 6 | 16 | 57757046 | rs139945134 | C | T | DRC7 | . | 1.71 | 1.7 | 156 | 138 | 14 | 21 | 17 | 0.0129 |
| 6 | 1 | 6647702 | rs183072854 | G | A | ZBTB48 | . | 3.04 | 2.26 | 52 | 46 | 1 | 2 | 2 | 0.0268 |
| 6 | 16 | 67180171 | rs7184692 | T | C | C16orf70 | . | 2.54 | 2.83 | 52 | 46 | 2 | 5 | 5 | 0.0595 |
| 6 | 16 | 83998662 | rs733728 | A | G | OSGIN1 | . | 1.68 | . | 52 | 46 | 0 | 7 | 7 | 0.0962 |
| 6 | 16 | 84801966 | rs189466547 | T | C | USP10 | . | 4.57 | 2.26 | 52 | 46 | 1 | 2 | 2 | 0.0109 |
| 6 | 17 | 27067480 | rs750108245 | G | A | NEK8 | . | 1.9 | 2.83 | 208 | 184 | 2 | 5 | 5 | . |
| 6 | 17 | 27067558 | rs565763400 | C | T | NEK8 | . | 1.9 | 2.83 | 208 | 184 | 2 | 5 | 5 | . |
| 6 | 17 | 27068005 | rs147832976 | TGAG | T | NEK8 | . | 1.9 | 2.83 | 208 | 184 | 2 | 5 | 5 | 0.0407 |
| 6 | 17 | 27068012 | rs757972103 | G | T | NEK8 | . | 1.9 | 2.83 | 208 | 184 | 2 | 5 | 5 | . |
| 6 | 17 | 34182099 | rs149317141 | G | GT | HEATR9 | . | 1.56 | 1.7 | 156 | 138 | 20 | 30 | 27 | 0.0198 |
| 6 | 17 | 34185535 | rs35283303 | AG | A | HEATR9 | . | 1.56 | 1.7 | 156 | 138 | 20 | 30 | 27 | 0.3224 |
| 6 | 17 | 34192406 | . | G | A | HEATR9 | . | 1.56 | 1.7 | 156 | 138 | 20 | 30 | 27 | 0.0952 |
| 6 | 17 | 36895514 | rs72819704 | A | G | PCGF2 | . | 1.63 | 1.88 | 104 | 92 | 6 | 10 | 9 | 0.0169 |
| 6 | 17 | 36896534 | rs2075057 | C | T | PCGF2 | . | 1.63 | 1.88 | 104 | 92 | 6 | 10 | 9 | 0.0962 |
| 6 | 17 | 37824838 | . | GCAA | G | PNMT | . | 2.28 | 4.52 | 104 | 92 | 1 | 4 | 4 | . |

TABLE 9-continued

Candidate variant list from RA disease duration comparison.

| group | chr | pos | id | ref | alt | gene | LR | Gene burden ratio KG East Asia | Gene burden ratio ≤1-Year | Total No. of alleles in gene ≤1-Year | Total No. of alleles in gene ≥3-Year | No. alt alleles in genes ≤1-Year | No. alt alleles in genes ≥3-Year | No. of ≥3-Year cases with alt alleles | Variant allele frequency KG East Asia |
|---|---|---|---|---|---|---|---|---|---|---|---|---|---|---|---|
| 6 | 17 | 37826201 | rs60871117 | C | T | PNMT | . | 2.28 | 4.52 | 104 | 92 | 1 | 4 | 4 | 0.0357 |
| 6 | 17 | 48753044 | rs371874263 | C | T | ABCC3 | D | 2.28 | 1.51 | 208 | 184 | 3 | 4 | 4 | . |
| 6 | 17 | 48755450 | rs11568583 | A | G | ABCC3 | . | 2.28 | 1.51 | 208 | 184 | 3 | 4 | 4 | 0.0258 |
| 6 | 17 | 48761020 | rs572541933 | G | A | ABCC3 | D | 2.28 | 1.51 | 208 | 184 | 3 | 4 | 4 | . |
| 6 | 17 | 48765100 | rs756871504 | C | T | ABCC3 | . | 2.28 | 1.51 | 208 | 184 | 3 | 4 | 4 | . |
| 6 | 17 | 4906146 | rs10533622 | GC | G | KIF1C | . | 1.7 | 1.75 | 164 | 194 | 30 | 62 | 53 | 0.3244 |
| 6 | 17 | 4906146 | rs146311497 | GCC | GC | KIF1C | . | 1.7 | 1.75 | 164 | 194 | 30 | 62 | 53 | . |
| 6 | 17 | 4906146 | rs763524690 | G | A | KIF1C | . | 1.7 | 1.75 | 164 | 194 | 30 | 62 | 53 | . |
| 6 | 17 | 4907374 | rs766141834 | G | A | KIF1C | . | 1.7 | 1.75 | 164 | 194 | 30 | 62 | 53 | 0.0446 |
| 6 | 17 | 4924097 | rs4790725 | C | G | KIF1C | . | 1.7 | 1.75 | 164 | 194 | 30 | 62 | 53 | 0.1667 |
| 6 | 17 | 59667953 | rs17610181 | G | A | NACA2 | . | 1.77 | 1.94 | 52 | 46 | 7 | 12 | 11 | . |
| 6 | 17 | 64876769 | rs376464596 | C | T | CACNG5 | D | 2.09 | 1.55 | 156 | 138 | 8 | 11 | 9 | . |
| 6 | 17 | 64876770 | rs142916987 | G | A | CACNG5 | D | 2.09 | 1.55 | 156 | 138 | 8 | 11 | 9 | 0.126 |
| 6 | 17 | 64880788 | rs2286677 | G | A | CACNG5 | . | 2.09 | 1.55 | 156 | 138 | 8 | 11 | 9 | 0.0804 |
| 6 | 17 | 76130947 | rs62079073 | G | T | TMC8 | . | 1.52 | 1.58 | 52 | 46 | 5 | 7 | 7 | 0.0159 |
| 6 | 17 | 8109965 | rs144397670 | G | A | AURKB | . | 1.71 | 3.36 | 206 | 184 | 1 | 3 | 3 | . |
| 6 | 17 | 8110079 | rs139322514 | G | A | AURKB | . | 1.71 | 3.36 | 206 | 184 | 1 | 3 | 3 | . |
| 6 | 17 | 8113270 | rs766965552 | A | G | AURKB | . | 1.71 | 3.36 | 206 | 184 | 1 | 3 | 3 | . |
| 6 | 17 | 8113544 | . | C | G | AURKB | . | 1.71 | 3.36 | 206 | 184 | 0 | 3 | 3 | . |
| 6 | 18 | 33694444 | rs148550301 | A | G | SLC39A6 | . | 4.57 | . | 52 | 46 | 5 | 9 | 9 | 0.0298 |
| 6 | 1 | 89523927 | rs60070945 | C | T | GBP1 | . | 1.71 | 2.03 | 52 | 46 | 1 | 2 | 2 | 0.12 |
| 6 | 19 | 10426524 | rs79442975 | G | A | FDX1L | . | 1.83 | 2.26 | 52 | 46 | 1 | 2 | 2 | 0.0397 |

TABLE 9-continued

Candidate variant list from RA disease duration comparison.

| group | chr | pos | id | ref | alt | gene | LR | Gene burden ratio KG East Asia | Gene burden ratio ≤1-Year | Total No. of alleles in gene ≤1-Year | Total No. of alleles in gene ≥3-Year | No. alt alleles in genes ≤1-Year | No. alt alleles in genes ≥3-Year | No. of ≥3-Year cases with alt alleles | Variant allele frequency KG East Asia |
|---|---|---|---|---|---|---|---|---|---|---|---|---|---|---|---|
| 6 | 19 | 12875807 | rs115585485 | A | C | HOOK2 | . | 1.96 | 3.39 | 52 | 46 | 1 | 3 | 3 | 0.0238 |
| 6 | 19 | 1917687 | rs138069352 | C | G | SCAMP4 | . | 1.71 | 3.39 | 52 | 46 | 1 | 3 | 3 | 0.0437 |
| 6 | 1 | 92798945 | rs78196083 | C | T | RPAP2 | . | 1.52 | 2.26 | 52 | 46 | 1 | 2 | 2 | 0.0456 |
| 6 | 19 | 32083223 | rs11880125 | A | G | THEG5 | . | 4.57 | 1.7 | 104 | 92 | 4 | 6 | 6 | 0.0179 |
| 6 | 19 | 32083250 | rs79323410 | T | C | THEG5 | . | 4.57 | 1.7 | 104 | 92 | 4 | 6 | 6 | 0.0179 |
| 6 | 19 | 39905903 | rs3859551 | A | G | PLEKHG2 | . | 1.64 | 1.7 | 260 | 230 | 4 | 6 | 6 | 0.0387 |
| 6 | 19 | 39906985 | rs10401595 | T | C | PLEKHG2 | . | 1.64 | 1.7 | 260 | 230 | 4 | 6 | 6 | 0.0387 |
| 6 | 19 | 39907573 | rs763779951 | C | G | PLEKHG2 | D | 1.64 | 1.7 | 260 | 230 | 4 | 6 | 6 | . |
| 6 | 19 | 39915627 | rs200639701 | A | G | PLEKHG2 | D | 1.64 | 1.7 | 260 | 230 | 4 | 6 | 6 | . |
| 6 | 19 | 39915764 | . | A | G | PLEKHG2 | D | 1.64 | 1.7 | 260 | 230 | 4 | 6 | 6 | . |
| 6 | 19 | 39948307 | rs2304215 | C | T | SUPT5H | . | 1.52 | 2.26 | 52 | 46 | 1 | 2 | 2 | 0.0129 |
| 6 | 19 | 40327312 | rs3760924 | A | G | FBL | . | 2.28 | 2.54 | 52 | 46 | 4 | 9 | 8 | 0.0992 |
| 6 | 19 | 42603776 | rs1205817 | A | G | POU2F2 | . | 1.52 | 1.7 | 52 | 46 | 8 | 12 | 11 | 0.1865 |
| 6 | 19 | 43268140 | rs11355507 | AG | A | PSG8 | . | 1.96 | 1.7 | 52 | 46 | 2 | 3 | 3 | 0.0188 |
| 6 | 19 | 45296846 | rs66944506 | A | AC | CBLC | . | 1.68 | 1.98 | 104 | 92 | 4 | 7 | 7 | 0.0962 |
| 6 | 19 | 45297454 | rs1903831 | A | C | CBLC | . | 1.68 | 1.98 | 104 | 92 | 4 | 7 | 7 | 0.0863 |
| 6 | 19 | 47290651 | rs3826793 | G | T | SLC1A5 | . | 1.56 | 1.63 | 52 | 46 | 9 | 13 | 11 | 0.2212 |
| 6 | 19 | 48735017 | rs140826611 | C | CTT | CARD8 | . | 2.28 | 1.51 | 52 | 46 | 3 | 4 | 4 | 0.0575 |
| 6 | 19 | 49956688 | rs78750735 | T | C | ALDH16A1 | . | 1.8 | 1.72 | 208 | 180 | 39 | 58 | 52 | . |
| 6 | 19 | 49965131 | rs76844851 | G | A | ALDH16A1 | . | 1.8 | 1.72 | 208 | 180 | 39 | 58 | 52 | 0.3313 |
| 6 | 19 | 49965131 | rs76844851 | G | C | ALDH16A1 | . | 1.8 | 1.72 | 208 | 180 | 39 | 58 | 52 | 0.0149 |

TABLE 9-continued

Candidate variant list from RA disease duration comparison.

| group | chr | pos | id | ref | alt | gene | LR | Gene burden ratio KG East Asia | Gene burden ratio ≤1-Year | Total No. of alleles in gene ≤1-Year | Total No. of alleles in gene ≥3-Year | No. alt alleles in genes ≤1-Year | No. alt alleles in genes ≥3-Year | No. of ≥3-Year cases with alt alleles | Variant allele frequency KG East Asia |
|---|---|---|---|---|---|---|---|---|---|---|---|---|---|---|---|
| 6 | 19 | 49965132 | rs79109084 | G | C | ALDH16A1 | . | 1.8 | 1.72 | 208 | 180 | 39 | 58 | 52 | 0.3313 |
| 6 | 19 | 51330423 | rs61752560 | C | G | KLK15 | . | 2.28 | 1.81 | 52 | 46 | 5 | 8 | 7 | 0.1032 |
| 6 | 19 | 51582802 | rs199715229 | C | T | KLK14 | D | 4.57 | 2.26 | 104 | 92 | 1 | 2 | 2 | 0.0119 |
| 6 | 19 | 51585822 | rs769468261 | G | A | KLK14 | . | 4.57 | 2.26 | 104 | 92 | 1 | 2 | 2 | . |
| 6 | 19 | 54578105 | . | C | T | TARM1 | . | 2.74 | . | 52 | 46 | 0 | 3 | 3 | 0.0268 |
| 6 | 19 | 58118371 | rs78803667 | G | A | ZNF530 | D | 6.85 | 3.39 | 52 | 46 | 1 | 3 | 3 | 0.0159 |
| 6 | 19 | 7688614 | rs2335521 | T | C | XAB2 | . | 2.85 | 5.65 | 52 | 46 | 1 | 5 | 5 | 0.0407 |
| 6 | 19 | 7935408 | . | A | ACACTGGGGGTGAGGCAGGGGAGAGAAAGGGCCTG (SEQ ID NO: 11) | PRR36 | . | 6.49 | 6.74 | 218 | 194 | 1 | 6 | 6 | . |
| 6 | 19 | 7935423 | rs759755075 | CAGGGGGAGAGAAAGGGGCCTGCACTGGGGGTGAGGG (SEQ ID NO: 12) | C | PRR36 | . | 6.49 | 6.74 | 218 | 194 | 1 | 6 | 6 | . |
| 6 | 19 | 7936105 | . | A | T | PRR36 | . | 6.49 | 6.74 | 218 | 194 | 1 | 6 | 6 | . |
| 6 | 19 | 7937299 | . | C | T | PRR36 | . | 6.49 | 6.74 | 218 | 194 | 1 | 6 | 6 | . |
| 6 | 19 | 829555 | rs144713752 | C | G | AZU1 | . | 2.74 | . | 52 | 46 | 0 | 3 | 3 | 0.0129 |
| 6 | 19 | 9236698 | rs111279560 | G | GATGGT | OR7G3 | . | 1.51 | 1.64 | 152 | 134 | 18 | 26 | 22 | 0.3651 |
| 6 | 19 | 9236916 | rs75266995 | AG | A | OR7G3 | . | 1.51 | 1.64 | 152 | 134 | 18 | 26 | 22 | 0.0317 |
| 6 | 19 | 9236969 | rs61751875 | G | A | OR7G3 | . | 1.51 | 1.64 | 152 | 134 | 18 | 26 | 22 | 0.0357 |
| 6 | 20 | 23584368 | rs118095359 | G | A | CST9 | . | 1.83 | 2.26 | 52 | 46 | 1 | 2 | 2 | 0.0129 |
| 6 | 20 | 31672812 | rs71349705 | C | T | BPIFB4 | . | 6.85 | . | 104 | 92 | 0 | 3 | 3 | . |

TABLE 9-continued

Candidate variant list from RA disease duration comparison.

| group | chr | pos | id | ref | alt | gene | LR | Gene burden ratio KG East Asia | Gene burden ratio ≤1-Year | Total No of alleles in gene ≤1-Year | Total No of alleles in gene ≥3-Year | No. alt alleles in genes ≤1-Year | No. alt alleles in genes ≥3-Year | No. of ≥3-Year cases with alt alleles | Variant allele frequency KG East Asia |
|---|---|---|---|---|---|---|---|---|---|---|---|---|---|---|---|
| 6 | 20 | 31677295 | rs142982767 | C | T | BPIFB4 | . | 6.85 | . | 104 | 92 | 0 | 3 | 3 | 0.0179 |
| 6 | 20 | 32005736 | rs116972153 | G | A | SNTA1 | . | 1.52 | 1.7 | 52 | 46 | 2 | 3 | 3 | 0.0238 |
| 6 | 20 | 4228485 | rs3746669 | G | T | ADRA1D | . | 1.5 | 2.26 | 52 | 46 | 11 | 22 | 17 | 0.2887 |
| 6 | 20 | 44180813 | rs17348421 | G | A | WFDC8 | . | 2.28 | 2.83 | 52 | 46 | 2 | 5 | 4 | 0.0585 |
| 6 | 20 | 44511257 | rs35972756 | G | A | ZSWIM1 | . | 4.57 | 2.26 | 52 | 46 | 1 | 2 | 2 | 0.0159 |
| 6 | 20 | 44676727 | rs12481488 | T | A | SLC12A5 | . | 3.42 | 3.39 | 52 | 46 | 1 | 3 | 3 | 0.0238 |
| 6 | 20 | 50307365 | rs117858424 | A | G | ATP9A | . | 1.66 | 2.26 | 52 | 46 | 2 | 4 | 4 | 0.0476 |
| 6 | 20 | 121997127 | rs147546143 | G | GACGGT | TFCP2L1 | . | 2.03 | 2.26 | 52 | 46 | 2 | 4 | 4 | 0.0565 |
| 6 | 2 | 128466446 | . | G | A | WDR33 | D | 1.9 | . | 208 | 184 | 0 | 5 | 5 | . |
| 6 | 2 | 128477849 | rs774069217 | C | T | WDR33 | D | 1.9 | . | 208 | 184 | 0 | 5 | 5 | . |
| 6 | 2 | 128522203 | rs117753184 | A | T | WDR33 | . | 1.9 | . | 208 | 184 | 0 | 5 | 5 | 0.0258 |
| 6 | 2 | 128522852 | . | G | A | WDR33 | . | 1.9 | . | 208 | 184 | 0 | 5 | 5 | . |
| 6 | 21 | 34860749 | . | CAATTA | C | DNAJC28 | . | 1.9 | 2.83 | 52 | 46 | 4 | 10 | 9 | 0.1667 |
| 6 | 21 | 42615293 | rs2252576 | C | T | BACE2 | . | 1.52 | 2.83 | 52 | 46 | 2 | 5 | 4 | 0.0675 |
| 6 | 21 | 43412786 | rs200509586 | GTCA | G | ZBTB21 | . | 11.41 | 5.65 | 52 | 46 | 1 | 5 | 5 | 0.0109 |
| 6 | 2 | 153515710 | rs141445791 | A | C | PRPF40A | . | 1.56 | . | 104 | 90 | 0 | 4 | 4 | 0.0278 |
| 6 | 2 | 153515879 | rs767401165 | A | G | PRPF40A | . | 1.56 | . | 104 | 90 | 0 | 4 | 4 | . |
| 6 | 2 | 169791766 | . | G | A | ABCB11 | D | 4.57 | 3.39 | 156 | 138 | 1 | 3 | 3 | . |
| 6 | 2 | 169801131 | rs118109635 | G | A | ABCB11 | D | 4.57 | 3.39 | 156 | 138 | 1 | 3 | 3 | 0.0129 |
| 6 | 2 | 169853135 | . | A | G | ABCB11 | . | 4.57 | 3.39 | 156 | 138 | 1 | 3 | 3 | . |
| 6 | 2 | 175304621 | rs67227536 | C | G | GPR155 | . | 6.85 | 3.39 | 104 | 92 | 1 | 3 | 3 | 0.0139 |
| 6 | 2 | 175333632 | rs28588913 | G | A | GPR155 | . | 6.85 | 3.39 | 104 | 92 | 1 | 3 | 3 | 0.0248 |

TABLE 9-continued

Candidate variant list from RA disease duration comparison.

| group | chr | pos | id | ref | alt | gene | LR | Gene burden ratio KG East Asia | Gene burden ratio ≤1-Year | Total No. of alleles in gene ≤1-Year | Total No. of alleles in gene ≥3-Year | No. alt alleles in genes ≤1-Year | No. alt alleles in genes ≥3-Year | No. of ≥3-Year cases with alt alleles | Variant allele frequency KG East Asia |
|---|---|---|---|---|---|---|---|---|---|---|---|---|---|---|---|
| 6 | 2 | 202498027 | rs78297522 | T | C | TMEM237 | . | 1.96 | 1.7 | 52 | 46 | 2 | 3 | 3 | 0.0298 |
| 6 | 22 | 19420778 | rs3747064 | T | A | MRPL40 | . | 1.52 | 4.52 | 52 | 46 | 1 | 4 | 4 | 0.0714 |
| 6 | 22 | 24313530 | rs199896117 | GGA | G | DDTL | . | 2.28 | 2.26 | 52 | 46 | 1 | 2 | 2 | 0.0278 |
| 6 | 22 | 24919647 | rs118163237 | G | A | UPB1 | D | 1.83 | 2.26 | 52 | 46 | 1 | 2 | 2 | 0.0188 |
| 6 | 2 | 231077154 | rs41309096 | G | A | SP110 | . | 1.83 | 1.7 | 52 | 46 | 4 | 6 | 6 | 0.0883 |
| 6 | 2 | 30862980 | rs12466818 | C | T | LCLAT1 | . | 1.52 | 1.98 | 52 | 46 | 8 | 14 | 11 | 0.2222 |
| 6 | 2 | 31412347 | rs78099670 | G | A | CAPN14 | . | 7.3 | 1.51 | 260 | 230 | 3 | 4 | 4 | 0.0179 |
| 6 | 2 | 31414833 | . | G | T | CAPN14 | D | 7.3 | 1.51 | 260 | 230 | 3 | 4 | 4 | . |
| 6 | 2 | 31414844 | rs147299374 | C | T | CAPN14 | D | 7.3 | 1.51 | 260 | 230 | 3 | 4 | 4 | . |
| 6 | 2 | 31414959 | rs141014145 | A | G | CAPN14 | D | 7.3 | 1.51 | 260 | 230 | 3 | 4 | 4 | 0.0149 |
| 6 | 2 | 31422395 | rs200657395 | TCTC | T | CAPN14 | . | 7.3 | 1.51 | 260 | 230 | 3 | 4 | 4 | 0.0139 |
| 6 | 2 | 55491007 | rs369772725 | G | GA | MTIF2 | . | 2.75 | 5.18 | 44 | 34 | 1 | 4 | 4 | 0.0486 |
| 6 | 2 | 98128073 | . | G | * | ANKRD36B | . | 1.86 | 2.71 | 116 | 110 | 14 | 36 | 33 | . |
| 6 | 2 | 98128073 | rs373085949 | G | A | ANKRD36B | . | 1.86 | 2.71 | 116 | 110 | 14 | 36 | 33 | 0.1796 |
| 6 | 2 | 98164184 | rs13001728 | C | G | ANKRD36B | . | 1.86 | 2.71 | 116 | 110 | 14 | 36 | 33 | . |
| 6 | 3 | 100593675 | rs79152576 | T | C | ABI3BP | . | 2.28 | 2.26 | 52 | 46 | 1 | 2 | 2 | 0.0139 |
| 6 | 3 | 107097080 | rs138204694 | CAAATG | C | CCDC54 | . | 2.61 | 4.52 | 52 | 46 | 1 | 4 | 4 | 0.0317 |
| 6 | 3 | 111780629 | rs73853301 | C | T | TMPRSS7 | . | 3.04 | 4.52 | 104 | 92 | 2 | 8 | 6 | 0.0258 |
| 6 | 3 | 111780630 | rs73853302 | C | T | TMPRSS7 | . | 3.04 | 4.52 | 104 | 92 | 2 | 8 | 6 | 0.0258 |
| 6 | 3 | 120428621 | rs11720353 | T | C | RABL3 | . | 1.68 | 1.58 | 52 | 46 | 5 | 7 | 7 | 0.127 |
| 6 | 3 | 122002576 | rs117375173 | A | G | CASR | D | 1.71 | 6.78 | 104 | 92 | 1 | 6 | 6 | 0.0446 |

TABLE 9-continued

Candidate variant list from RA disease duration comparison.

| group | chr | pos | id | ref | alt | gene | LR | KG East Asia | Gene burden ratio ≤1-Year | Total No. of alleles in gene ≤1-Year | ≥3-Year | No. alt alleles in genes ≤1-Year | ≥3-Year | No. of ≥3-Year cases with alt alleles | Variant allele frequency KG East Asia |
|---|---|---|---|---|---|---|---|---|---|---|---|---|---|---|---|
| 6 | 3 | 122002644 | rs768660050 | G | T | CASR | D | 1.71 | 6.78 | 104 | 92 | 1 | 6 | 6 | . |
| 6 | 3 | 133331230 | rs71317417 | C | T | TOPBP1 | . | 2.28 | 2.26 | 52 | 46 | 1 | 2 | 2 | 0.0437 |
| 6 | 3 | 182871464 | rs500288 | A | G | LAMP3 | . | 3.42 | 1.7 | 52 | 46 | 2 | 3 | 3 | 0.0317 |
| 6 | 3 | 196296182 | rs79085393 | G | C | FBXO45 | . | 1.9 | 1.88 | 52 | 46 | 3 | 5 | 5 | 0.0665 |
| 6 | 3 | 46714821 | rs11130104 | C | G | ALS2CL | . | 1.56 | 1.88 | 52 | 46 | 18 | 30 | 20 | 0.3571 |
| 6 | 3 | 56682841 | rs71621834 | A | C | FAM208A | . | 3.18 | 2.36 | 52 | 44 | 2 | 4 | 4 | 0.0327 |
| 6 | 3 | 58620105 | rs76752946 | G | C | FAM3D | . | 2.61 | 4.52 | 52 | 46 | 1 | 4 | 4 | 0.0308 |
| 6 | 3 | 141458699 | rs149594258 | A | C | ELMOD2 | . | 1.96 | 3.39 | 52 | 46 | 1 | 3 | 3 | 0.0208 |
| 6 | 4 | 184367558 | rs10533201 | TCTG | T | CDKN2AIP | . | 1.66 | 2.01 | 52 | 46 | 9 | 16 | 13 | 0.244 |
| 6 | 4 | 20751278 | rs2322688 | A | G | KCNIP4 | . | 1.65 | 1.84 | 52 | 46 | 8 | 13 | 11 | 0.1726 |
| 6 | 4 | 48517296 | rs757286932 | C | A | FRYL | . | 1.52 | 2.83 | 260 | 230 | 2 | 5 | 5 | . |
| 6 | 4 | 48545814 | rs10517225 | A | T | FRYL | . | 1.52 | 2.83 | 260 | 230 | 2 | 5 | 5 | 0.0238 |
| 6 | 4 | 48546796 | rs78799039 | A | G | FRYL | . | 1.52 | 2.83 | 260 | 230 | 2 | 5 | 5 | . |
| 6 | 4 | 48549674 | rs776615697 | GAGA | G | FRYL | . | 1.52 | 2.83 | 260 | 230 | 2 | 5 | 5 | . |
| 6 | 4 | 48559138 | rs779161058 | AG | A | FRYL | . | 1.52 | 2.83 | 260 | 230 | 2 | 5 | 5 | . |
| 6 | 4 | 48893993 | rs749533750 | CTTG | C | CWH43 | . | 1.71 | . | 104 | 92 | 0 | 3 | 3 | . |
| 6 | 4 | 49034669 | rs147750792 | CA | C | CWH43 | . | 1.71 | . | 104 | 92 | 0 | 3 | 3 | 0.0149 |
| 6 | 4 | 69094459 | rs75647314 | C | A | TMPRSS11B | . | 3.04 | 2.26 | 104 | 92 | 2 | 4 | 4 | 0.0278 |
| 6 | 4 | 69096987 | rs575638339 | C | T | TMPRSS11B | D | 3.04 | 2.26 | 104 | 92 | 2 | 4 | 4 | . |
| 6 | 4 | 70078281 | rs62298955 | G | C | UGT2B11 | . | 1.96 | 3.39 | 52 | 46 | 1 | 3 | 3 | 0.0476 |
| 6 | 4 | 77940418 | rs28541859 | T | A | SEPT11 | . | 1.52 | 2.26 | 52 | 46 | 4 | 8 | 8 | 0.1012 |
| 6 | 5 | 151784206 | rs145273801 | G | A | NMUR2 | . | 1.71 | 1.7 | 104 | 92 | 2 | 3 | 3 | 0.0248 |

TABLE 9-continued

Candidate variant list from RA disease duration comparison.

| group | chr | pos | id | ref | alt | gene | LR | Gene burden ratio KG East Asia | Gene burden ratio ≤1-Year | Total No. of alleles in gene ≤1-Year | Total No. of alleles in gene ≥3-Year | No. alt alleles in genes ≤1-Year | No. alt alleles in genes ≥3-Year | No. of ≥3-Year cases with alt alleles | Variant allele frequency KG East Asia |
|---|---|---|---|---|---|---|---|---|---|---|---|---|---|---|---|
| 6 | 5 | 151784490 | rs762380505 | C | A | NMUR2 | D | 1.71 | 1.7 | 104 | 92 | 2 | 3 | 3 | . |
| 6 | 5 | 170221307 | rs117380156 | G | A | GABRP | . | 3.42 | 3.39 | 104 | 92 | 1 | 3 | 3 | 0.0159 |
| 6 | 5 | 170236578 | rs558177227 | C | T | GABRP | D | 3.42 | 3.39 | 104 | 92 | 1 | 3 | 3 | . |
| 6 | 5 | 74998426 | rs17649248 | G | A | POC5 | . | 1.62 | 1.98 | 104 | 92 | 12 | 21 | 19 | 0.119 |
| 6 | 5 | 75008193 | rs2047059 | T | C | POC5 | . | 1.62 | 1.98 | 104 | 92 | 12 | 21 | 19 | 0.2153 |
| 6 | 6 | 106978193 | rs17495742 | A | G | AIM1 | . | 1.76 | 2.79 | 154 | 138 | 2 | 5 | 4 | . |
| 6 | 6 | 106991361 | rs61741114 | T | C | AIM1 | D | 1.76 | 2.79 | 154 | 138 | 2 | 5 | 4 | . |
| 6 | 6 | 107016343 | rs3747789 | T | G | AIM1 | . | 1.76 | 2.79 | 154 | 138 | 2 | 5 | 4 | 0.0694 |
| 6 | 6 | 10927469 | rs770638323 | A | G | SYCP2L | . | 3.42 | 3.39 | 104 | 92 | 1 | 3 | 2 | . |
| 6 | 6 | 10935424 | rs181416897 | C | T | SYCP2L | . | 3.42 | 3.39 | 104 | 92 | 1 | 3 | 2 | 0.0109 |
| 6 | 6 | 142487469 | rs225656 | C | A | VTA1 | . | 1.76 | 1.91 | 104 | 92 | 16 | 27 | 25 | 0.1845 |
| 6 | 6 | 142510676 | rs3830800 | GTATT | G | VTA1 | . | 1.76 | 1.91 | 104 | 92 | 16 | 27 | 25 | 0.1468 |
| 6 | 6 | 26410148 | rs777221150 | T | C | BTN3A1 | . | 2.71 | 4.52 | 156 | 138 | 2 | 8 | 8 | 0.0248 |
| 6 | 6 | 26410227 | rs7770214 | G | A | BTN3A1 | . | 2.71 | 4.52 | 156 | 138 | 2 | 8 | 8 | 0.0308 |
| 6 | 6 | 26410266 | . | T | C | BTN3A1 | . | 2.71 | 4.52 | 156 | 138 | 2 | 8 | 8 | . |
| 6 | 6 | 28268497 | rs2281043 | C | T | PGBD1 | . | 2.85 | 2.83 | 52 | 46 | 4 | 10 | 9 | 0.1448 |
| 6 | 6 | 30574428 | . | A | G | PPP1R10 | . | 3.42 | . | 52 | 46 | 0 | 3 | 3 | 0.0218 |
| 6 | 6 | 30618867 | . | T | C | C6orf136 | . | 1.76 | 2.83 | 52 | 46 | 2 | 5 | 4 | 0.0595 |
| 6 | 6 | 30670948 | rs536243116 | C | T | MDC1 | D | 2.11 | 3.39 | 156 | 138 | 2 | 6 | 5 | . |
| 6 | 6 | 30679289 | rs147822906 | G | C | MDC1 | . | 2.11 | 3.39 | 156 | 138 | 2 | 6 | 5 | 0.0198 |
| 6 | 6 | 30679510 | rs17189329 | G | A | MDC1 | . | 2.11 | 3.39 | 156 | 138 | 2 | 6 | 5 | 0.0595 |

TABLE 9-continued

Candidate variant list from RA disease duration comparison.

| group | chr | pos | id | ref | alt | gene | LR | Gene burden ratio KG East Asia | Gene burden ratio ≤1-Year | Total No. of alleles in gene ≤1-Year | Total No. of alleles in gene ≥3-Year | No. alt alleles in genes ≤1-Year | No. alt alleles in genes ≥3-Year | No. of ≥3-Year cases with alt alleles | Variant allele frequency KG East Asia |
|---|---|---|---|---|---|---|---|---|---|---|---|---|---|---|---|
| 6 | 6 | 31733650 | rs707936 | G | A | VWA7 | . | 2.08 | . | 52 | 46 | 0 | 5 | 4 | 0.0615 |
| 6 | 6 | 31948421 | . | TCTC | T | STK19 | . | 2.15 | 1.51 | 52 | 46 | 6 | 8 | 8 | 0.0972 |
| 6 | 6 | 36929653 | rs144897670 | C | T | PI16 | . | 3.04 | 2.26 | 52 | 46 | 1 | 2 | 2 | 0.0129 |
| 6 | 6 | 397261 | rs34318727 | G | A | IRF4 | . | 2.08 | 5.65 | 52 | 46 | 1 | 5 | 5 | 0.0496 |
| 6 | 6 | 46133282 | rs16874326 | T | C | ENPP5 | D | 1.52 | 3.39 | 52 | 46 | 1 | 3 | 3 | 0.0407 |
| 6 | 6 | 72011086 | rs16880821 | C | T | OGFRL1 | . | 4.57 | . | 52 | 46 | 0 | 3 | 3 | 0.0149 |
| 6 | 6 | 87994504 | rs35259282 | C | T | GJB7 | D | 2.28 | 2.26 | 104 | 92 | 1 | 2 | 2 | 0.0188 |
| 6 | 6 | 87994537 | rs112552839 | G | A | GJB7 | D | 2.28 | 2.26 | 104 | 92 | 1 | 2 | 2 | . |
| 6 | 6 | 100230618 | rs41303468 | A | T | TFR2 | . | 2.28 | 2.26 | 52 | 46 | 1 | 2 | 2 | 0.0139 |
| 6 | 7 | 140125701 | rs760033770 | G | A | RAB19 | . | 2.54 | 5.65 | 156 | 138 | 1 | 5 | 5 | . |
| 6 | 7 | 140125753 | rs771901851 | G | A | RAB19 | D | 2.54 | 5.65 | 156 | 138 | 1 | 5 | 5 | . |
| 6 | 7 | 140174292 | rs10709936 | CA | C | MKRN1 | . | 1.95 | 1.66 | 42 | 38 | 8 | 12 | 10 | 0.1766 |
| 6 | 7 | 142562051 | rs143667567 | C | CCCTCCT | EPHB6 | . | 2.74 | 1.61 | 148 | 138 | 4 | 6 | 6 | 0.0238 |
| 6 | 7 | 142562051 | rs143667567 | C | CCCT | EPHB6 | . | 2.74 | 1.61 | 148 | 138 | 4 | 6 | 6 | 0.0139 |
| 6 | 7 | 142565743 | rs8177158 | G | A | EPHB6 | . | 2.74 | 1.61 | 148 | 138 | 4 | 6 | 6 | . |
| 6 | 7 | 156468559 | rs3823617 | T | C | RNF32 | . | 1.52 | 1.7 | 52 | 46 | 4 | 6 | 6 | 0.1111 |
| 6 | 7 | 28534518 | rs77306029 | C | T | CREB5 | . | 2.28 | 2.26 | 52 | 46 | 2 | 4 | 4 | 0.0397 |
| 6 | 7 | 72984917 | . | CGTT | C | TBL2 | . | 4.57 | . | 52 | 46 | 0 | 5 | 5 | 0.0159 |
| 6 | 8 | 17104886 | rs145945235 | G | A | VPS37A | . | 1.79 | 2.44 | 44 | 36 | 2 | 4 | 4 | 0.0526 |
| 6 | 8 | 37791988 | rs201462725 | GT | G | GOT1L1 | . | 2.74 | 1.7 | 52 | 46 | 2 | 3 | 3 | 0.0337 |
| 6 | 8 | 87163770 | rs150698519 | G | T | ATP6V0D2 | . | 1.83 | 2.26 | 52 | 46 | 1 | 2 | 2 | 0.0149 |
| 6 | 8 | 95188916 | rs67774240 | G | A | CDH17 | . | 1.83 | 3.39 | 156 | 138 | 1 | 3 | 3 | 0.0278 |

TABLE 9-continued

Candidate variant list from RA disease duration comparison.

| group | chr | pos | id | ref | alt | gene | LR | Gene burden ratio KG East Asia | Gene burden ratio ≤1-Year | Total No. of alleles in gene ≤1-Year | Total No. of alleles in gene ≥3-Year | No. alt alleles in genes ≤1-Year | No. alt alleles in genes ≥3-Year | No. of ≥3-Year cases with alt alleles | Variant allele frequency KG East Asia |
|---|---|---|---|---|---|---|---|---|---|---|---|---|---|---|---|
| 6 | 8 | 95189955 | rs1380007982 | G | T | CDH17 | . | 1.83 | 3.39 | 156 | 138 | 1 | 3 | 3 | 0.0139 |
| 6 | 8 | 95201518 | rs749070399 | TAAAAA | T | CDH17 | . | 1.83 | 3.39 | 156 | 138 | 1 | 3 | 3 | . |
| 6 | 9 | 100693386 | rs201990544 | CACT | C | HEMGN | . | 6.85 | 3.39 | 52 | 46 | 1 | 3 | 3 | 0.0129 |
| 6 | 9 | 101984010 | rs201959100 | G | A | ALG2 | D | 6.85 | . | 52 | 46 | 0 | 3 | 3 | 0.0188 |
| 6 | 9 | 127074783 | rs139169292 | TC | T | NEK6 | . | 1.59 | 2.26 | 104 | 92 | 8 | 16 | 16 | 0.0923 |
| 6 | 9 | 127076271 | rs56045213 | A | G | NEK6 | . | 1.59 | 2.26 | 104 | 92 | 8 | 16 | 16 | 0.0923 |
| 6 | 9 | 5892552 | rs148372841 | G | C | MLANA | . | 9.13 | 4.52 | 52 | 46 | 1 | 4 | 4 | 0.0139 |
| 6 | 9 | 95411725 | rs72756427 | G | A | IPPK | . | 2.74 | 1.7 | 52 | 46 | 2 | 3 | 3 | 0.0476 |
| 6 | X | 31089629 | rs7057057 | C | A | FTHL17 | . | 1.73 | 2.26 | 52 | 46 | 3 | 6 | 5 | 0.1453 |
| 6 | X | 49114808 | . | C | A | FOXP3 | D | 2.88 | 1.88 | 52 | 46 | 3 | 5 | 4 | 0.0393 |

TABLE 10

Susceptibility genes unique to disease duration with exonic variants in Rheumatoid Arthritis disease.

| | | | |
|---|---|---|---|
| AMPD1 | ATXN7 | GPR84 | OR7G3 |
| PPARGC18 | C10orf142 | OR9K2 | CST9 |
| ATP6V0A4 | CH17-360D5.1 | OR6C74 | WDR33 |
| HKDC1 | NPY4R | OR6C75 | DNAJC28 |
| C1orf167 | LRRC39 | CATSPER4 | DDTL |
| SLCO1B3 | GPSM2 | NR2C1 | UPB1 |
| MYH1 | ITGA10 | SERPINA10 | LCLAT1 |
| SGCA | LCE5A | RORA | CASR |
| RYR1 | OR4A15 | TPSG1 | CDKN2AIP |
| KIZ | OR52N4 | NEK8 | FRYL |
| TPTE | SLAMF8 | HEATR9 | CWH43 |
| LRP2 | MTA2 | PNMT | NMUR2 |
| DYSF | EML3 | ABCC3 | GABRP |
| COL6A6 | GPR161 | NACA2 | MDC1 |
| CP | IL18BP | CACNG5 | ENPPS |
| HTR3E | PANO1 | AURKB | RAB19 |
| TET2 | LHX4 | PLEKHG2 | EPHB6 |
| THBS2 | LAD1 | PSG8 | GOT1L1 |
| FLNC | SYT14 | CBLC | HEMGN |
| SSPO | FAAP20 | CARD8 | ALG2 |
| PKHD1L1 | HIST4H4 | TARM1 | FTHL17 |
| IL3RA | OR14C36 | PRR36 | |

The invention claimed is:

1. A method of identifying a gene associated with a disease or pathological condition of the disease, comprising the steps of:

a) obtaining a first group of exome sequences from a first population of individuals and a second group of exome sequences from a second population of individuals through whole-exome sequencing, wherein the first population of individuals suffer from the disease or pathological condition of the disease, and the second population of individuals do not have the disease or pathological condition of the disease;

b) identifying one or more variants in the first group of exome sequences by comparing the first group of exome sequences with the second group of exome sequences to generate a first set of variant data;

c) applying a variant quality score calibration tool with a truth sensitivity threshold to remove false-positive variants having a sensitivity lower than the threshold and background variants from the first set of variant data so as to obtain a second set of variant data;

d) removing synonymous variants from the second set of variant data to obtain a third set of variant data;

e) identifying one or more deleterious variants from the third set of variant data using a gene burden analysis, generating a fourth set of variant data; and f) determining a pathogenic gene associated with the disease or pathological condition of the disease from the fourth set of variant data by using a logistic regression model and public accessible database for diagnosis.

2. The method of claim 1 further comprises a step of confirming the ethnicity of the first and second population of individuals via ancestry composition analysis.

3. The method of claim 1, wherein the step (c) comprises a step (i) of applying the variant quality score calibration tool with the truth sensitivity threshold of about 90% to remove the false-positive variants, and removing the background variants having a read depth of less than 5 and a genotype quality of less than 10 from the first set of variant data.

4. The method of claim 3, wherein the applied truth sensitivity threshold is about 99%, the read depth is less than 10 and the genotype quality is less than 20.

5. The method of claim 3, wherein the step (c) further comprises a step (ii) of screening the resultant variants from step c) (i) based on the dataset provided by UCSC genome browser to keep exonic or slicing variants in the second set of variant data.

6. The method of claim 1, wherein the step e) comprises a step (i) of identifying one or more deleterious variants having a gene burden ratio of larger than 1, or being present in the first group of exome sequences in an amount of at least three but absent in the second group of exome sequences.

7. The method of claim 6, wherein the step e) further comprises a step (ii) of grouping the identified one or more deleterious variants whose minor allele frequency is smaller than 0.02, into a rare variant group, and grouping the rest of the identified one or more deleterious variants into a common variant group.

8. The method of claim 1, wherein a biological pathway analysis is performed after the step e) or step f) to determine the functional role of the identified one or more deleterious variants.

9. The method of claim 1, wherein a structural analysis using a homology modeling is applied to determine the structure of protein associated with the identified one or more deleterious variants.

10. The method of claim 1, wherein the disease is selected from the group consisting of an autoimmune disease, a neurodegenerative disease, a cardiovascular disease, a cancer, a gastrointestinal disease, an inflammatory disease, or an endocrine disease.

11. The method of claim 1, wherein the disease is rheumatoid arthritis.

12. The method of claim 1, wherein the step b) is conducted with a public database.

* * * * *

SEQUENCE LISTING

<160> NUMBER OF SEQ ID NOS: 12

<210> SEQ ID NO 1
<211> LENGTH: 10
<212> TYPE: DNA
<213> ORGANISM: Homo sapiens

<400> SEQUENCE: 1
gaccagaacc          10

<210> SEQ ID NO 2
<211> LENGTH: 15
<212> TYPE: DNA
<213> ORGANISM: Homo sapiens

<400> SEQUENCE: 2
tgctaggccc cagcc          15

<210> SEQ ID NO 3
<211> LENGTH: 19
<212> TYPE: DNA
<213> ORGANISM: Homo sapiens

<400> SEQUENCE: 3
gctgctgctg ctgcggctt          19

<210> SEQ ID NO 4
<211> LENGTH: 11
<212> TYPE: DNA
<213> ORGANISM: Homo sapiens

<400> SEQUENCE: 4
atgtgtgtgt g          11

<210> SEQ ID NO 5
<211> LENGTH: 28
<212> TYPE: DNA
<213> ORGANISM: Homo sapiens

<400> SEQUENCE: 5
cctgctgctg ctgctgctgc tgctgctg          28

<210> SEQ ID NO 6
<211> LENGTH: 19
<212> TYPE: DNA
<213> ORGANISM: Homo sapiens

<400> SEQUENCE: 6

```
cctgctgctg ctgctgctg                                              19

<210> SEQ ID NO 7
<211> LENGTH: 20
<212> TYPE: DNA
<213> ORGANISM: Homo sapiens

<400> SEQUENCE: 7
acccaacaac tggtatcttt                                             20

<210> SEQ ID NO 8
<211> LENGTH: 19
<212> TYPE: DNA
<213> ORGANISM: Homo sapiens

<400> SEQUENCE: 8
gctgctgctg ctgcggctt                                              19

<210> SEQ ID NO 9
<211> LENGTH: 10
<212> TYPE: DNA
<213> ORGANISM: Homo sapiens

<400> SEQUENCE: 9
gaccagaacc                                                        10

<210> SEQ ID NO 10
<211> LENGTH: 10
<212> TYPE: DNA
<213> ORGANISM: Homo sapiens

<400> SEQUENCE: 10
tgcacgctgg                                                        10

<210> SEQ ID NO 11
<211> LENGTH: 37
<212> TYPE: DNA
<213> ORGANISM: Homo sapiens

<400> SEQUENCE: 11 acactgggggg tgaggcaggg ggagagaaag gggcctg                         37

<210> SEQ ID NO 12
<211> LENGTH: 37
<212> TYPE: DNA
<213> ORGANISM: Homo sapiens

<400> SEQUENCE: 12 caggggggaga gaaaggggcc tgcactgggg gtgaggg                         37
```